United States Patent
Fujiwara et al.

(10) Patent No.: US 10,180,626 B2
(45) Date of Patent: Jan. 15, 2019

(54) SULFONIUM SALT, RESIST COMPOSITION, AND PATTERNING PROCESS

(71) Applicant: Shin-Etsu Chemical Co., Ltd., Tokyo (JP)

(72) Inventors: Takayuki Fujiwara, Joetsu (JP); Masaki Ohashi, Joetsu (JP); Ryosuke Taniguchi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/703,037

(22) Filed: Sep. 13, 2017

(65) Prior Publication Data

US 2018/0088464 A1 Mar. 29, 2018

(30) Foreign Application Priority Data

Sep. 27, 2016 (JP) ................. 2016-188374

(51) Int. Cl.

| G03F 7/004 | (2006.01) |
| --- | --- |
| G03F 7/039 | (2006.01) |
| H01L 21/027 | (2006.01) |
| C07C 323/37 | (2006.01) |
| C07D 333/20 | (2006.01) |
| C07D 409/10 | (2006.01) |
| C07C 309/12 | (2006.01) |
| C07C 381/12 | (2006.01) |
| C07J 31/00 | (2006.01) |
| G03F 7/16 | (2006.01) |
| G03F 7/20 | (2006.01) |
| G03F 7/32 | (2006.01) |
| G03F 7/38 | (2006.01) |
| G03F 7/40 | (2006.01) |

(52) U.S. Cl.
CPC .......... *G03F 7/0045* (2013.01); *C07C 309/12* (2013.01); *C07C 323/37* (2013.01); *C07C 381/12* (2013.01); *C07D 333/20* (2013.01); *C07D 409/10* (2013.01); *C07J 31/006* (2013.01); *G03F 7/0397* (2013.01); *H01L 21/0274* (2013.01); *C07C 2603/74* (2017.05); *G03F 7/16* (2013.01); *G03F 7/2004* (2013.01); *G03F 7/2006* (2013.01); *G03F 7/2041* (2013.01); *G03F 7/322* (2013.01); *G03F 7/325* (2013.01); *G03F 7/38* (2013.01); *G03F 7/40* (2013.01)

(58) Field of Classification Search
CPC ...... G03F 7/004; G03F 7/0392; G03F 7/0045; G03F 7/0397; G03F 7/40; H01L 21/0274; C07C 381/12
USPC ...................... 430/270.1, 913, 330, 331, 322
See application file for complete search history.

(56) References Cited

U.S. PATENT DOCUMENTS

| 7,511,169 B2 | 3/2009 | Ohsawa et al. |
| --- | --- | --- |
| 8,034,547 B2 | 10/2011 | Tsubaki et al. |
| 8,227,183 B2 | 7/2012 | Tsubaki et al. |
| 2005/0173683 A1* | 8/2005 | Marder ............ C07C 211/54 252/600 |
| 2014/0322650 A1 | 10/2014 | Ohashi et al. |

FOREIGN PATENT DOCUMENTS

| JP | 2007-145797 A | 6/2007 |
| --- | --- | --- |
| JP | 2008-281974 A | 11/2008 |
| JP | 2008-281975 A | 11/2008 |
| JP | 4554665 B2 | 9/2010 |
| KR | 10-2014-0128258 A | 11/2014 |

OTHER PUBLICATIONS

Dammel et al., "193 nm Immersion Lithography—Taking the Plunge", Journal of Photopolymer Science and Technology, vol. 17, No. 4, pp. 587-602, (2004).

Office Action dated Oct. 16, 2018, issued in counterpart Korean Application No. 10-2017-0124329, with English translation. (14 pages).

* cited by examiner

*Primary Examiner* — Amanda C. Walke
(74) *Attorney, Agent, or Firm* — Westerman, Hattori, Daniels & Adrian, LLP

(57) ABSTRACT

On use of a sulfonium salt of specific structure as PAG, acid diffusion is suppressed. A resist composition comprising the sulfonium salt forms a pattern with improved lithography properties including EL, MEF and LWR when processed by lithography.

19 Claims, No Drawings

SULFONIUM SALT, RESIST COMPOSITION, AND PATTERNING PROCESS

CROSS-REFERENCE TO RELATED APPLICATION

This non-provisional application claims priority under 35 U.S.C. § 119(a) on Patent Application No. 2016-188374 filed in Japan on Sep. 27, 2016, the entire contents of which are hereby incorporated by reference.

TECHNICAL FIELD

This invention relates to a sulfonium salt, a resist composition comprising the same, and a pattern forming process using the resist composition.

BACKGROUND ART

While a number of recent efforts are being made to achieve a finer pattern rule in the drive for higher integration and operating speeds in LSI devices, DUV and EUV lithography processes are thought to hold particular promise as the next generation in microfabrication technology. In particular, photolithography using ArF excimer laser is requisite to the micropatterning technique capable of achieving a feature size of 0.13 µm or less.

The ArF lithography started partial use from the fabrication of 130-nm node devices and became the main lithography since 90-nm node devices. Although lithography using $F_2$ laser (157 nm) was initially thought promising as the next lithography for 45-nm node devices, its development was retarded by several problems. A highlight was suddenly placed on the ArF immersion lithography that introduces a liquid having a higher refractive index than air (e.g., water, ethylene glycol, glycerol) between the projection lens and the wafer, allowing the projection lens to be designed to a numerical aperture (NA) of 1.0 or higher and achieving a higher resolution. See Non-Patent Document 1. The ArF immersion lithography is now implemented on the commercial stage. The immersion lithography requires a resist composition which is substantially insoluble in water.

In the ArF (193 nm) lithography, a high sensitivity resist composition capable of achieving a high resolution at a small dose of exposure is needed to prevent the degradation of precise and expensive optical system materials. Among several measures for providing high sensitivity resist compositions, the most common is to select each component which is highly transparent at the wavelength of 193 nm. For example, polymers of acrylic acid and derivatives thereof, norbornene-maleic anhydride alternating copolymers, polynorbornene, ring-opening metathesis polymerization (ROMP) polymers, and hydrogenated ROMP polymers have been proposed as the base resin. This choice is effective to some extent in that the transparency of a resin alone is increased.

Recently a highlight is put on the negative tone resist adapted for organic solvent development as well as the positive tone resist adapted for aqueous alkaline development. It would be desirable if a very fine hole pattern, which is not achievable with the positive tone, is resolvable through negative tone exposure. To this end, a positive resist composition featuring a high resolution is subjected to organic solvent development to form a negative pattern. An attempt to double a resolution by combining two developments, aqueous alkaline development and organic solvent development is under study. As the ArF resist composition for negative tone development with organic solvent, positive ArF resist compositions of the prior art design may be used. Such pattern forming processes are described in Patent Documents 1 to 3.

To meet the current rapid progress of microfabrication technology, development efforts are put on not only the process, but also the resist composition. Studies have also been made on photoacid generators (PAGs). Commonly used are sulfonium salts of triphenylsulfonium cation with perluoroalkanesulfonic acid anion. These salts generate perfluoroalkanesulfonic acids, especially perfluorooctanesulfonic acid (PFOS), which are considered problematic with respect to their non-degradability, biological concentration and toxicity. It is rather restricted to apply these salts to the resist composition. Instead, PAGs capable of generating perfluorobutanesulfonic acid are currently used, but are awkward to achieve a high resolution because of substantial diffusion of the generated acid in the resist composition. To address the problem, partially fluorinated alkane sulfonic acids and salts thereof are developed. For instance, Patent Document 1 refers to the prior art PAGs capable of generating α,α-difluoroalkanesulfonic acid, such as di(4-t-butylphenyl)iodonium 1,1-difluoro-2-(1-naphthyl)ethanesulfonate and PAGs capable of generating α,α,β,β (tetrafluoroalkanesulfonic acid. Despite a reduced degree of fluorine substitution, these PAGs still have the following problems. Since they do not have a decomposable substituent group such as ester structure, they are unsatisfactory from the aspect of environmental safety due to ease of decomposition. The molecular design to change the size of alkanesulfonic acid is limited. Fluorine-containing starting reactants are expensive.

As the circuit line width is reduced, the degradation of contrast by acid diffusion becomes more serious for the resist material. The reason is that the pattern feature size is approaching the diffusion length of acid. This invites a lowering of mask fidelity and a degradation of pattern rectangularity because a dimensional shift on wafer (known as mask error factor (MEF)) relative to a dimensional shift on mask is exaggerated. Accordingly, to gain more benefits from a reduction of exposure light wavelength and an increase of lens NA, the resist material is required to increase a dissolution contrast or restrain acid diffusion, as compared with the prior art materials. One approach is to lower the bake temperature for suppressing acid diffusion and hence, improving MEF. A low bake temperature, however, inevitably leads to a low sensitivity.

Incorporating a bulky substituent or polar group into PAG is effective for suppressing acid diffusion. Patent Document 4 describes a PAG capable of generating 2-acyloxy-1,3,3,3-pentafluoropropane-1-sulfonic acid which is fully soluble and stable in organic solvents and allows for a wide span of molecular design. In particular, a PAG having incorporated therein a bulky substituent, 2-(1-adamantyloxy)-1,1,3,3,3-pentafluoropropane-1-sulfonic acid is characterized by slow acid diffusion. A resist composition comprising this PAG, however, is still insufficient in precise control of acid diffusion, and its lithography performance is unsatisfactory when evaluated totally in terms of MEF, pattern profile, and sensitivity.

CITATION LIST

Patent Document 1: JP-A 2008-281974
Patent Document 2: JP-A 2008-281975
Patent Document 3: JP 4554665 (U.S. Pat. No. 8,227,183)
Patent Document 4: JP-A 2007-145797

Non-Patent Document 1: Journal of Photopolymer Science and Technology, Vol. 17, No. 4, p 587 (2004)

DISCLOSURE OF THE INVENTION

With respect to the recent demand for high resolution of resist patterns, resist compositions comprising conventional photoacid generators fail to fully suppress acid diffusion, resulting in degradations of lithography properties including contrast, MEF, and LWR.

An object of the invention is to provide a photoacid generator, a resist composition comprising the photoacid generator, and a patterning process using the resist composition, wherein the composition is minimized in acid diffusion and improved in lithography properties including exposure latitude (EL), MEF, and LWR when processed by KrF excimer laser, ArF excimer laser, EUV or EB lithography.

The inventors have found that a resist composition comprising a sulfonium salt of specific structure is minimized in acid diffusion, improved in lithography properties including EL, MEF, and LWR, and is effective for precise micropatterning.

In one aspect, the invention provides a sulfonium salt having the formula (1).

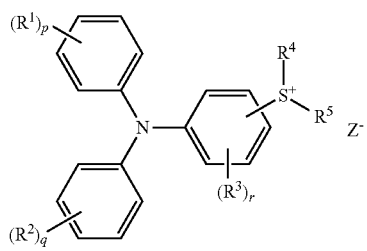

(1)

Herein $R^1$ to $R^3$ are each independently a $C_1$-$C_{20}$ straight, branched or cyclic monovalent hydrocarbon group which may contain a heteroatom, a pair of $R^1$ and $R^2$, $R^1$ and $R^3$, or $R^2$ and $R^3$ may bond together to form a ring with the benzene rings to which they are attached and the nitrogen atom therebetween, or a plurality of groups $R^1$ to $R^3$ may be the same or different and bond together to form a ring with the carbon atoms on the benzene ring to which they are attached, when p, q and/or r is an integer of at least 2, $R^4$ and $R^5$ are each independently a $C_1$-$C_{30}$ straight, branched or cyclic monovalent hydrocarbon group which may contain a heteroatom, or a pair of $R^4$ and $R^5$ may bond together to form a ring with the sulfur atom to which they are attached, p and q are each independently an integer of 0 to 5, r is an integer of 0 to 4, and $Z^-$ is a monovalent anion.

The preferred sulfonium salt has the formula (2).

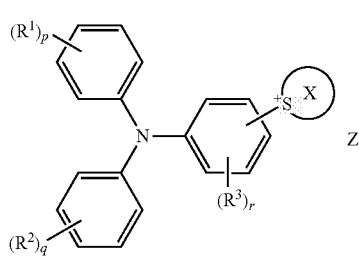

(2)

Herein $R^1$ to $R^3$, p, q, r and $Z^-$ are as defined above, the ring X is a $C_2$-$C_{30}$ cyclic hydrocarbon group which contains the sulfur atom as a part of the ring and may contain a heteroatom.

In a preferred embodiment, Z is an anion having the formula (3).

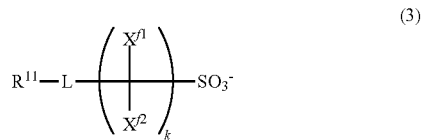

(3)

Herein $R^{11}$ is a $C_1$-$C_{40}$ straight, branched or cyclic monovalent hydrocarbon group which may contain a heteroatom, L is a single bond or a divalent linking group, $X^{f1}$ and $X^{f2}$ are each independently hydrogen, fluorine or a fluorinated alkyl group, and k is an integer of 0 to 4.

In a preferred embodiment, the anion has the formula (4) or (5).

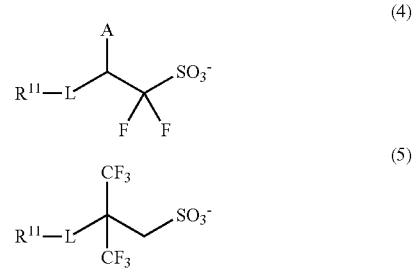

(4)

(5)

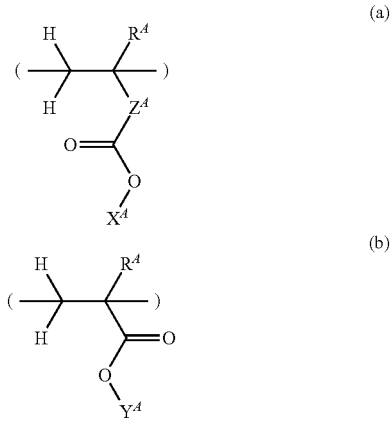

Herein $R^{11}$ and L are as defined above, A is hydrogen or trifluoromethyl.

In a second aspect, the invention provides a photoacid generator comprising the sulfonium salt defined above.

In a third aspect, the invention provides a resist composition comprising the photoacid generator defined above.

The resist composition may further comprise a base resin containing a polymer comprising recurring units having the formula (a) and recurring units having the formula (b).

(a)

(b)

Herein $R^A$ is hydrogen, fluorine, methyl or trifluoromethyl, $Z^A$ is a single bond, phenylene group, naphthylene group or (backbone)—C(=O)—O—Z'—, Z' is a $C_1$-$C_{10}$ straight, branched or cyclic alkylene group which may contain a hydroxyl radical, ether bond, ester bond or lactone ring, or phenylene group or naphthylene group, $X^A$ is an acid labile group, and $Y^A$ is hydrogen or a polar group having at least one structure selected from the group consisting of hydroxyl, cyano, carbonyl, carboxyl, ether, ester, sulfonic acid ester, carbonate moiety, lactone ring, sultone ring and carboxylic anhydride.

The resist composition may further comprise an organic solvent.

The resist composition may further comprise a photoacid generator other than the photoacid generator defined above.

Preferably the other photoacid generator has the formula (6) or (7).

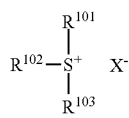

Herein $R^{101}$, $R^{102}$ and $R^{103}$ are each independently a $C_1$-$C_{20}$ straight, branched or cyclic monovalent hydrocarbon group which may contain a heteroatom, any two of $R^{101}$, $R^{102}$ and $R^{103}$ may bond together to form a ring with the sulfur atom to which they are attached, $X^-$ is an anion selected from the formulae (6A) to (6D):

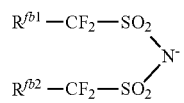

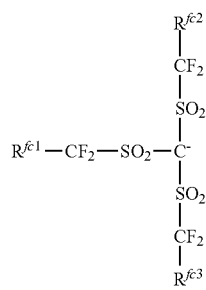

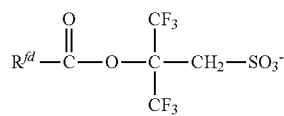

wherein $R^{fa}$, $R^{fb1}$, $R^{fb2}$, $R^{fc1}$, $R^{fc2}$ and $R^{fc3}$ are each independently fluorine or a $C_1$-$C_{40}$ straight, branched or cyclic monovalent hydrocarbon group which may contain a heteroatom, or a pair of $R^{fb1}$ and $R^{fb2}$, or $R^{fc1}$ and $R^{fc2}$ may bond together to form a ring with the carbon atoms to which they are attached and any intervening atoms, $R^{fd}$ is a $C_1$-$C_{40}$ straight, branched or cyclic monovalent hydrocarbon group which may contain a heteroatom;

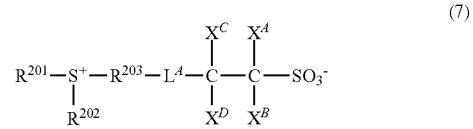

wherein $R^{201}$ and $R^{202}$ are each independently a $C_1$-$C_{30}$ straight, branched or cyclic monovalent hydrocarbon group which may contain a heteroatom, $R^{203}$ is a $C_1$-$C_{30}$ straight, branched or cyclic divalent hydrocarbon group which may contain a heteroatom, any two of $R^{201}$, $R^{202}$ and $R^{203}$ may bond together to form a ring with the sulfur atom to which they are attached; $L^A$ is a single bond, ether bond, or a $C_1$-$C_{20}$ straight, branched or cyclic divalent hydrocarbon group which may contain a heteroatom; $X^A$, $X^B$, $X^C$ and $X^D$ are each independently hydrogen, fluorine or trifluoromethyl, at least one of $X^A$, $X^B$, $X^C$ and $X^D$ being a substituent group other than hydrogen.

The resist composition may further comprise a compound having the formula (8) or (9).

Herein $R^{q1}$ is hydrogen or a $C_1$-$C_{40}$ straight, branched or cyclic monovalent hydrocarbon group which may contain a heteroatom, excluding the hydrocarbon group in which the hydrogen atom bonded to the carbon at α-position relative to the sulfo group is substituted by fluorine or fluoroalkyl, $R^{q2}$ is hydrogen or a $C_1$-$C_{40}$ straight, branched or cyclic monovalent hydrocarbon group which may contain a heteroatom, and $Mq^+$ is an onium cation.

The resist composition may further comprise an amine compound.

The resist composition may further comprise a surfactant which is insoluble or substantially insoluble in water and soluble in alkaline developer, and/or a surfactant which is insoluble or substantially insoluble in water and alkaline developer.

In a fourth aspect, the invention provides a pattern forming process comprising the steps of applying the resist composition defined above onto a substrate, prebaking to form a resist film, exposing a selected region of the resist film to KrF excimer laser, ArF excimer laser, EB or EUV through a photomask, baking, and developing the exposed resist film in a developer.

In one preferred embodiment, the developing step uses an alkaline aqueous solution as the developer, thereby forming a positive pattern in which an exposed region of the resist film is dissolved away and an unexposed region of the resist film is not dissolved.

In another preferred embodiment, the developing step uses an organic solvent as the developer, thereby forming a negative pattern in which an unexposed region of the resist film is dissolved away and an exposed region of the resist film is not dissolved.

The organic solvent is typically at least one solvent selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

In one preferred embodiment, the exposure step is carried out by immersion lithography while a liquid having a refractive index of at least 1.0 is held between the resist film and a projection lens. The process may further comprise the step of coating a protective film on the resist film prior to the exposure step, wherein immersion lithography is carried out while the liquid is held between the protective film and the projection lens.

Advantageous Effects of Invention

On use of the sulfonium salt as PAG, acid diffusion is suppressed. A resist composition comprising the sulfonium salt forms a pattern with improved lithography factors including EL, MEF and LWR when processed by lithography.

DESCRIPTION OF THE PREFERRED EMBODIMENTS

The singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. In chemical formulae, the broken line denotes a valence bond; Me stands for methyl, Et for ethyl, nBu for n-butyl, tBu for tert-butyl, Ac for acetyl, and Ph for phenyl.

The abbreviations have the following meaning.
DUV: deep ultraviolet
EUV: extreme ultraviolet
EB: electron beam
PAG: photoacid generator
PEB: post-exposure bake
LWR: line width roughness
MBF: mask error factor
EL: exposure latitude
DOP: depth of focus It is understood that for some structures represented by chemical formulae, there can exist enantiomers and diastereomers because of the presence of asymmetric carbon atoms. In such a case, a single formula collectively represents all such isomers. The isomers may be used alone or in admixture.

The term "high-energy radiation" is intended to encompass KrF excimer laser, ArF excimer laser, EB, and EUV.

Sulfonium Salt

The invention provides a sulfonium salt having the formula (1).

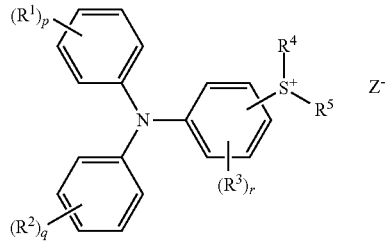

Herein $R^1$ to $R^3$ are each independently a $C_1$-$C_{20}$ straight, branched or cyclic monovalent hydrocarbon group which may contain a heteroatom. Suitable monovalent hydrocarbon groups include straight, branched or cyclic alkyl or oxoalkyl groups, straight, branched or cyclic alkenyl groups, aryl groups, aralkyl groups, and aryloxyalkyl groups.

Suitable alkyl groups include methyl, ethyl, propyl, isopropyl, n-butyl, s-butyl, t-butyl, t-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, tricyclo[$5.2.1.0^{2,6}$]decanyl, adamantyl and adamantylmethyl. Suitable oxoalkyl groups are 2-oxocyclopentyl, 2-oxocyclohexyl, 2-oxopropyl, 2-oxoethyl, 2-cyclopentyl-2-oxoethyl, 2-cyclohexyl-2-oxoethyl, and 2-(4-methylcyclohexyl)-2-oxoethyl.

Suitable alkenyl groups include vinyl, allyl, propenyl, butenyl, hexenyl, and cyclohexenyl.

Suitable aryl groups include phenyl, naphthyl, thienyl, 4-hydroxyphenyl, alkoxyphenyl groups (e.g., 4-methoxyphenyl, 3-methoxyphenyl, 2-methoxyphenyl, 4-ethoxyphenyl, 4-t-butoxyphenyl, 3-t-butoxyphenyl), alkylphenyl groups (e.g., 2-methylphenyl, 3-methylphenyl, 4-methylphenyl, 4-ethylphenyl, 4-t-butylphenyl, 4-n-butylphenyl, 2,4-dimethylphenyl), alkylnaphthyl groups (e.g., methylnaphthyl, ethylnaphthyl), alkoxynaphthyl groups (e.g., methoxynaphthyl, ethoxynaphthyl, n-propoxynaphthyl, n-butoxynaphthyl), dialkylnaphthyl groups (e.g., dimethylnaphthyl, diethylnaphthyl), and dialkoxynaphthyl groups (e.g., dimethoxynaphthyl, diethoxynaphthyl). Suitable aralkyl groups include benzyl, 1-phenylethyl, and 2-phenylethyl. Suitable aryloxyalkyl groups are 2-aryl-2-oxoethyl groups including 2-phenyl-2-oxoethyl, 2-(1-naphthyl)-2-oxoethyl, 2-(2-naphthyl)-2-oxoethyl.

Also included are the foregoing groups in which at least one hydrogen atom is substituted by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl radical, cyano radical, carbonyl radical, ether radical, ester radical, sulfonic acid ester radical, carbonate radical, lactone ring, sultone ring, carboxylic acid anhydride or haloalkyl radical.

A pair of $R^1$ and $R^2$, $R^1$ and $R^3$, or $R^2$ and $R^3$ may bond together to form a ring with the benzene rings to which they are attached and the nitrogen atom therebetween. Examples of the ring structure thus formed are shown below, but not limited thereto.

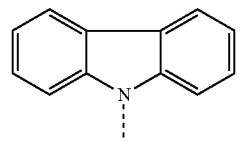

-continued

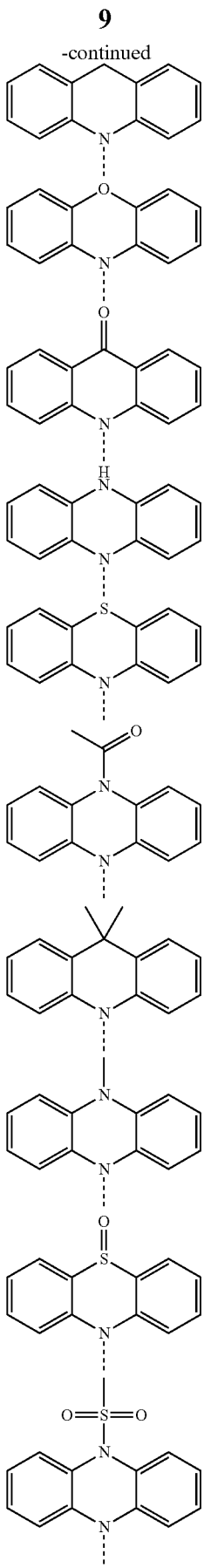

-continued

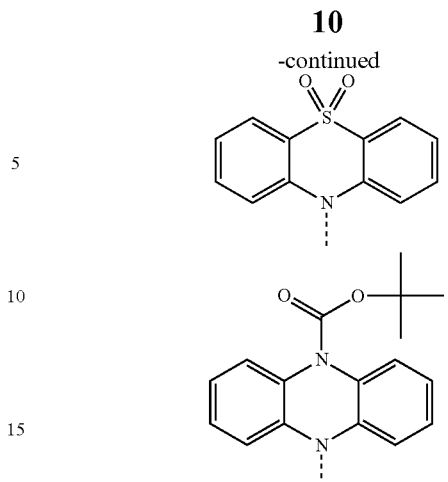

In formula (1), p and q are each independently an integer of 0 to 5. In view of the availability of starting reactants, each of p and q is preferably an integer of 0 to 3, more preferably 0 or 1. The substitution position of $R^1$ or $R^2$ is preferably para relative to the nitrogen atom. With the substituent at para-position, the influence of enhanced steric hindrance around the nitrogen atom is reduced, and as a result, a lowering of acid diffusion suppressing effect of nitrogen atom by the introduction of the substituent is suppressed. Also the basicity of nitrogen atom may be adjusted by altering the number of substituents, the position of substitution, and the type of substituents (electron donative or attractive group).

In formula (1), r is an integer of 0 to 4. In view of the availability of starting reactants and reactivity with sulfoxide, r is preferably an integer of 0 to 2. The substitution position of $R^3$ is preferably ortho or meta relative to the nitrogen atom. If the substituent group is at para-position, the reaction with sulfoxide may become complicated. Also the basicity of nitrogen atom may be adjusted by altering the number of substituents, the position of substitution, and the type of substituents (electron donative or attractive group).

It is believed that when the basicity of nitrogen atom is adjusted by the above means such that the conjugated acid of triarylamine may have an acidity value close to the acidity of strong acid generated upon exposure, the acid diffusion suppressing effect due to proton exchange reaction (to be described later) can be enhanced. Because of approximate acidity values, the equilibrium of proton exchange reaction is not biased to one side, and efficient proton exchange reaction takes place within the film.

When p, q and/or r is 2 or more, a plurality of groups $R^1$, $R^2$ or $R^3$ may be the same or different and bond together to form a ring with the carbon atoms on the benzene ring to which they are attached. Examples of the ring structure thus formed are shown below, but not limited thereto.

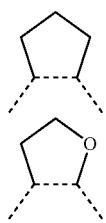

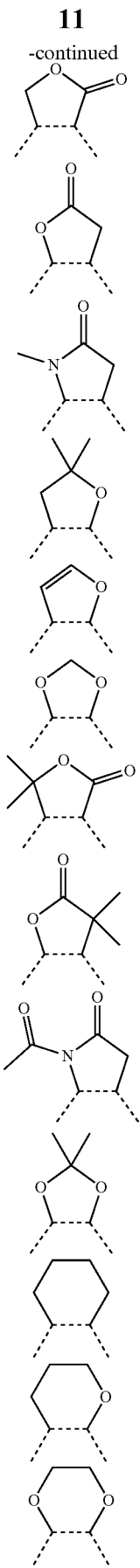
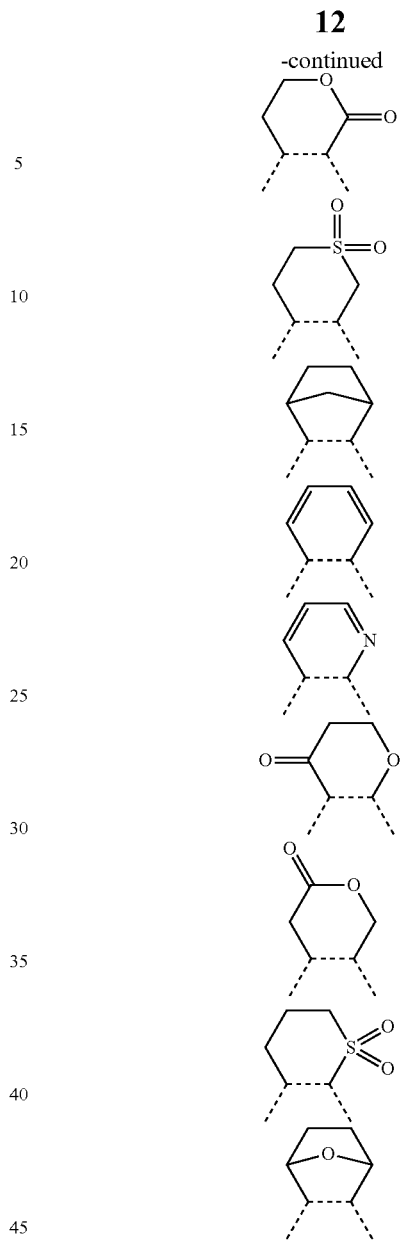

Herein the broken lines represent a portion of benzene ring.

In the embodiment wherein a pair of R¹ and R², R¹ and R³, or R² and R³ bond together to form a ring with the benzene rings to which they are attached and the nitrogen atom therebetween, preferably the sulfonium moiety bonds with a carbon atom on the benzene ring which does not participate in the ring formation. That is, preferably R¹ and R² bond together to form a ring. If the sulfonium moiety bonds with the benzene ring which participates in the ring formation, this may invite degradation of sensitivity. It is believed that the cause resides in that the rotation of the benzene ring with which the sulfonium moiety bonds is prevented, and the acid generating reaction upon exposure is thus inhibited. Also in view of stability and ease of synthesis of the cation, preferably the sulfonium moiety bonds at the para-position relative to the nitrogen atom. If the sulfonium moiety bonds at the meta-position relative to the nitrogen atom, then the resonance effect due to isolated electron pair of the nitrogen atom is not obtained, inviting instability. If the sulfonium moiety bonds at the ortho-position relative to the nitrogen atom, the steric hindrance with the adjoining benzene ring may cause instability.

In formula (1), $R^4$ and $R^5$ are each independently a $C_1$-$C_{30}$ straight, branched or cyclic monovalent hydrocarbon group which may contain a heteroatom. Examples of the monovalent hydrocarbon group are as exemplified above for $R^1$ to $R^3$.

Also a pair of $R^4$ and $R^5$ may bond together to form a ring with the sulfur atom to which they are attached. In this case, the sulfonium salt may form a structure having the formula (2).

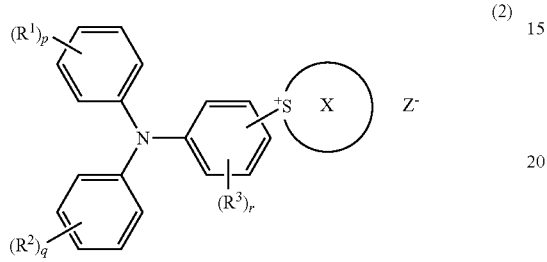

(2)

In formula (2), $R^1$ to $R^3$, p, q, r and $Z^-$ are as defined above. The ring X is a $C_2$-$C_{30}$ cyclic hydrocarbon group which contains the sulfur atom as a part of the ring and may contain a heteroatom. The ring X is preferably a 3 to 7-membered ring, more preferably 5 to 7-membered ring, and even more preferably 5 or 6-membered ring. The preferred structures of the ring X are represented by the following formulae.

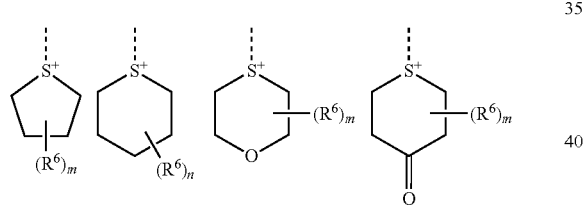

Herein $R^1$ is a $C_1$-$C_{20}$ straight, branched or cyclic monovalent hydrocarbon group which may contain a heteroatom, m is an integer of 0 to 8, and n is an integer of 0 to 10. When m or n is 2 or more, a plurality of groups $R^6$ may be the same or different and may bond together to form a ring.

Where the ring X is a cyclic alkylsulfonium, a cation having a good balance of transparency and sensitivity is obtainable because of high transparency inherent to the alkylsulfonium structure and a high sensitivity due to ease of decomposition. Also the 5 to 7-membered ring structure ensures high stability to a variety of quenchers. This is probably because the 5 to 7-membered ring structure experiences a small ring distortion by the bond angle of the sulfonium cation moiety.

Exemplary structures of the ring X are shown below, but not limited thereto.

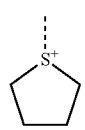

-continued

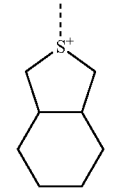

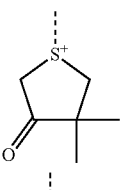

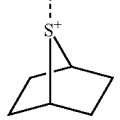

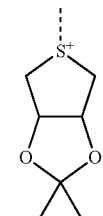

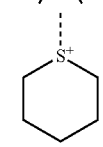

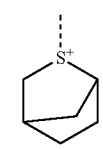

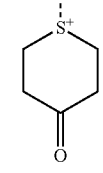

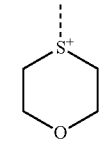

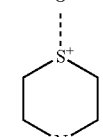

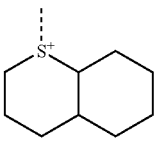

-continued
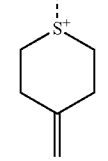
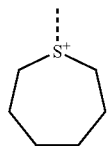
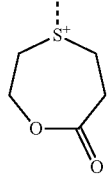
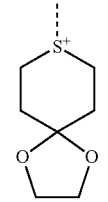
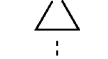
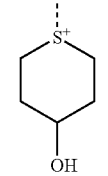
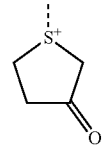
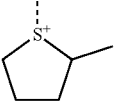
-continued
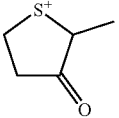
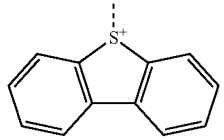
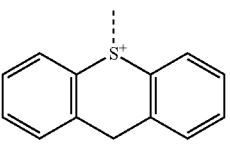
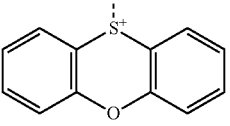
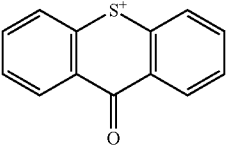
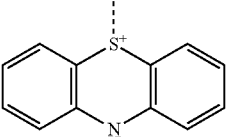
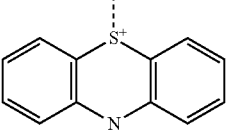
Examples of the cation moiety in the sulfonium salt having formula (1) are shown below, but not limited thereto.
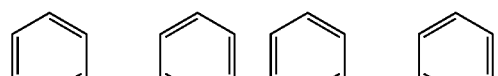
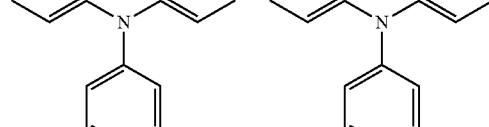
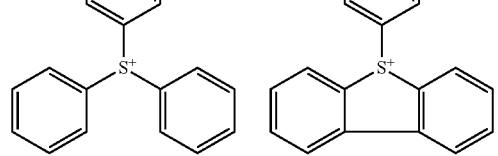

-continued
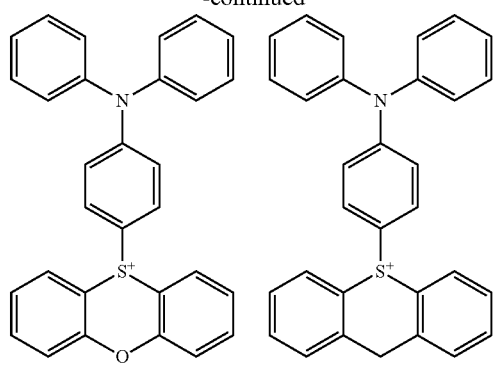
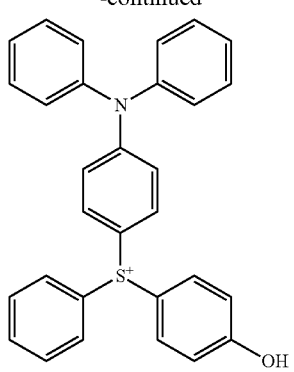
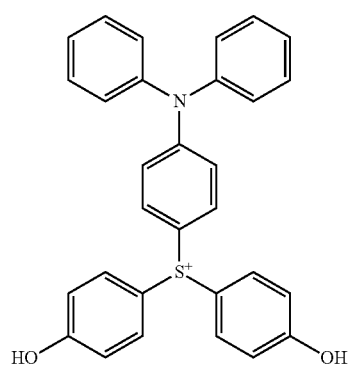
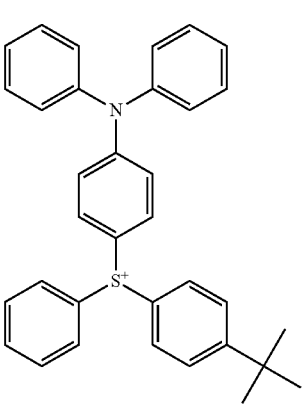
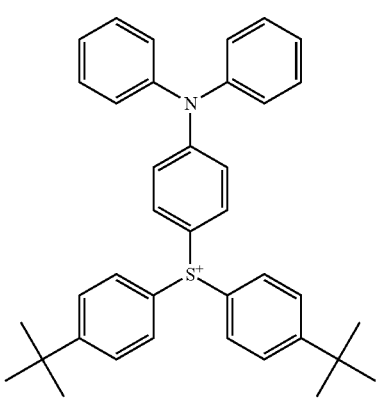
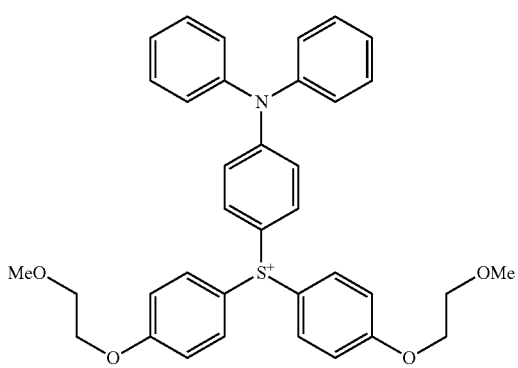
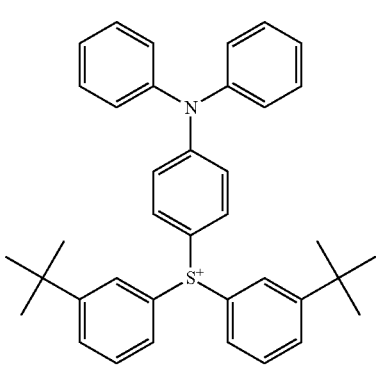

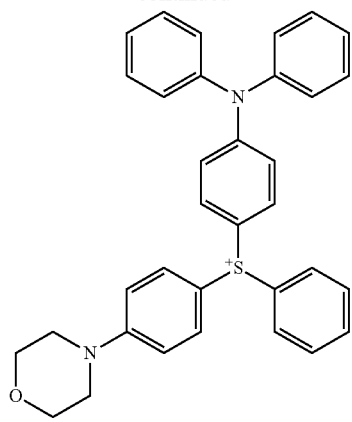
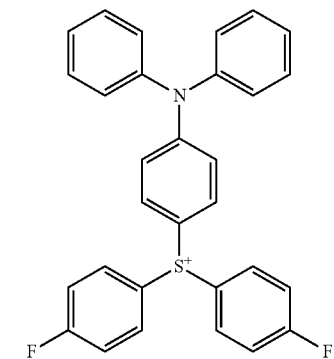
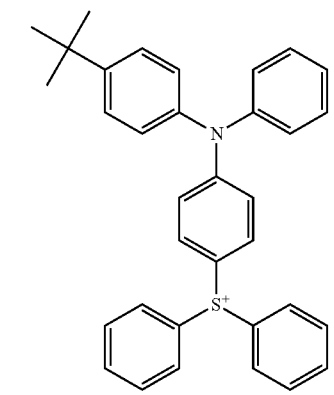
Examples of the cation moiety in the sulfonium salt having formula (2) are shown below, but not limited thereto.
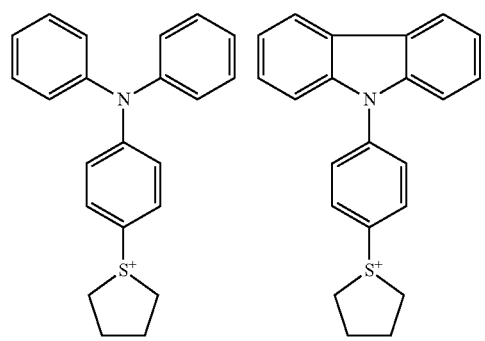
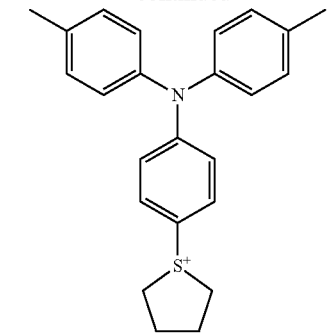
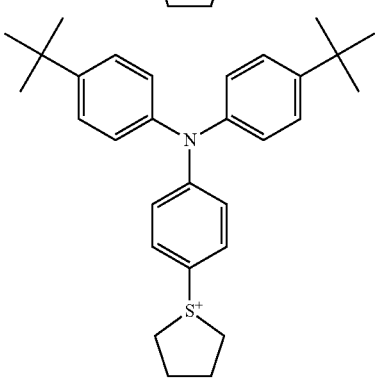
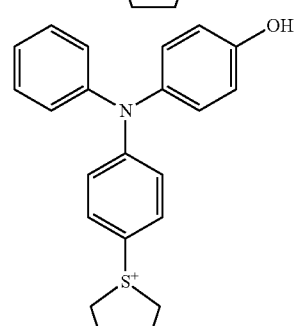
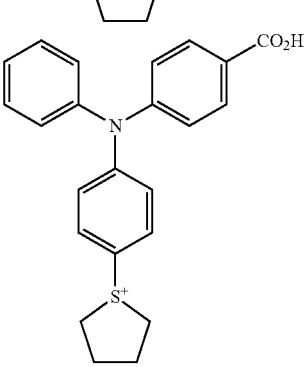
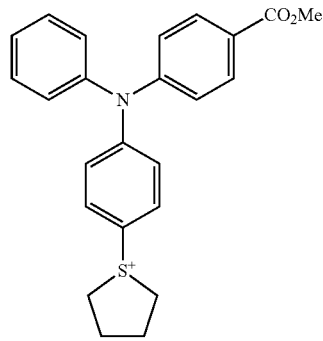

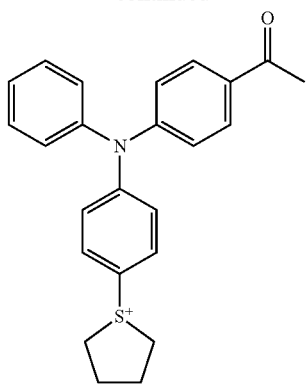
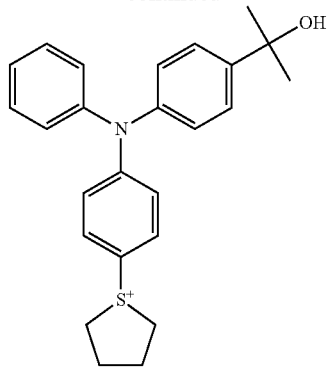
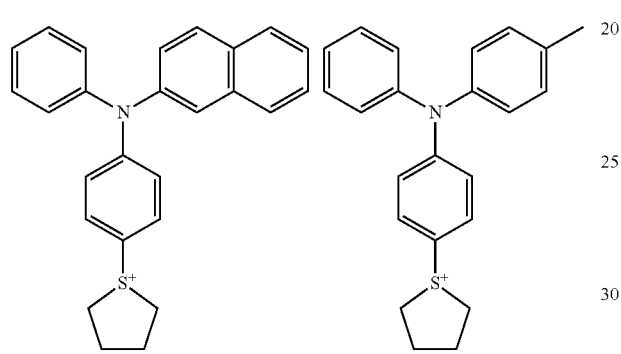
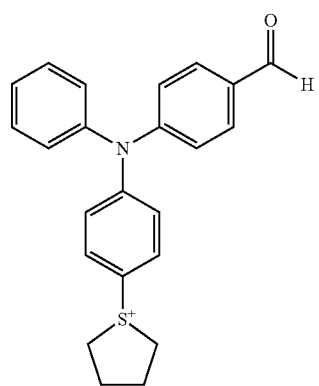
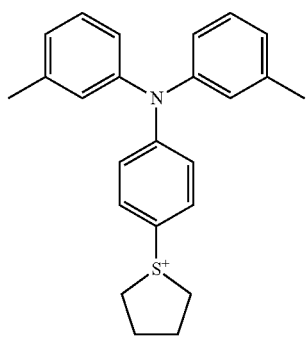
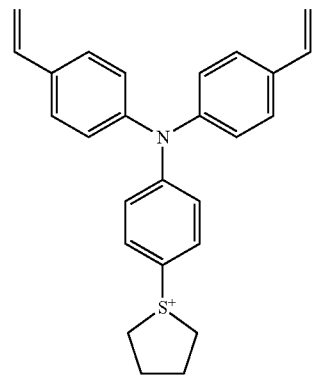
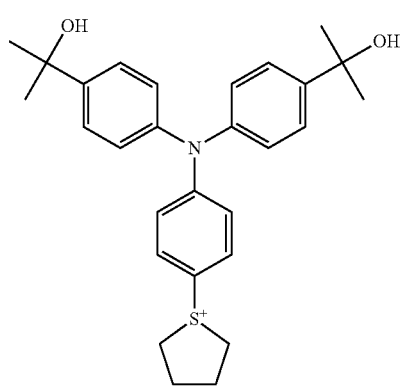
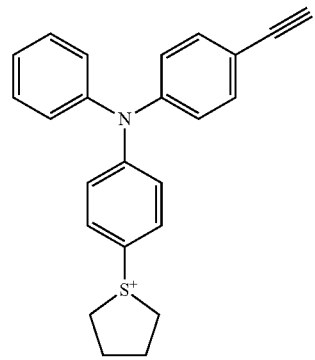

23
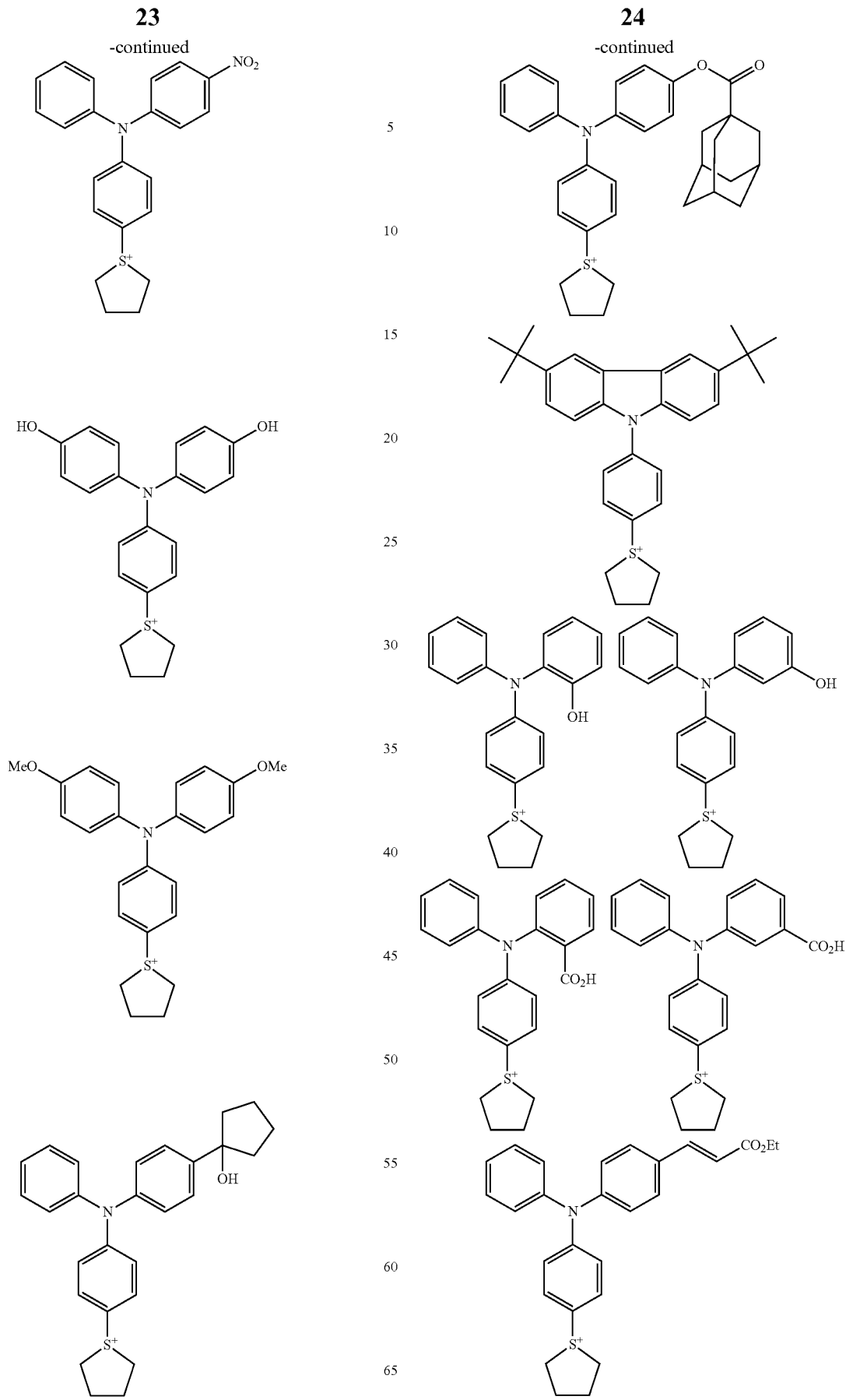

25
-continued
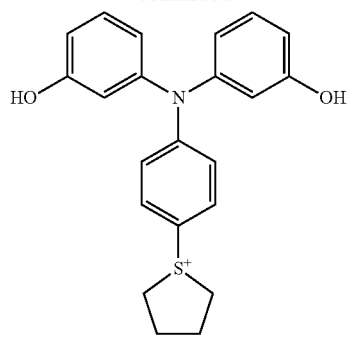
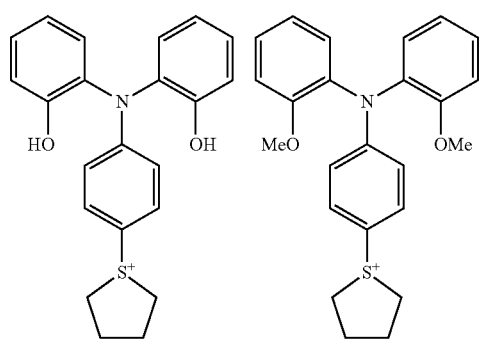
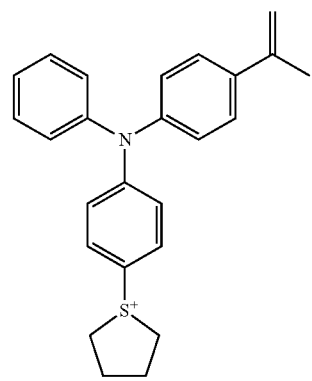
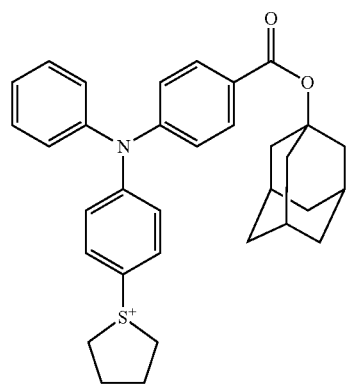
26
-continued
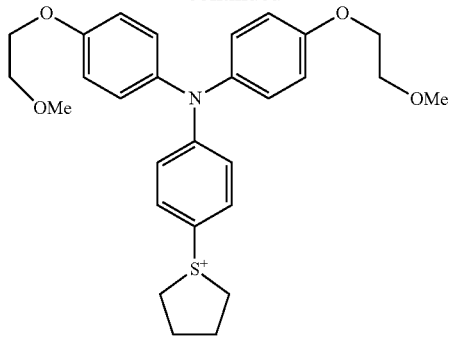
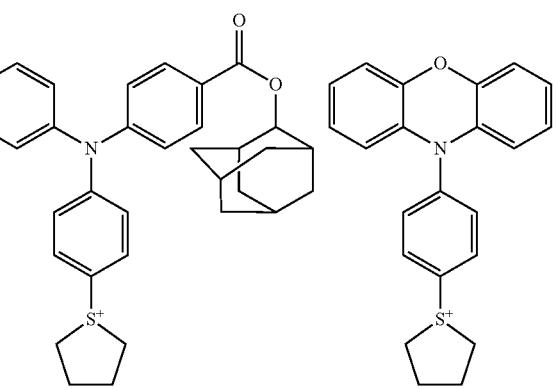
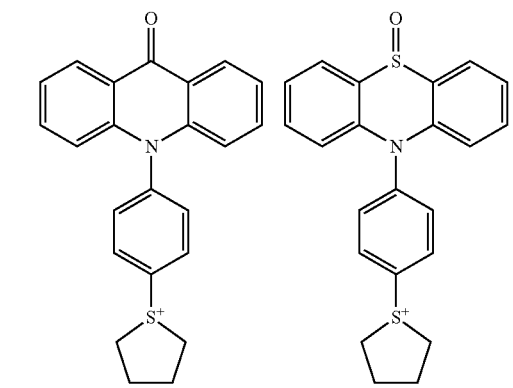
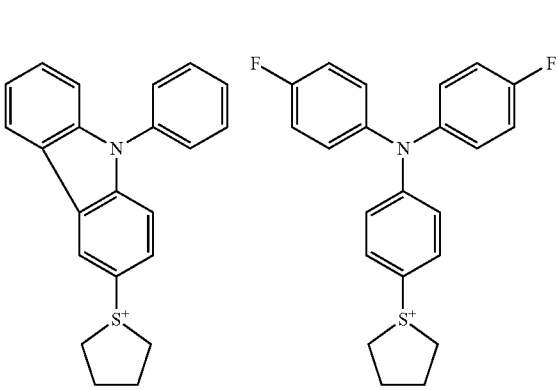

-continued
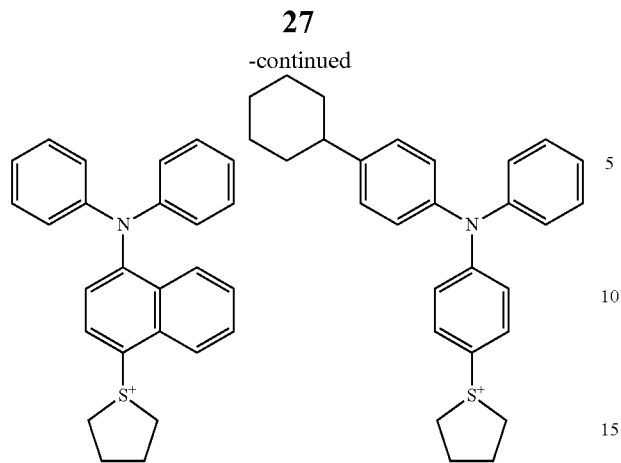
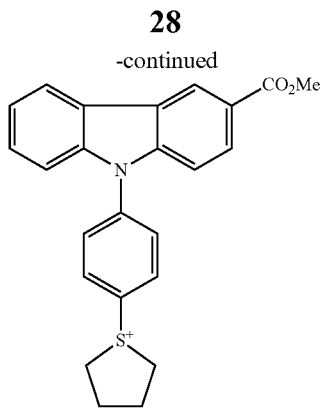
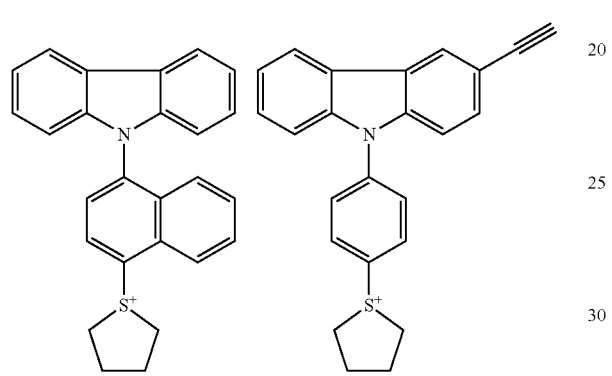
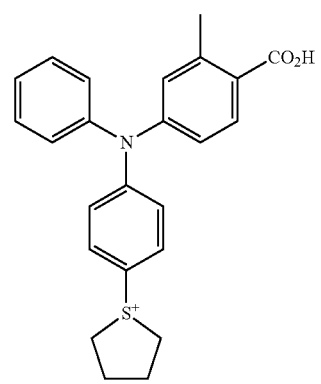
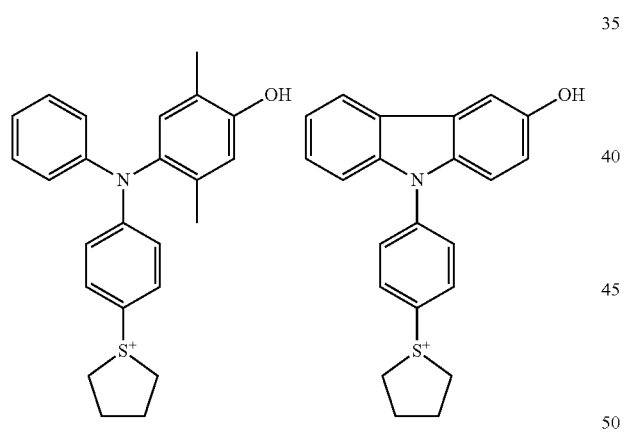
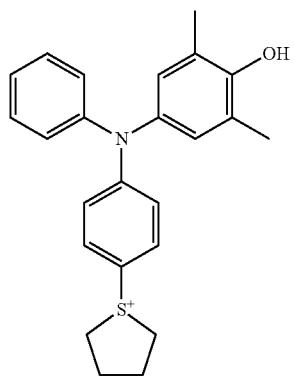
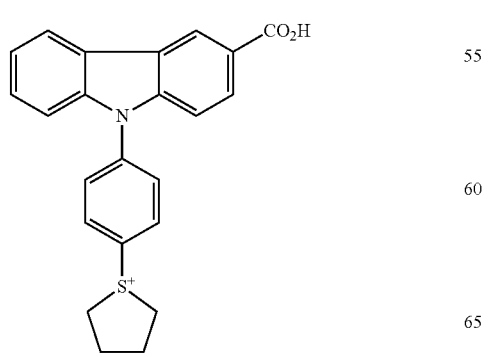
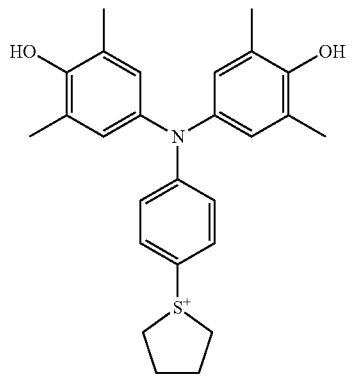

-continued
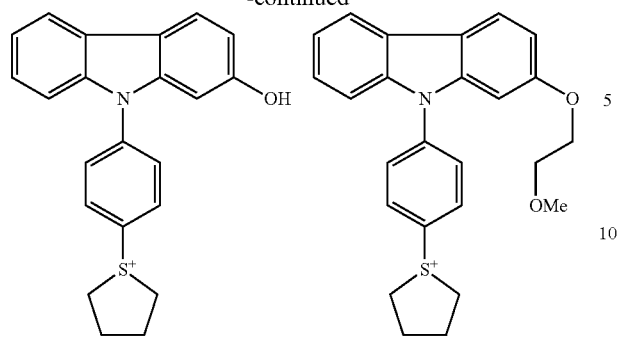
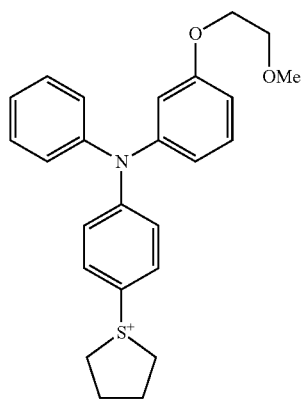
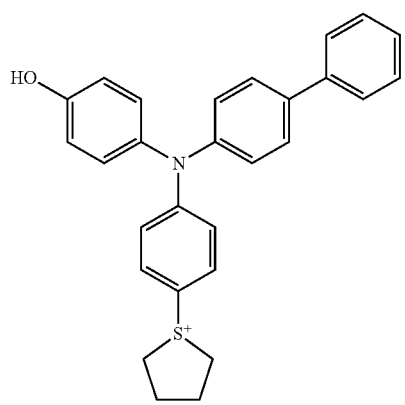
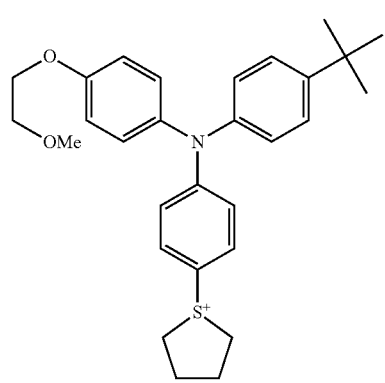
-continued
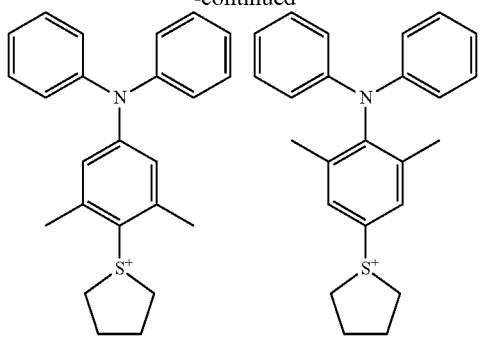
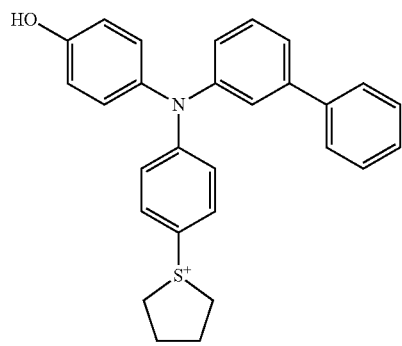
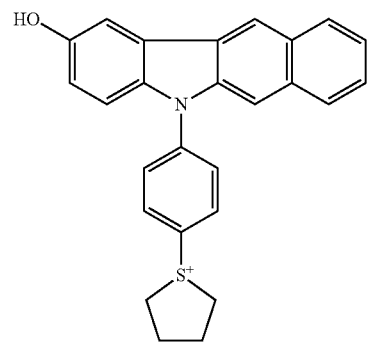
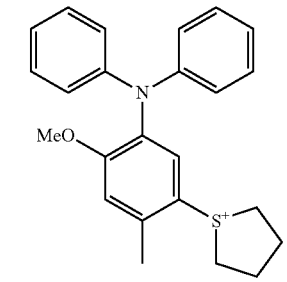
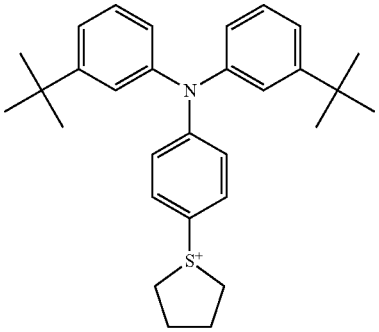

-continued
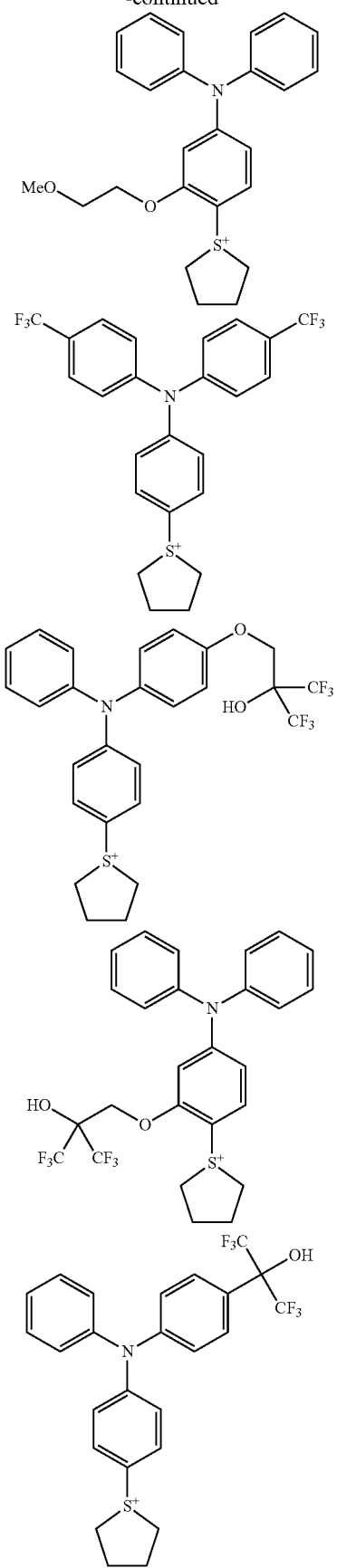
-continued
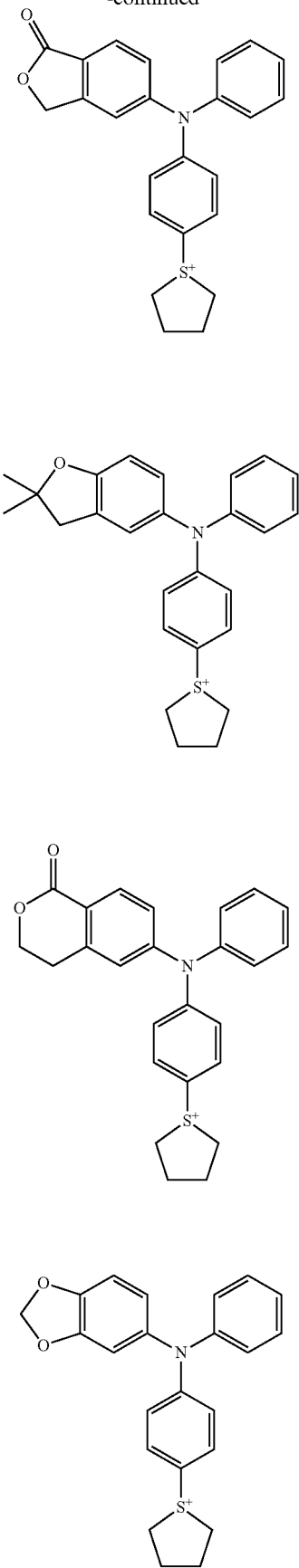

33
-continued
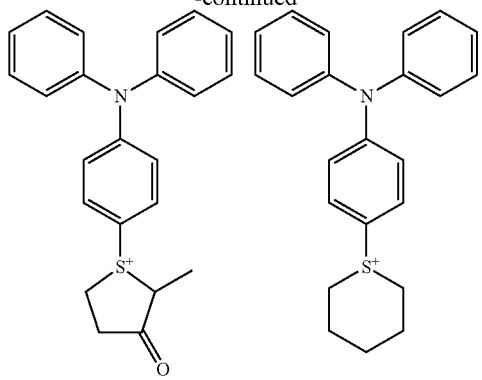
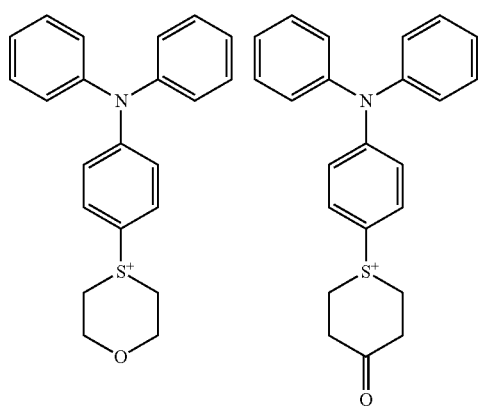
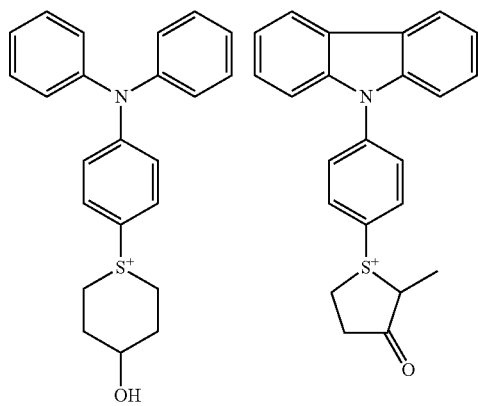
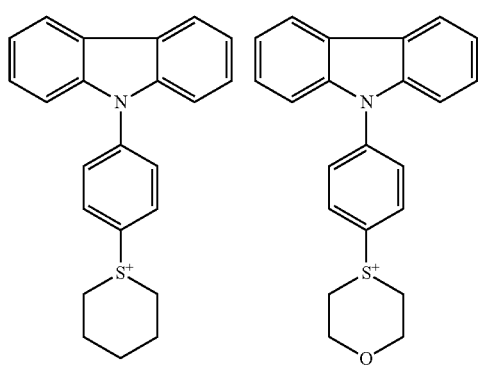
34
-continued
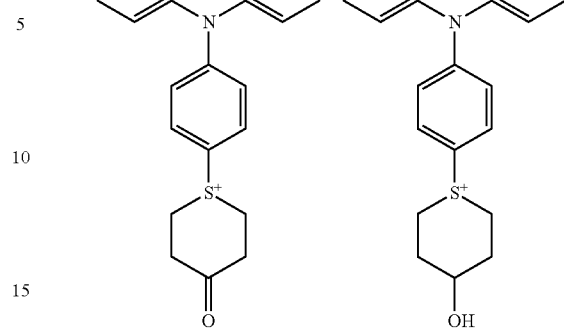
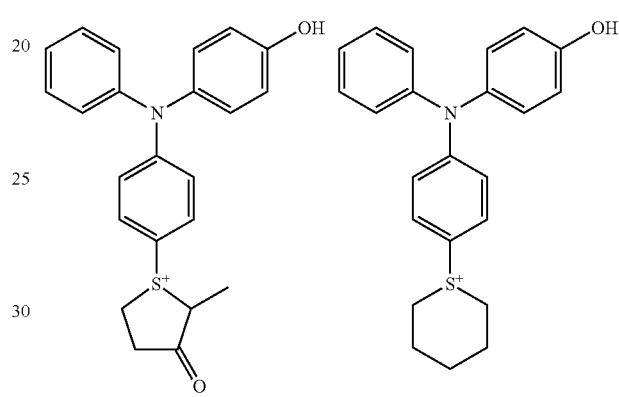
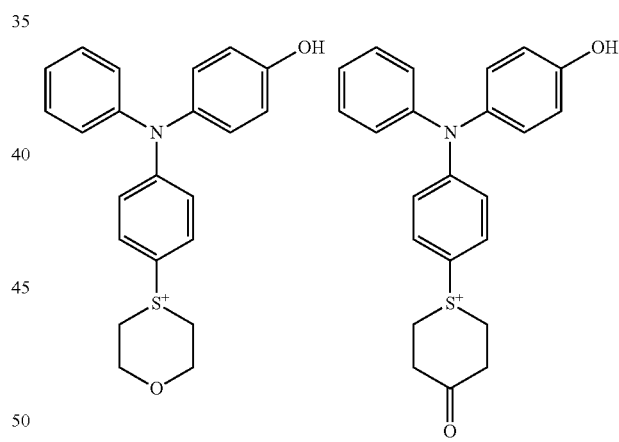
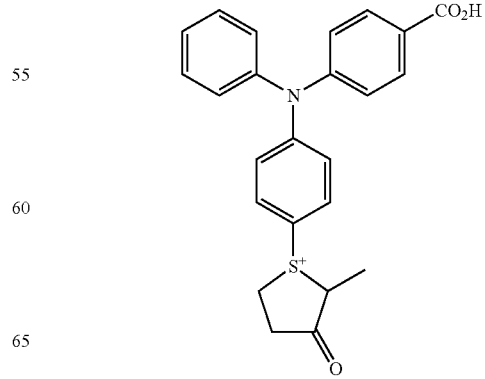

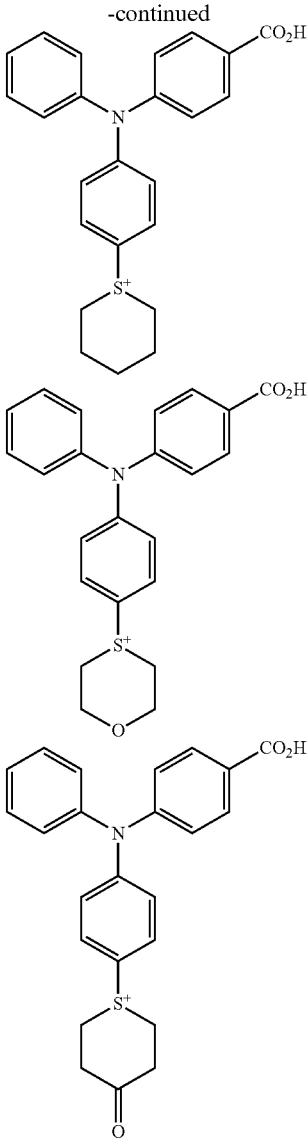

In formulae (1) and (2), $Z^-$ is a monovalent anion. Preferably $Z^-$ is an anion derived from an alkanesulfonic acid, fluoroalkanesulfonic acid, alkanecarboxylic acid, fluoroalkanecarboxylic acid, imide acid (imidic acid) or methide acid, more preferably an anion derived from an alkanesulfonic acid, fluoroalkanesulfonic acid, imide acid or methide acid.

Suitable alkanesulfonic acid anions include methansulfonate, 4-methylphenylsulfonate, 2,4,6-triisopropylsulfonate, 2,4,6-tricyclohexylphenylsulfonate, and 10-camphorsulfonate.

Suitable fluoroalkanesulfonic acid anions include trifluoromethanesulfonate, pentafluoroethanesulfonate and nonafluorobutanesulfonate. Suitable alkanecarboxylic acid anions include benzoate and 4-tert-butylbenzoate. Suitable fluoroalkanecarboxylic acid anions include trifluoroacetate, pentafluoropropionate, and 3,3,3-trifluoro-2-hydroxy-2-trifluoromethylpropionate. Suitable imide acid anions include bis(trifluoromethanesulfonyl)imide, bis(nonafluorobutanesulfonyl)imide, and N,N-hexafluoro-1,3-disulfonylimide. Typical of the methide acid anion is tris(trifluoromethanesulfonyl)methide.

More preferably $Z^-$ is an anion having the formula (3).

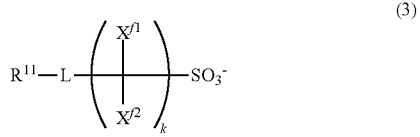

(3)

In formula (3), $R^{11}$ is a $C_1$-$C_{40}$ straight, branched or cyclic monovalent hydrocarbon group which may contain a heteroatom. Examples of the monovalent hydrocarbon group are as exemplified above for $R^1$ to $R^3$. Also included are monovalent hydrocarbon groups of steroid structure and monovalent hydrocarbon groups of steroid structure which is partially modified with a substituent, such as dehydrocholic acid structures.

In formula (3), L is a single bond or a divalent linking group. L is preferably a single bond, ether, ester, sulfonic acid ester, amide, carbonate, or carbamate group, with a single bond, ether group and ester group being more preferred.

In formula (3), $X^{f1}$ and $X^{f2}$ are each independently hydrogen, fluorine or a fluorinated alkyl group, preferably hydrogen, fluorine or trifluoromethyl, and k is an integer of 0 to 4, preferably 1 to 4, and more preferably 1 to 3.

Of the anions having formula (3), those anions having the formulae (4) and (5) are more preferred.

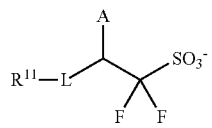

(4)

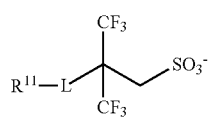

(5)

Herein $R^{11}$ and L are as defined above, and A is hydrogen or trifluoromethyl.

Examples of the anion having formula (3), (4) or (5) are shown below, but not limited thereto. Herein A is as defined above.

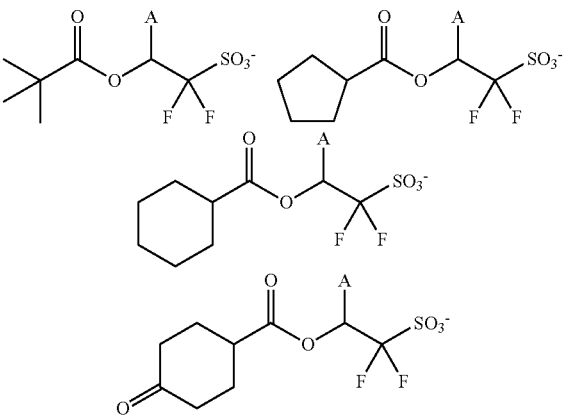

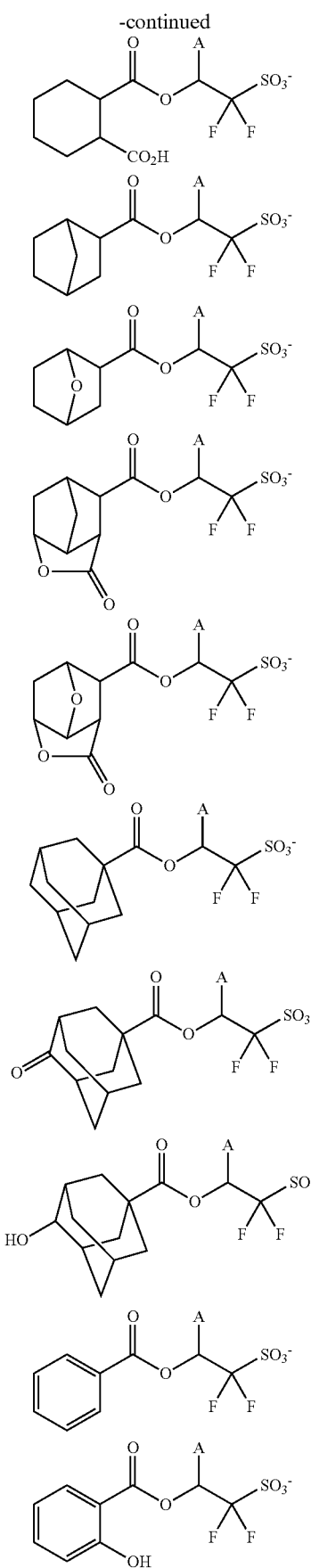
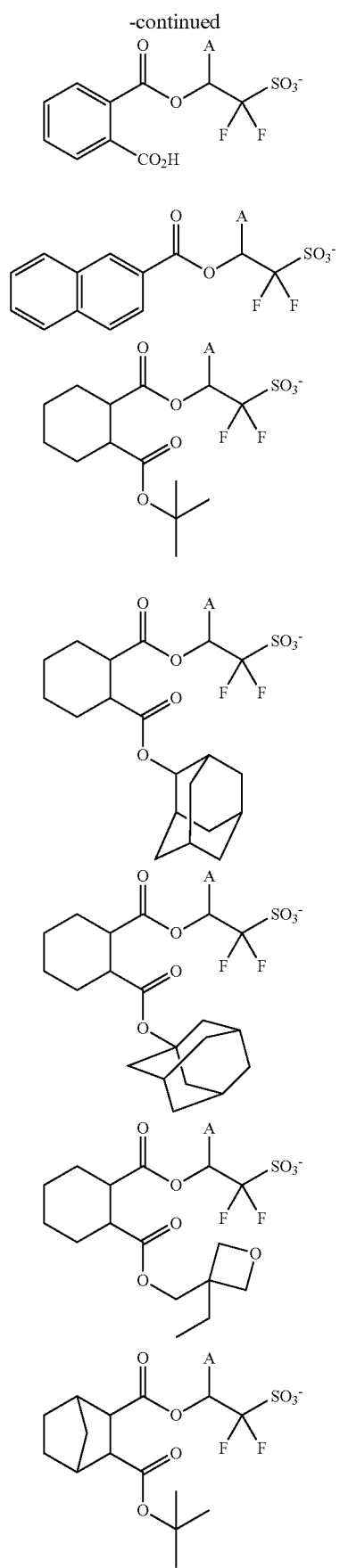

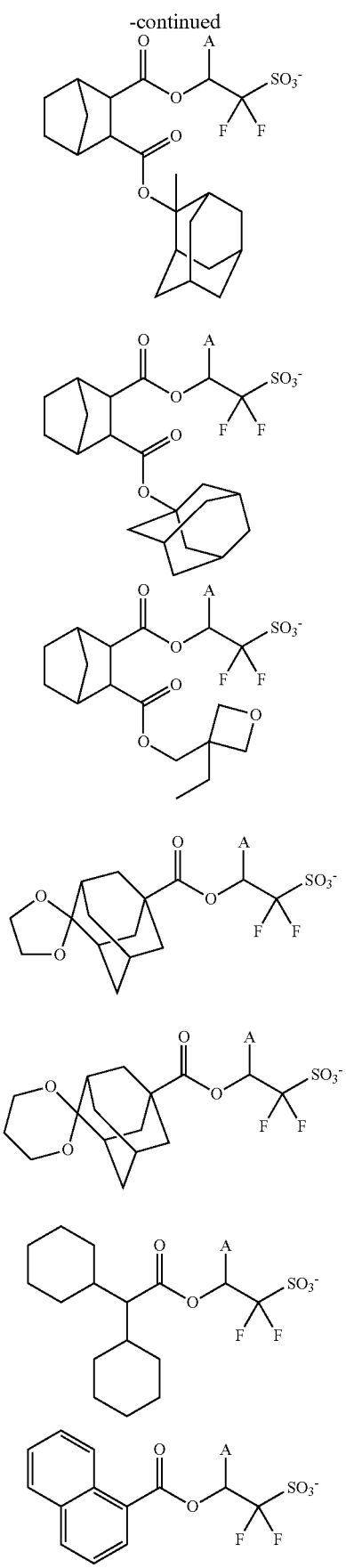
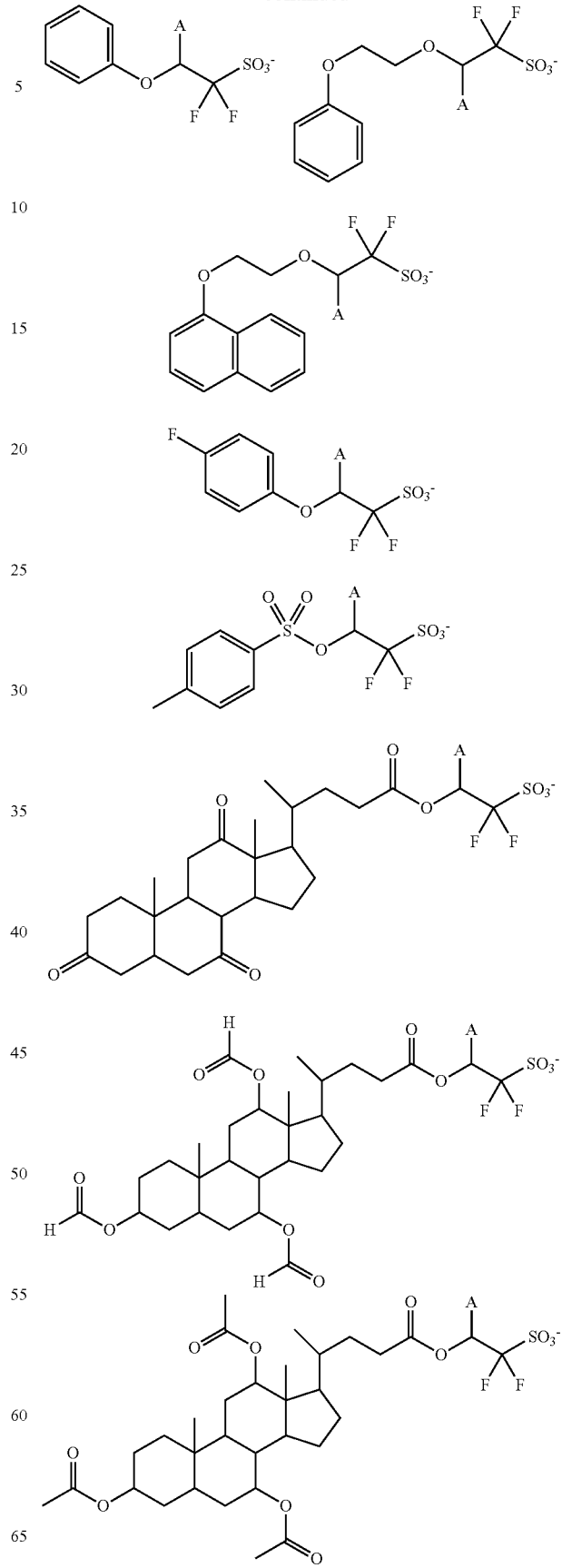

41
-continued
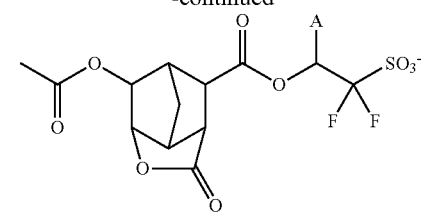
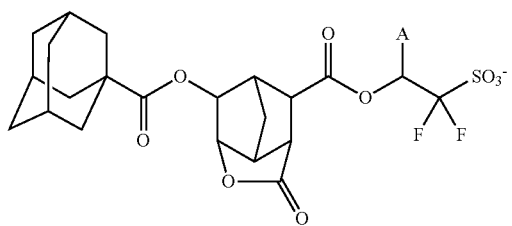
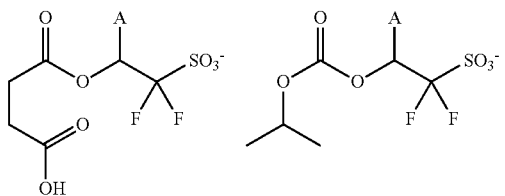
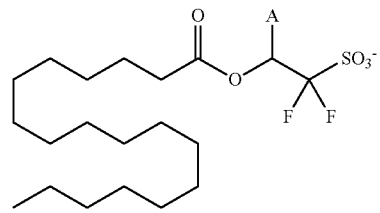
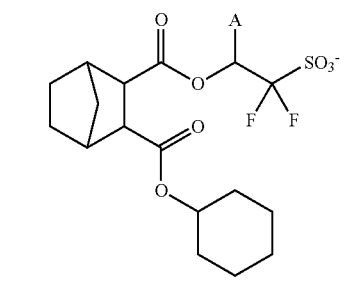
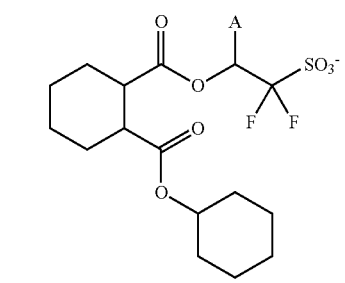
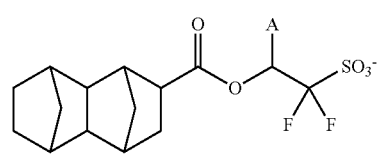
42
-continued
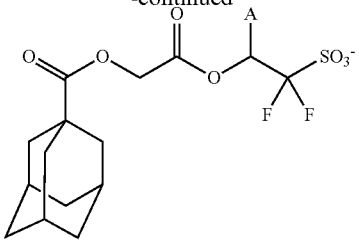
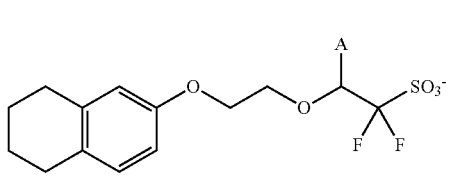
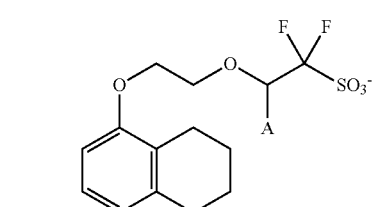
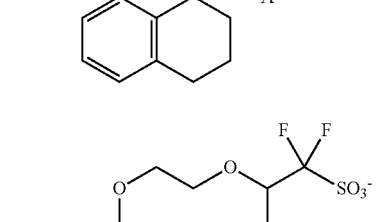
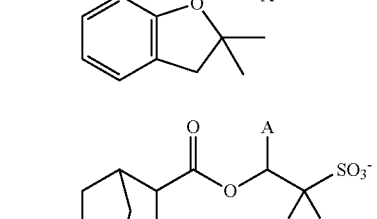
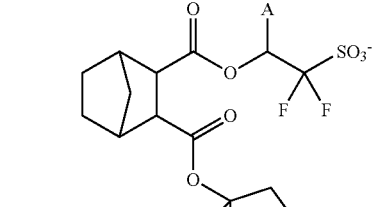
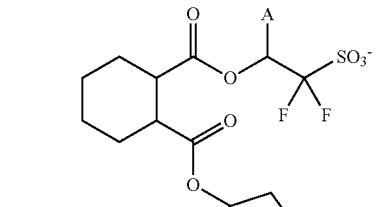
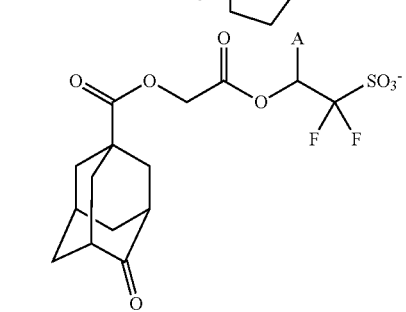

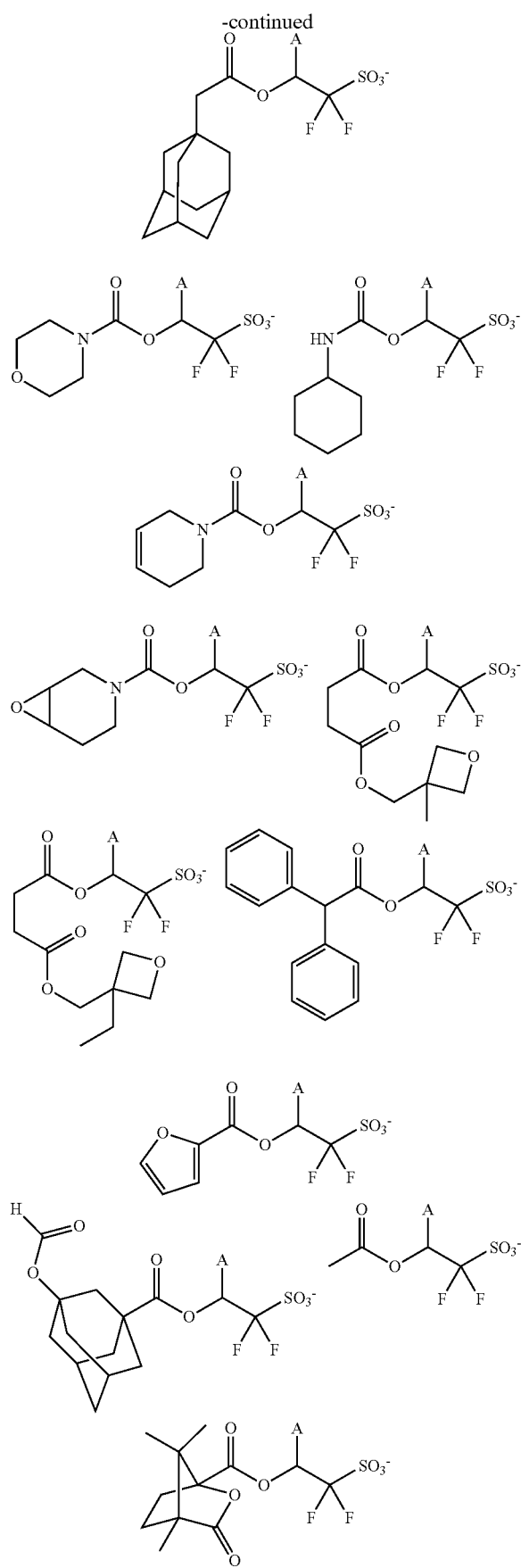
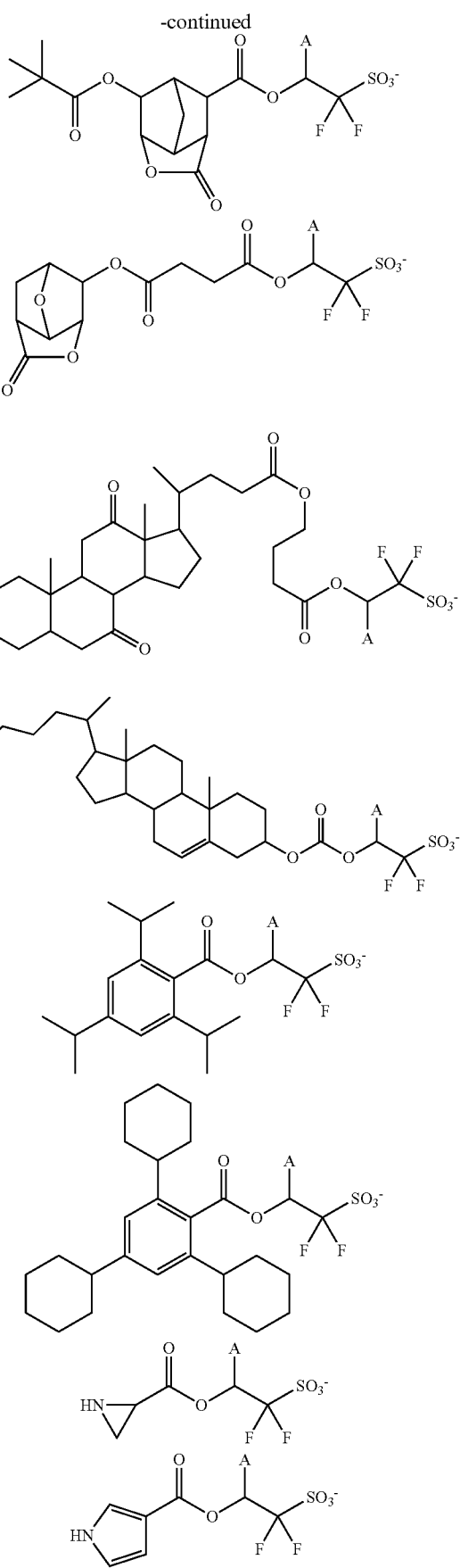

-continued
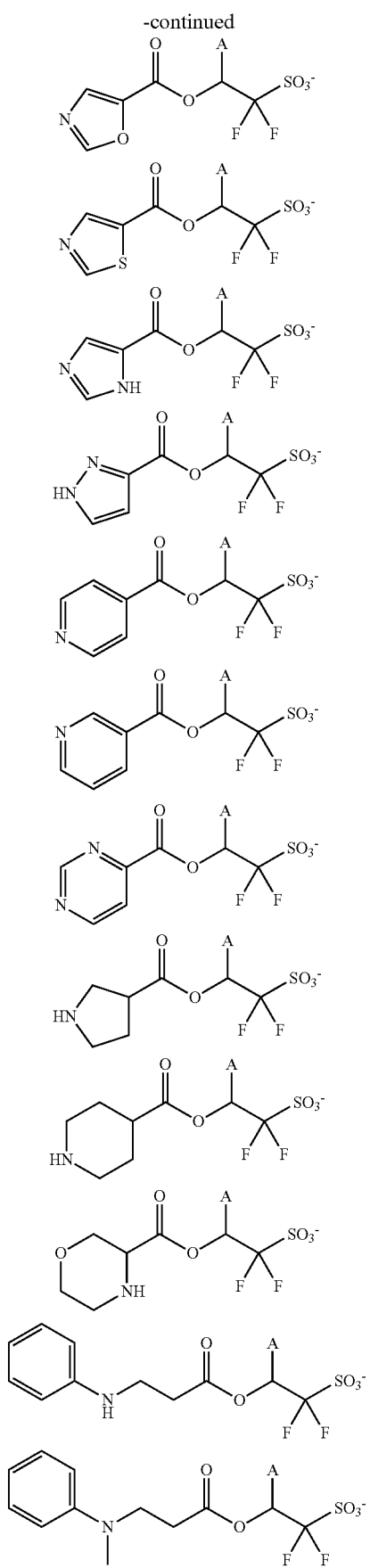
-continued
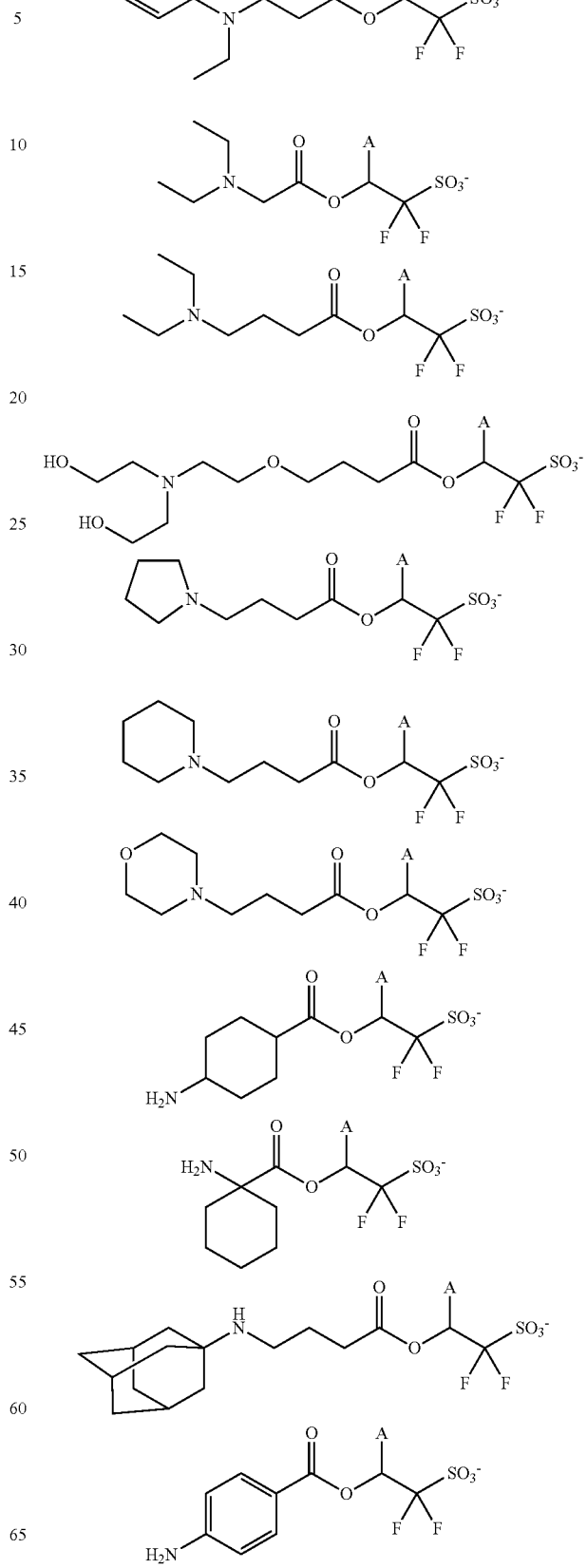

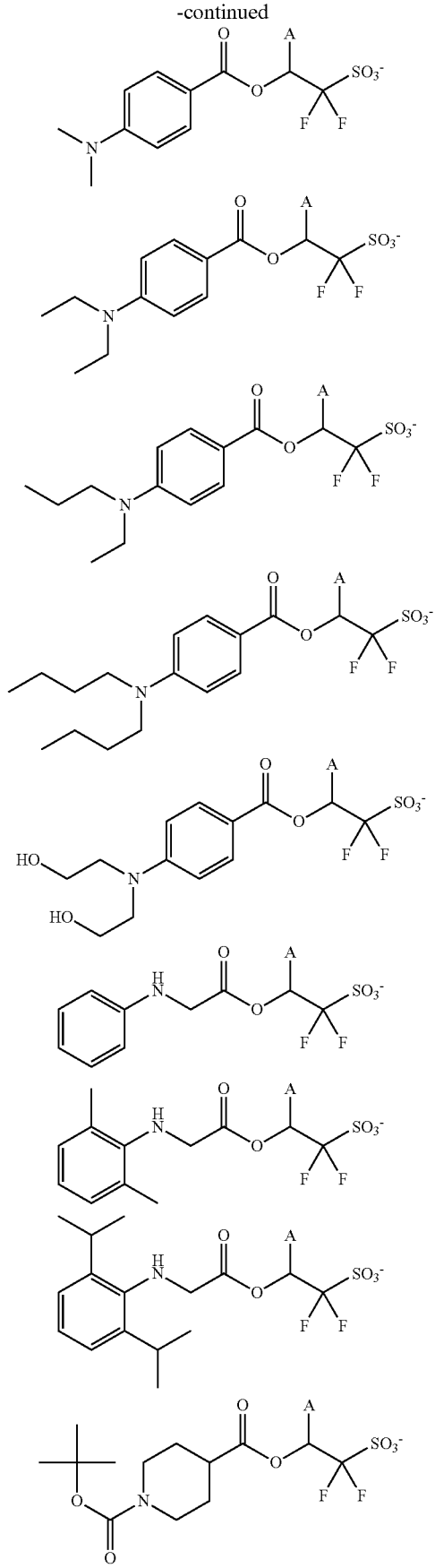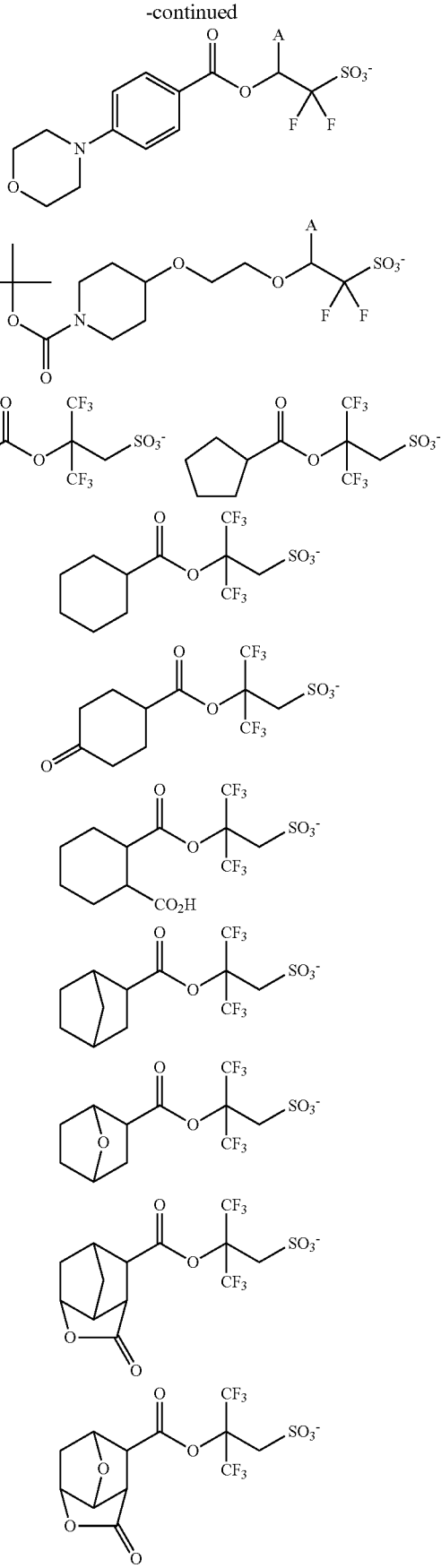

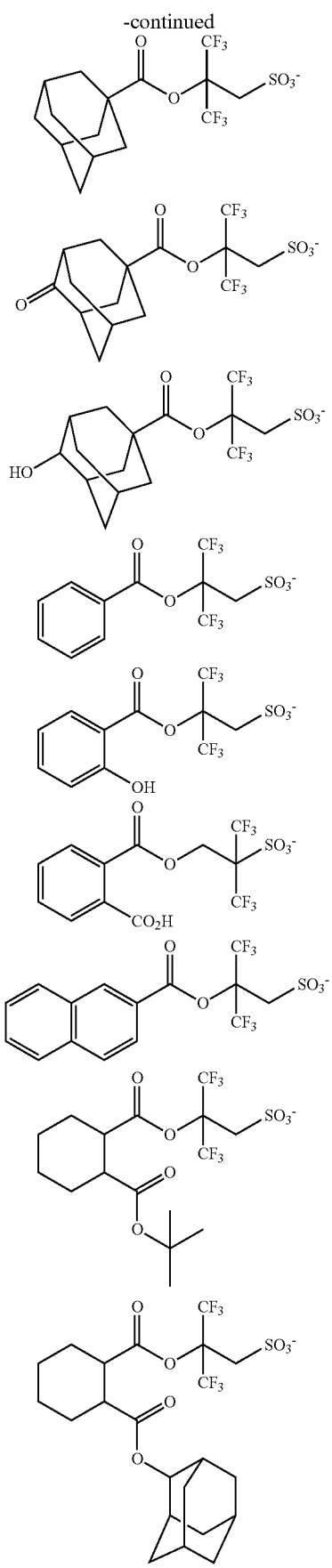
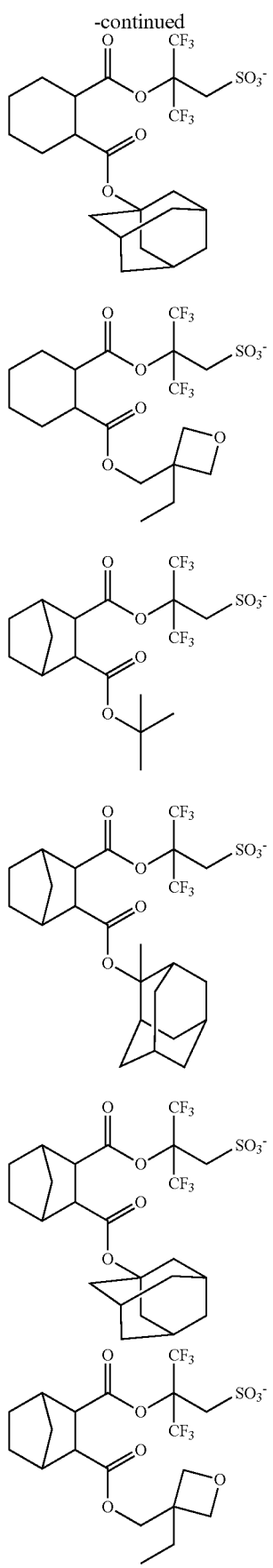

-continued
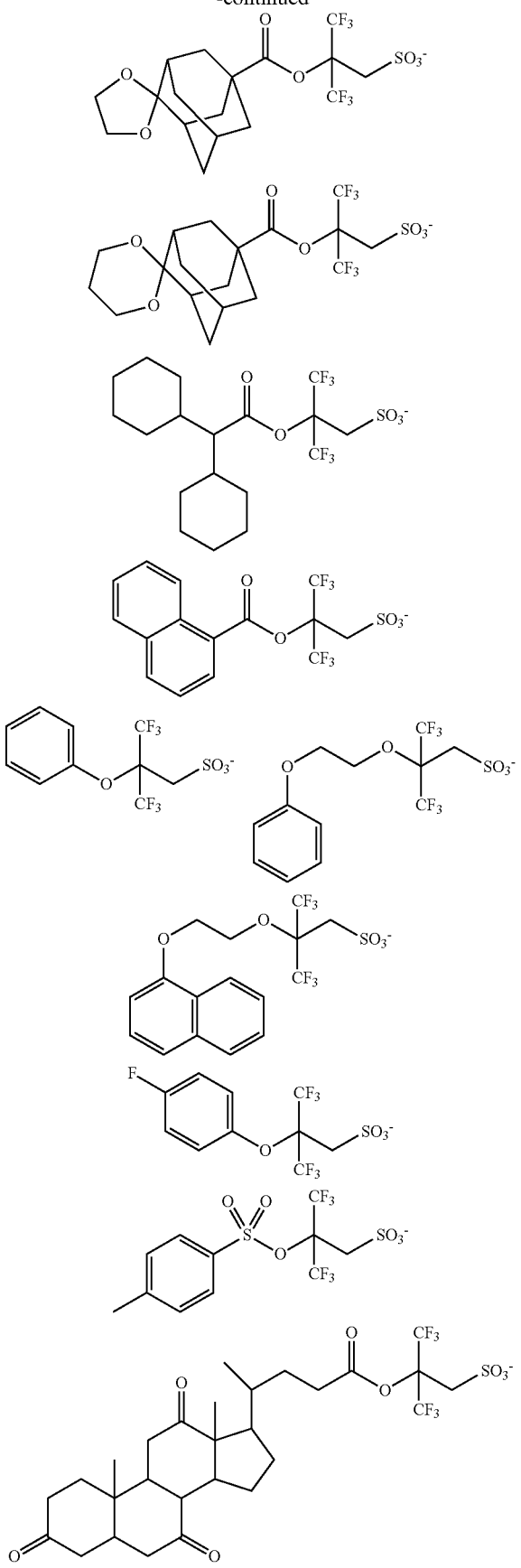
-continued
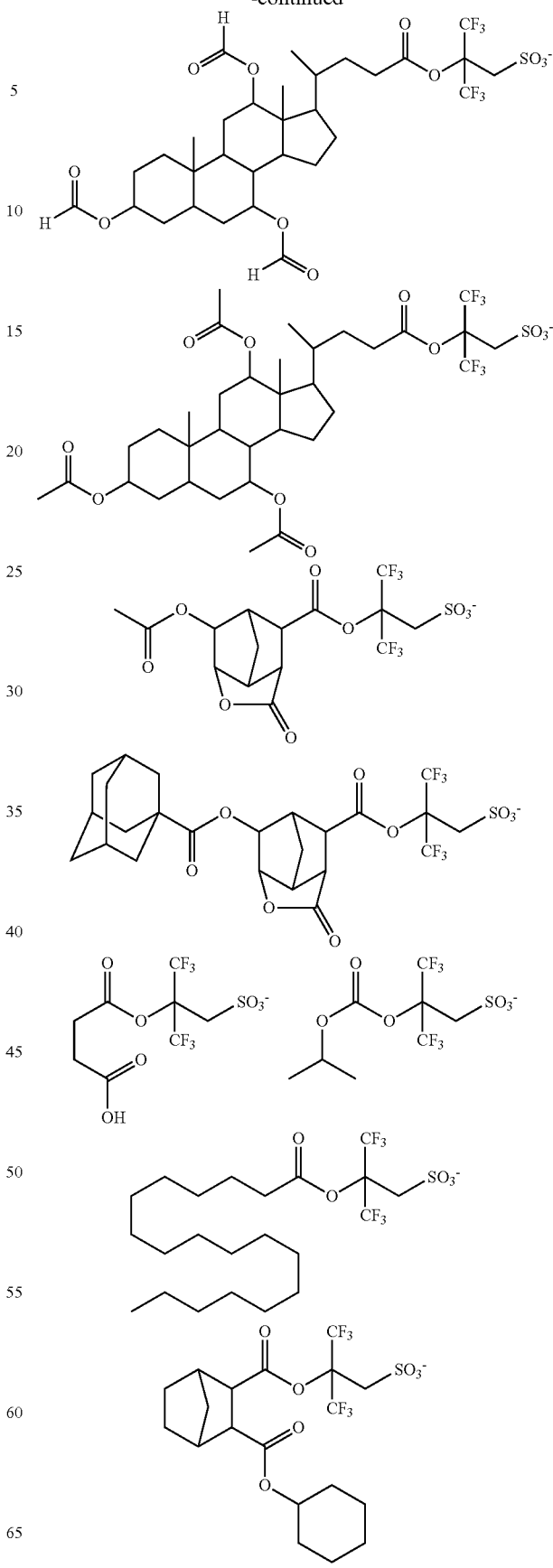

53
-continued
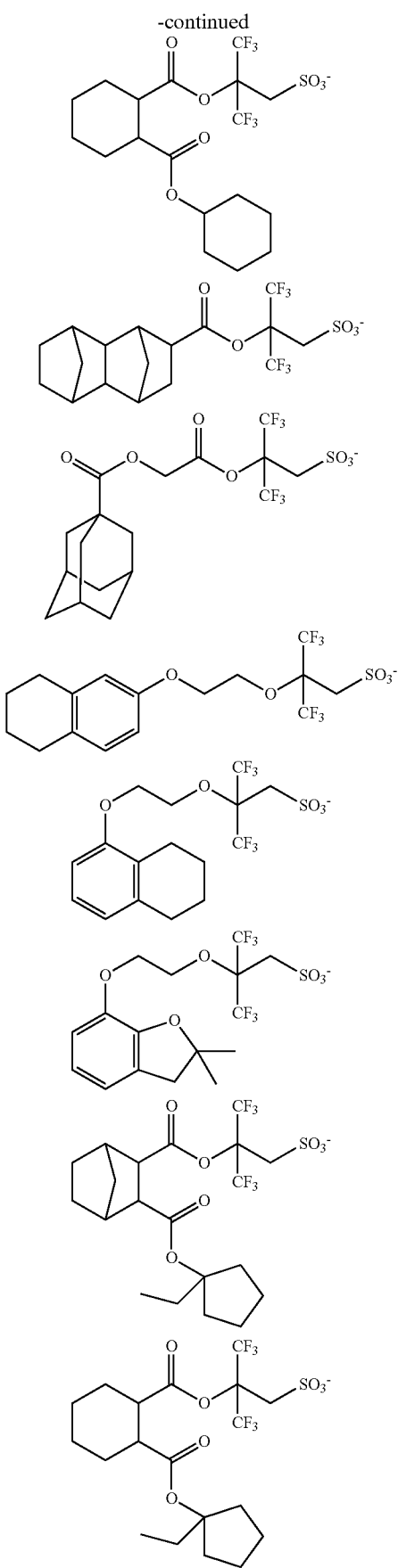
54
-continued
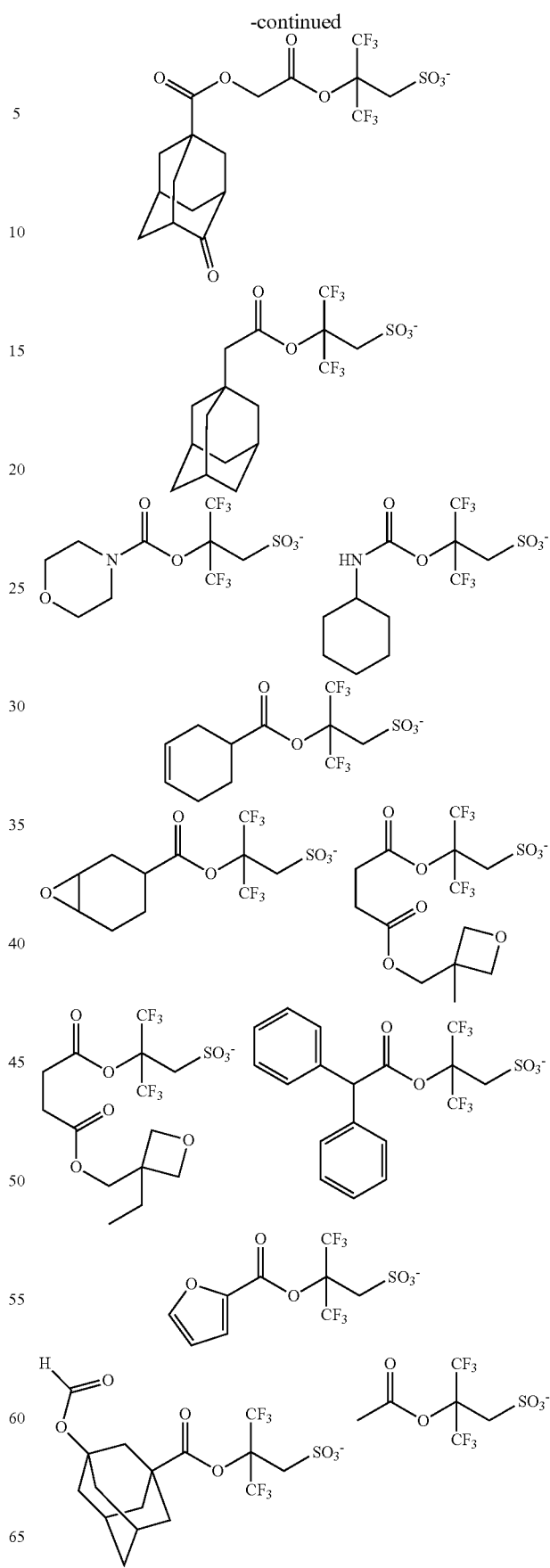

-continued
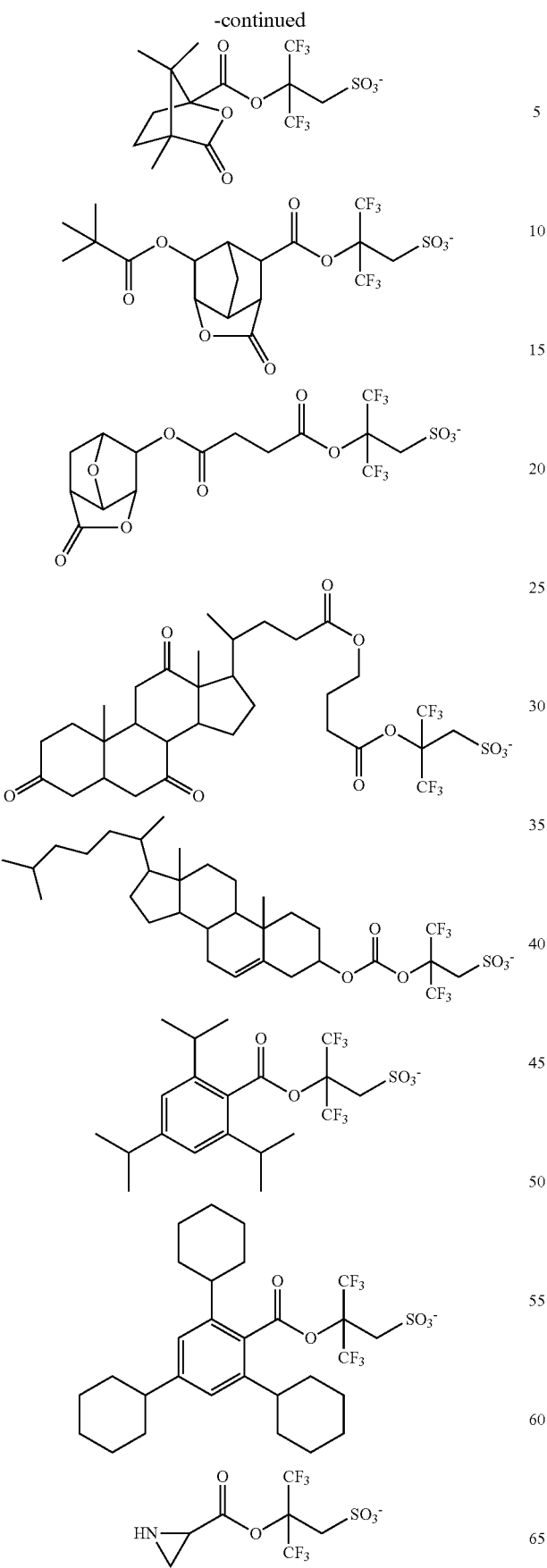
-continued
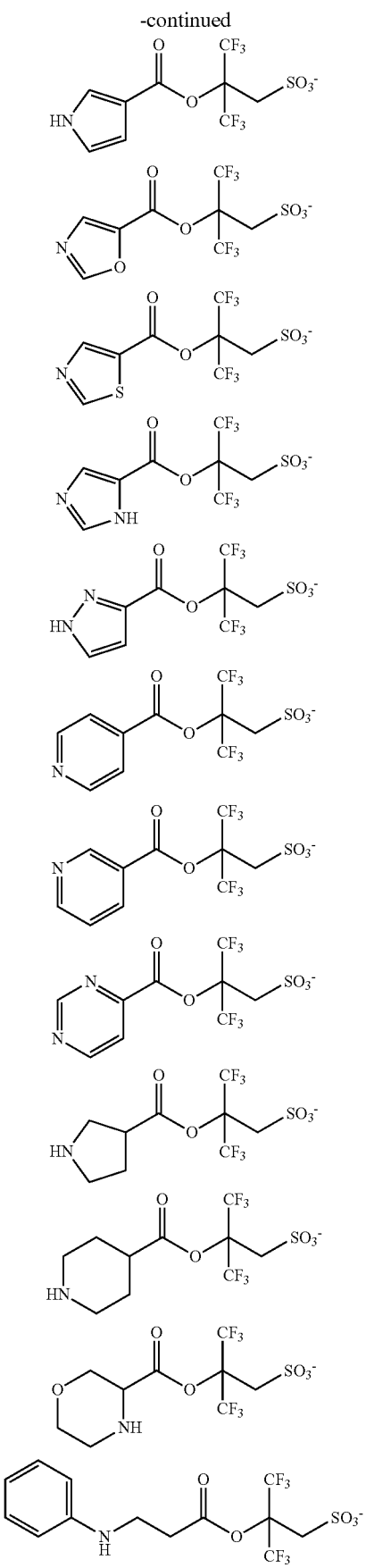

57
-continued
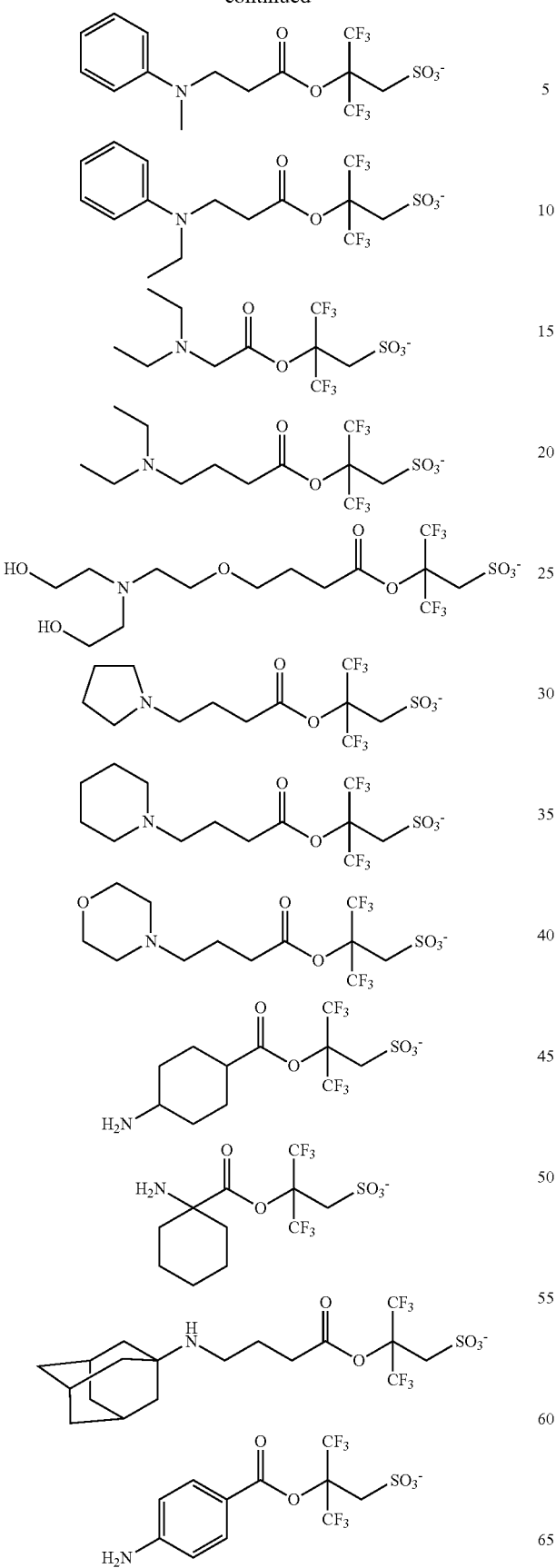
58
-continued
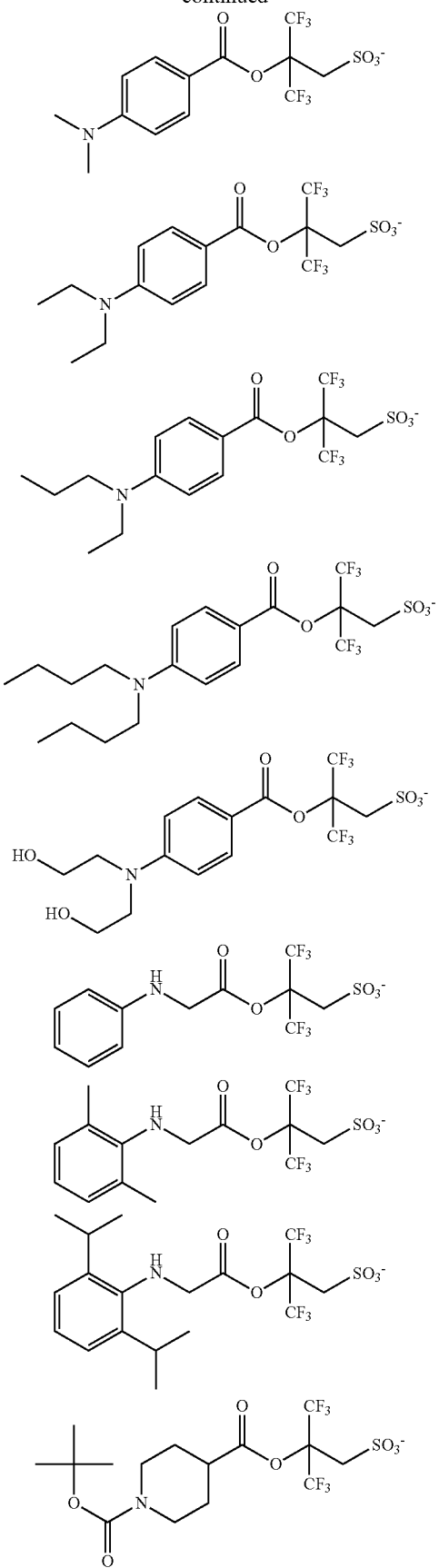

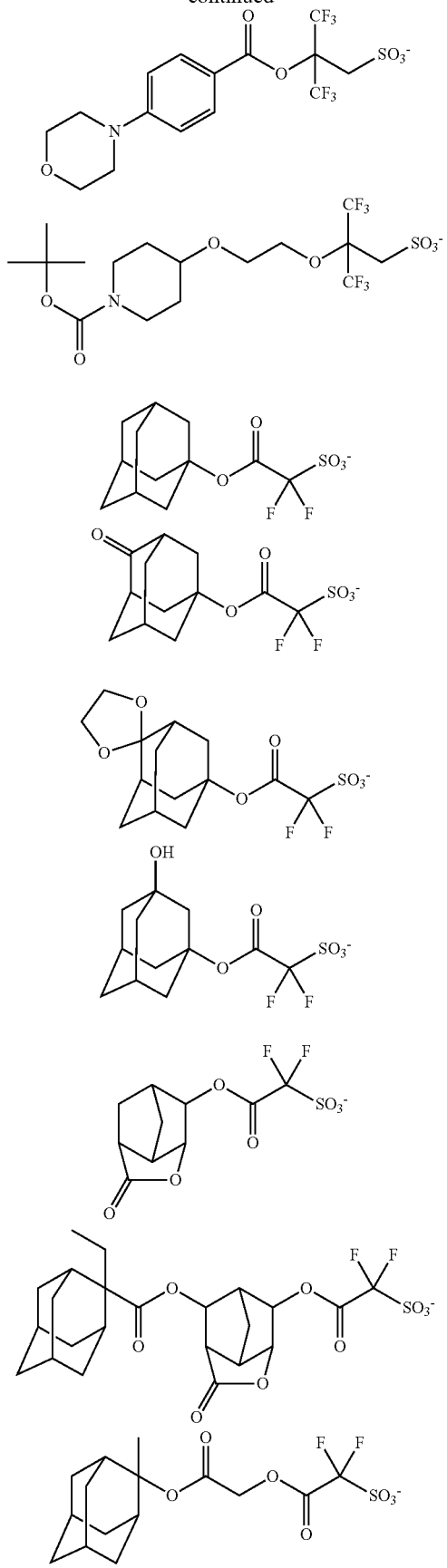
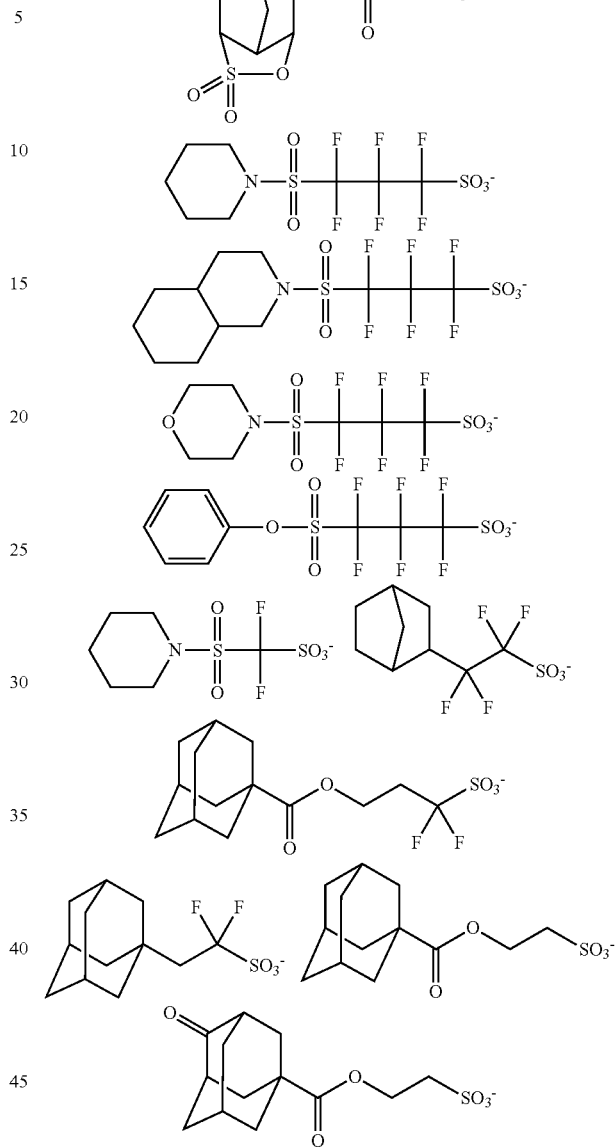

Exemplary structures for the inventive sulfonium salt include arbitrary combinations of cations with anions, both as exemplified above.

The resist composition comprising the inventive sulfonium salt is improved in lithography properties such as EL, MEF and LWR for the following reason. The nitrogen atom in the triarylamine structure contained in the inventive sulfonium salt has a very low basicity due to the conjugated effect with the three aryl rings and the inductive effect of sulfonium ion and aryl groups. The conjugated acid exhibits an acidity as demonstrated by a pKa value of about −7 to −3. However, since the sulfonium ion is decomposed in the course of acid generation upon exposure, the inductive effect is lost, and the nitrogen atom has a pKa value of about −5 to −2. This acidity is at an equivalent level as compared with an α,α-difluorosulfonic acid generating PAG which is common as the PAG in ArF resist compositions. For example, the PAG having 2-acyloxy-1,1,3,3,3-pentafluoropropane-1- sulfonic acid, described in Patent Document 4, generates an acid having a pKa value of about −3.0, which is approximately equal to the acidity of the conjugated acid of nitrogen atom in the triarylamine structure contained in the inventive sulfonium salt. Therefore, the nitrogen atom in the inventive sulfonium salt and the acid generated upon exposure, exhibiting approximate values of pKa, undergo partial proton exchange within the resist film. This proton exchange reaction is a reversible reaction because the two compounds have approximate values of pKa, and its reaction rate is quite fast. That is, a salt structure partially created by proton exchange acts to suppress acid diffusion, and a strong acidity is maintained because the proton exchange reaction is reversible unlike conventional quenchers. For this reason, lithography properties such as EL, MEF and LWR are improved at no sacrifice of sensitivity. It is noted that the pKa value is computed using ACD/ChemSketch of Advanced Chemistry Development Inc. (ACD/Labs).

Also, as compared with the sulfonium salt containing at least two sulfonium cation moieties in one triarylamine skeleton, described in Example of JP-A 2013-020089, the inventive sulfonium salt is improved in MEF for the following reason. Since the inventive sulfonium salt generates acid and triarylamine in a ratio of 1:1 upon exposure, the acid generated from the inventive sulfonium salt is prevented from diffusing by the proton exchange reaction with the equal amount of amine, i.e., acid diffusion is suppressed. On the other hand, the cation containing at least two sulfonium moieties in one triarylamine skeleton generates an excess amount of acid relative to amine upon exposure. The acid remaining in excess relative to the amine (whose diffusion is not fully suppressed by the above-mentioned mechanism) causes to degrade lithography properties such as MEF.

Where $R^4$ and $R^5$ are aromatic ring-free groups, the inventive sulfonium salt is also improved in rectangularity for the following reason. As compared with triphenylsulfonium salts which are generally used as PAG in ArF resist compositions, the inventive sulfonium salt is transparent at the exposure wavelength (193 nm) of ArF lithography. This allows light to reach the bottom of the resist film and minimizes the variation of exposure dose in height direction of the resist film, achieving uniform distribution of generated acid. This cooperates with the acid diffusion-suppressing effect mentioned above, to form a pattern of a rectangular profile.

One exemplary method for synthesizing the inventive sulfonium salt is illustrated by the following Scheme A.

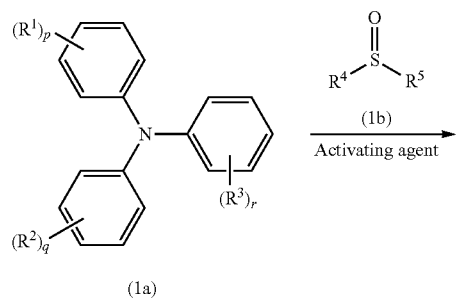

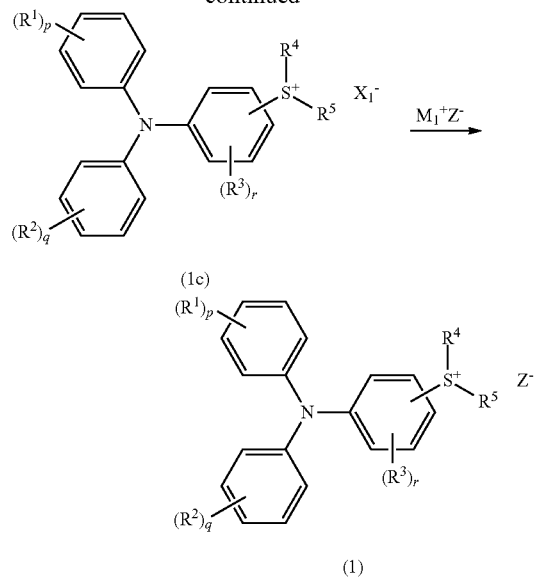

Herein $R^1$ to $R^5$, p, q, r, and $Z^-$ are as defined above, $X_1^-$ is an anion, and $M_1^+$ is a cation.

A sulfonium salt (1c) is synthesized by reacting a triarylamine (1a) with a sulfoxide (1b) in the presence of an activator. Suitable activators used herein include acids such as hydrochloric acid, sulfuric acid, nitric acid, perchloric acid, chlorosulfuric acid, trifluoromethanesulfonic acid, methanesulfonic acid, p-toluenesulfonic acid, and trifluoroacetic acid; phosphorus-based dehydrating agents such as phosphorus pentoxide, Eaton reagent (phosphorus pentoxide-methanesulfonic acid), and polyphosphoric acid; Lewis acids such as aluminum chloride and aluminum bromide; and esterifying agents such as phosphoryl chloride, trifluoromethanesulfonic anhydride, methanesulfonic anhydride, trifluoroacetic anhydride, and acetic anhydride, which may be used alone or in admixture. While the amount of the activator used varies with its type and reaction conditions, an appropriate amount may range from a catalytic amount to a solvent amount. If the amount is less than the appropriate amount, the reaction may take place with difficulty. If the amount is excessive, the selectivity of the position at which sulfonium moiety is introduced may lower, and more by-products may be formed by excessive reactions. Under reaction conditions using Eaton reagent, for example, it may be used in an amount of 1.0 mole to the solvent amount per mole of sulfoxide (1b). If the amount is too short, the reaction may take place with difficulty. Under reaction conditions using an esterifying agent such as trifluoromethanesulfonic anhydride, for example, it may be used in an amount of 0.5 to 10.0 moles per mole of sulfoxide (1b). If the amount is too short, the reaction may take place with difficulty. If the amount is excessive, by-products may be formed by excessive reactions.

The amount of triarylamine (1a) used is preferably 0.1 to 10.0 moles, more preferably 0.3 to 5.0 moles per mole of sulfoxide (1b). If the amount is too short, excessive reactions may take place, leading to a lowering of yield and difficulty of purification. If the amount is excessive, a substantial fraction of triarylamine (1a) may be left unreacted, inviting economic disadvantages due to increase of reactant cost and lowering of pot yield.

Examples of the solvent used in Scheme A include hydrocarbons such as toluene, xylene, hexane and heptane; chlorinated solvents such as methylene chloride, chloroform and dichloroethane; ethers such as diethyl ether, tetrahydrofuran and dibutyl ether, ketones such as acetone and 2-butanone; esters such as ethyl acetate and butyl acetate; nitriles such as acetonitrile; and aprotic polar solvents such as N,N-dimethylformamide and N,N-dimethylacetamide, which may be used alone or in admixture. The reaction may be performed even in a solventless system. The reaction temperature is preferably from −70° C. to about the boiling point of the solvent if any. While the reaction temperature may be selected as appropriate depending on other reaction conditions, it is typically from −10° C. to about the boiling point of the solvent.

By further effecting ion exchange with sulfonium salt (1c) using a salt having a predetermined anion ($Z^-$), the desired sulfonium salt (1) may be synthesized. Ion exchange is readily performed by any well-known methods, for example, with reference to Patent Document 4.

Another exemplary method for synthesizing the inventive sulfonium salt is illustrated by the following Scheme B.

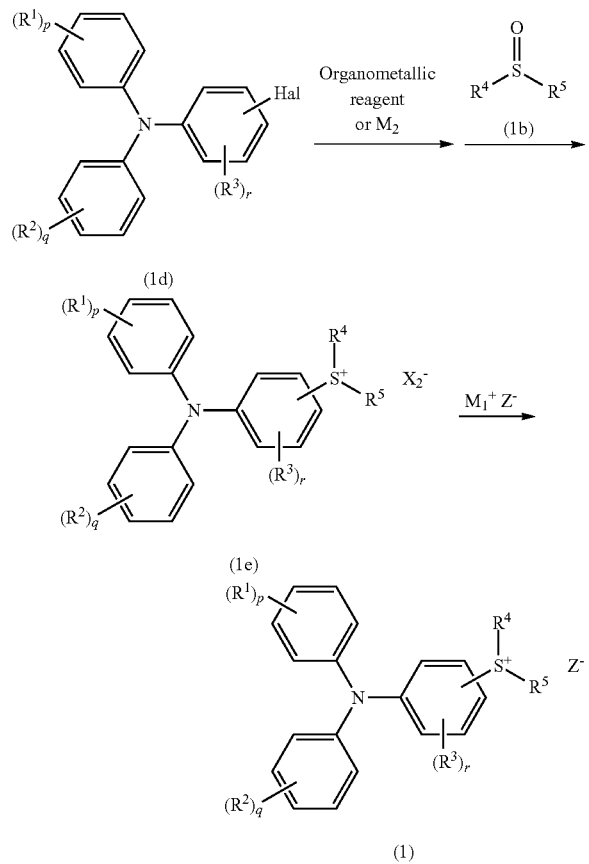

Herein $R^1$ to $R^5$, p, q, r, Z, and $M_1^+$ are as defined above, Hal is halogen, $X_2^-$ is an anion, and $M_2$ is a metal.

A sulfonium salt (1e) is synthesized by acting an organometallic reagent or metal on a triarylamine (1d) to form a nucleophile, and reacting it with a sulfoxide (1b). Suitable organometallic reagents include trityl lithium, trityl sodium, trityl potassium, methyl lithium, phenyl lithium, sec-butyl lithium, tert-butyl lithium, and ethylmagnesium bromide. Suitable metals include lithium, sodium, potassium and magnesium. The amount of the organometallic reagent or metal used is preferably 0.5 to 5.0 moles, more preferably 0.8 to 2.0 moles per mole of triarylamine (1d). If the amount is too short, formation of the nucleophile may be retarded, resulting in a lowering of yield. If the amount is excessive, there may occur side-reactions such as reaction of unreacted organometallic reagent with sulfoxide (1b), and it may be difficult to reduce the metal content in the final product, sulfonium salt (1), which is detrimental from the standpoint of quality control.

The amount of triarylamine (1d) used is preferably 0.5 to 10.0 moles, more preferably 0.8 to 5.0 moles per mole of sulfoxide (1b). If the amount is too short, the reaction may be retarded, resulting in a lowering of yield. If the amount is excessive, there may arise economic disadvantages due to increase of reactant cost and lowering of pot yield, and there may be formed more impurities originating from triarylamine (1d), leading to difficulty of purification.

Examples of the solvent used in Scheme B include aprotic solvents, for example, hydrocarbons such as toluene, xylene, hexane and heptane; chlorinated solvents such as methylene chloride, chloroform and dichloroethane; and ethers such as diethyl ether, tetrahydrofuran and dibutyl ether, which may be used alone or in admixture. The reaction temperature is preferably from −70° C. to about the boiling point of the solvent. While the reaction temperature may be selected as appropriate depending on other reaction conditions, it is typically from −10° C. to about the boiling point of the solvent.

Where little reaction takes place with the nucleophile alone, an activator for sulfoxide (1b) may be added. The activator used herein may be selected from the aforementioned esterifying agents and chlorosilanes such as trimethylsilyl chloride and triethylsilyl chloride. In case an esterifying agent which is able to react with the nucleophile is used as the activator, preferably the sulfoxide (1b) is first reacted with the activator to form an active intermediate before it is reacted with the nucleophile.

By further effecting ion exchange with sulfonium salt (1e) using a salt having a predetermined anion ($Z^-$), the desired sulfonium salt (1) may be synthesized. Ion exchange is readily performed by any well-known methods, for example, with reference to Patent Document 4.

Resist Composition

Another embodiment of the invention is a chemically amplified resist composition comprising (A) a photoacid generator in the form of a sulfonium salt having formula (1) as an essential component. The resist composition may further comprise:

(B) a base resin,
(C) an organic solvent,
(D) a photoacid generator other than the sulfonium salt having formula (1) (also referred to as second photoacid generator),
(E) a quencher,
(F) a surfactant which is insoluble or substantially insoluble in water and soluble in alkaline developer, and/or a surfactant which is insoluble or substantially insoluble in water and alkaline developer, and
(G) another component.

Components (D),(E),(F) and (G) are optional, that is, may be added if necessary.

In the resist composition, an appropriate amount of the PAG as component (A) is 0.1 to 40 parts by weight, more preferably 0.2 to 20 parts by weight per 100 parts by weight of the base resin (B). As long as the amount is at least 0.1 pbw, the component exerts a full function of photoacid generator. As long as the amount is up to 40 pbw, the component eliminates any performance degradations including foreign particles generated due to solubility shortage.

(B) Base Resin

The base resin used herein as component (B) preferably contains a polymer comprising recurring units having the formula (a) and recurring units having the formula (b).

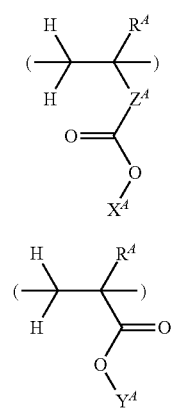

In formulae (a) and (b), $R^A$ is hydrogen, fluorine, methyl or trifluoromethyl. $Z^A$ is a single bond, phenylene group, naphthylene group or (backbone)-C(=O)—O—Z'—, wherein Z' is a $C_1$-$C_{10}$ straight, branched or cyclic alkylene group which may contain a hydroxyl, ether, ester radical or lactone ring, or phenylene group or naphthylene group. $X^A$ is an acid labile group. $Y^A$ is hydrogen or a polar group having at least one structure selected from among hydroxyl, cyano, carbonyl, carboxyl, ether, ester, sulfonic acid ester, carbonate radical, lactone ring, sultone ring and carboxylic anhydride.

The acid labile group represented by $X^A$ in formula (a) may be selected from a variety of such groups. Examples of the acid labile group include tertiary alkyl groups of 4 to 20 carbon atoms, trialkylsilyl groups in which each alkyl moiety has 1 to 6 carbon atoms, and oxoalkyl groups of 4 to 20 carbon atoms. With respect to the structure of these acid labile groups, reference should be made to U.S. Pat. No. 9,164,384 (JP-A 2014-225005, paragraphs [0016]-[0035]).

Examples of the structure having formula (a) wherein $Z^A$ is a variant are described in U.S. Pat. No. 9,164,384 (JP-A 2014-225005, paragraph [(0015]). The preferred structures are shown below, but not limited thereto. Notably, $R^A$ and $X^A$ are as defined above.

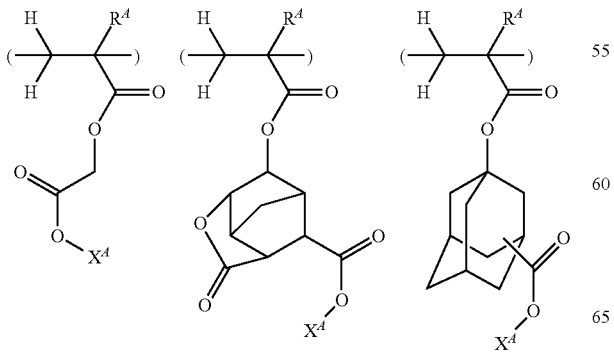

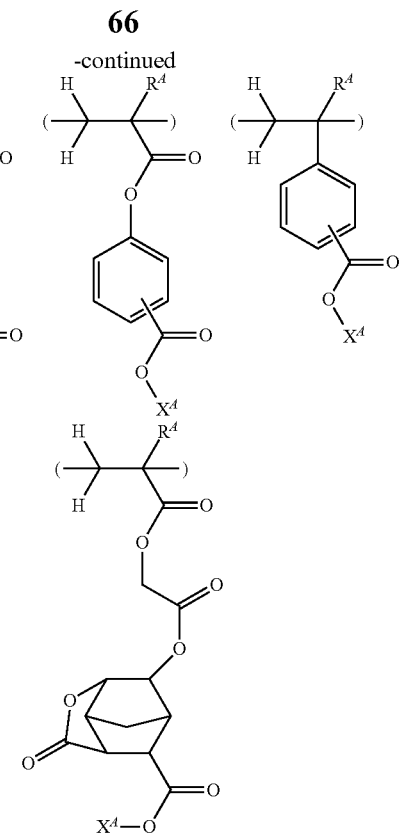

Suitable recurring units having formula (a) and suitable recurring units having formula (b) include those described in JP-A 2015-214634, paragraphs [0013]-[0023] and [0066]-[0109], JP-A 2014-225005, paragraphs [0014]-[0054], and JP-A 2015-166833, paragraphs [0029]-[0094]. Among others, tertiary ester structures containing an alicyclic group are preferred as formula (a), and hydroxyadamantane (meth)acrylate structures and (meth)acrylate structures containing a lactone ring or sultone ring are preferred as formula (b).

Preferred structures of the recurring unit having formula (a) are given below, but not limited thereto. Herein $R^A$ is as defined above.

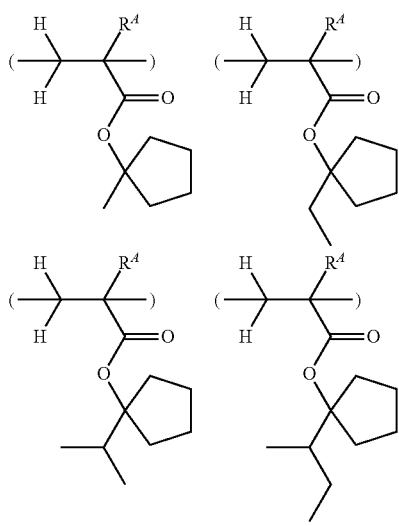

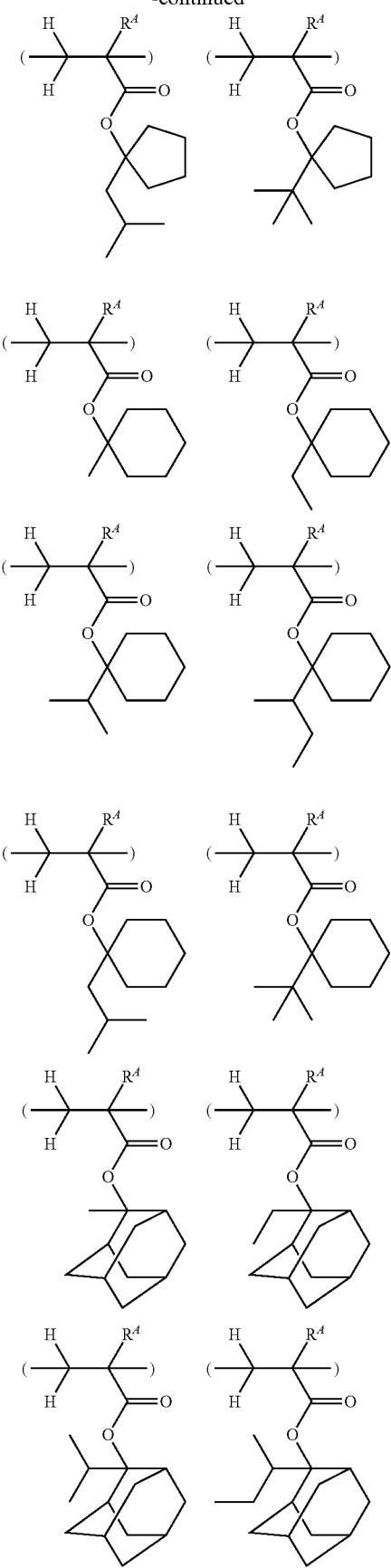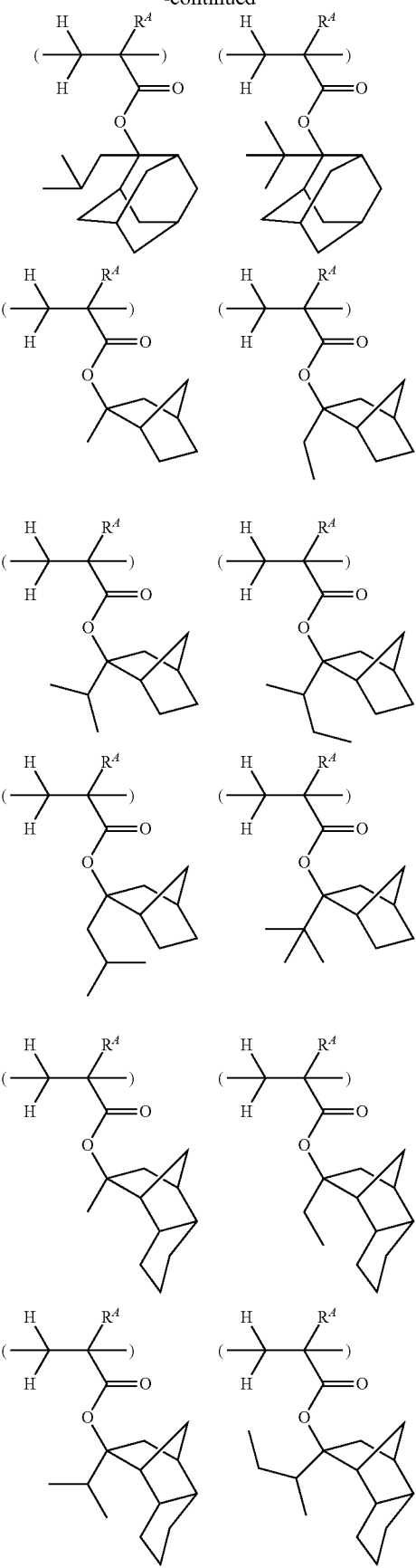

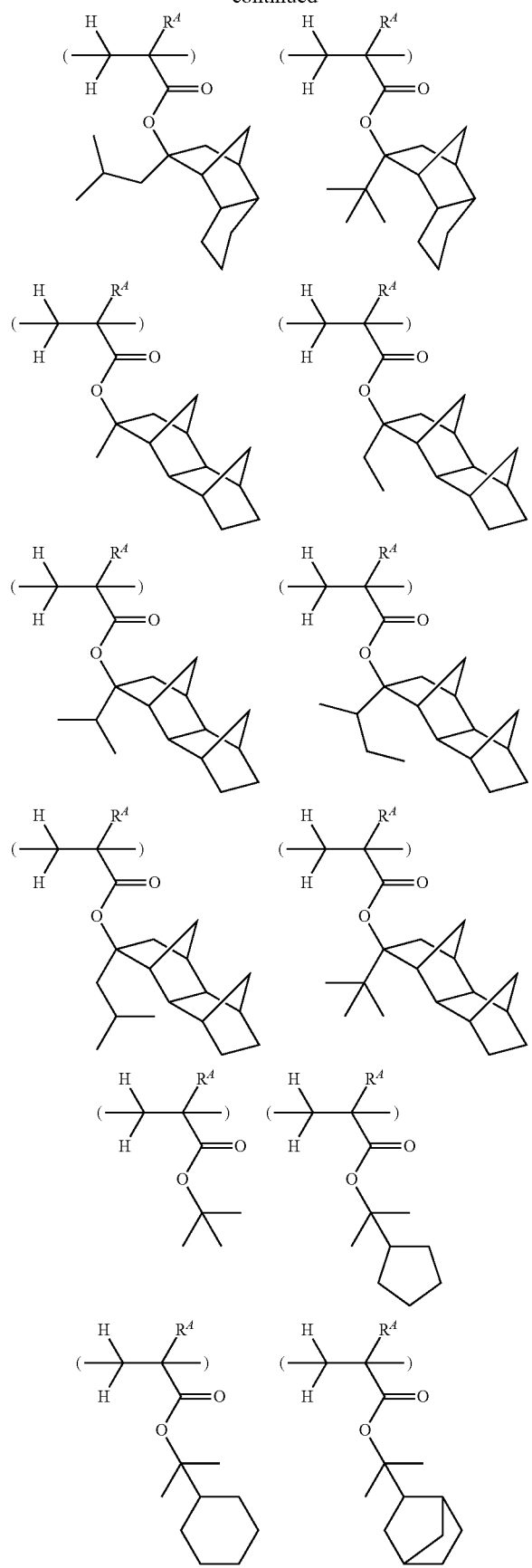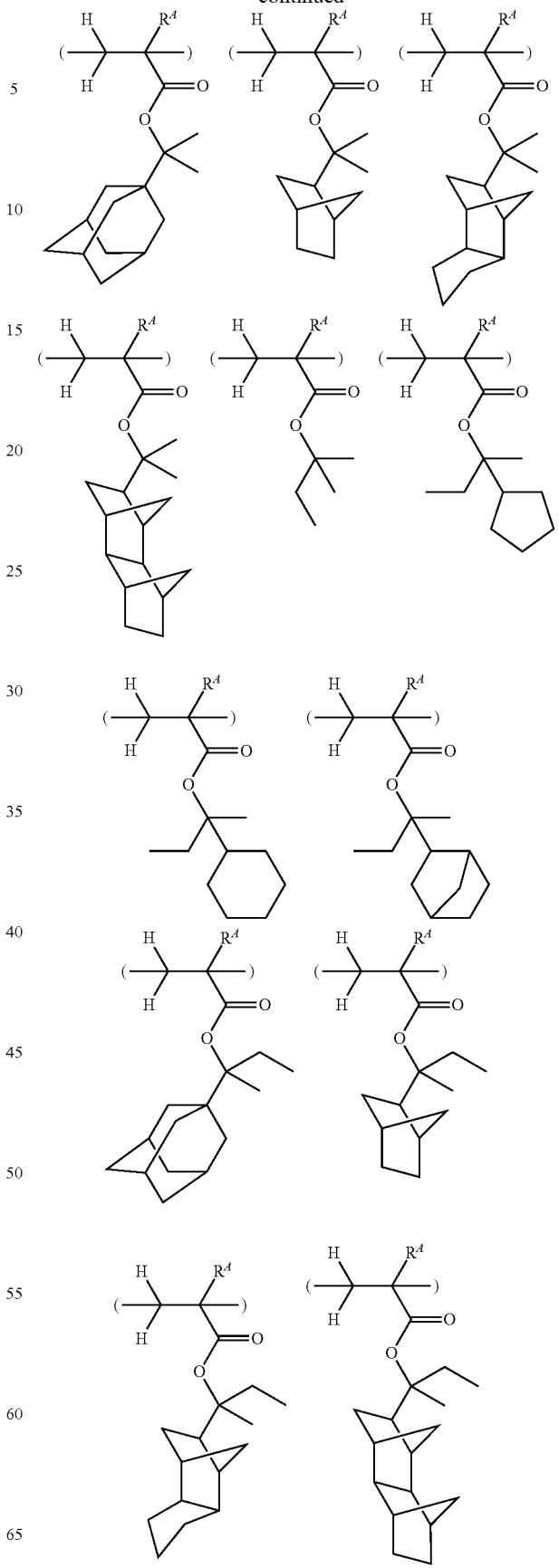

-continued
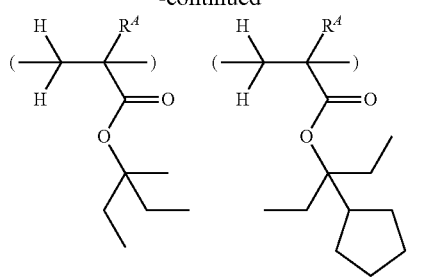
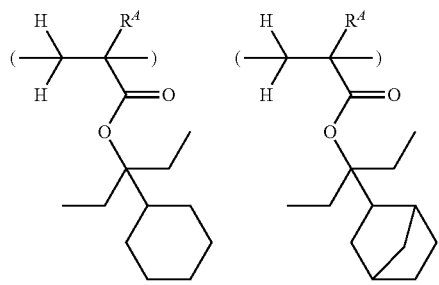
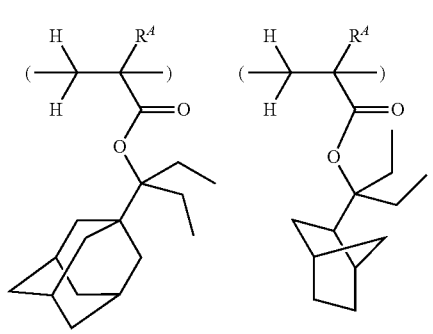
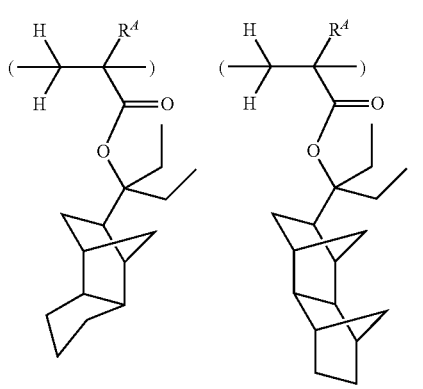
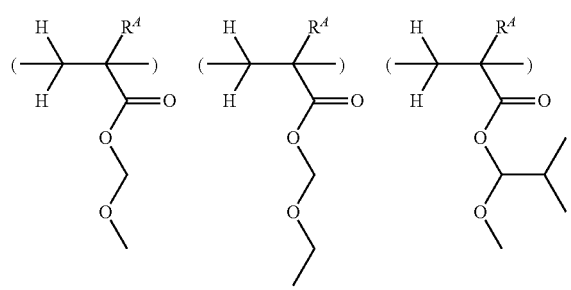
-continued
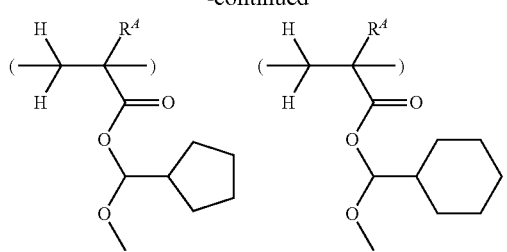
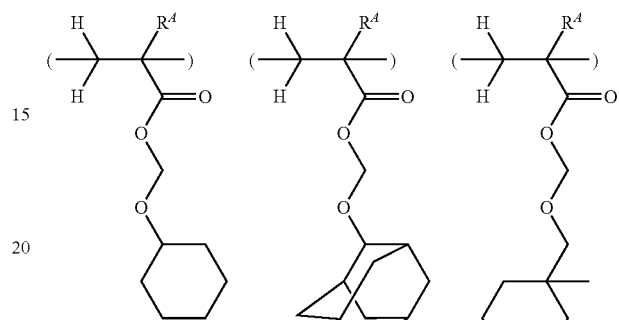
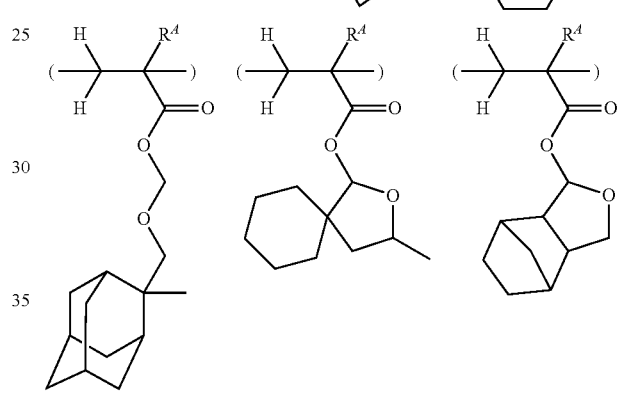
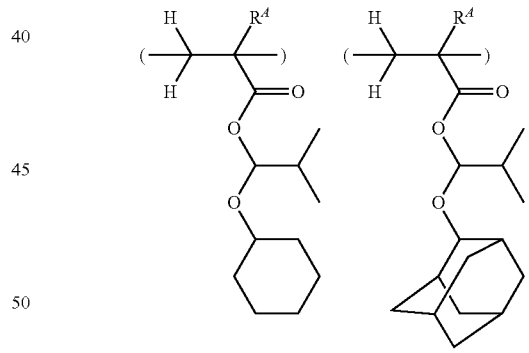
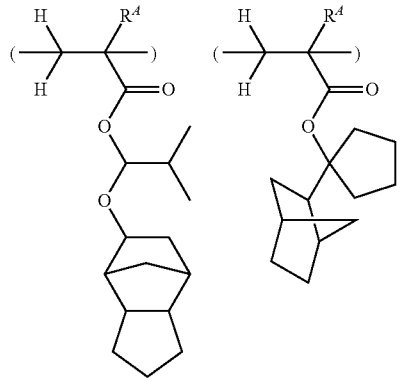

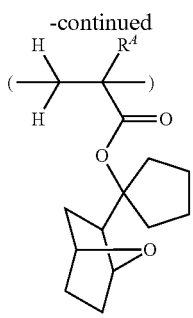

While the foregoing examples correspond to those units wherein $Z^A$ is a single bond, $Z^A$ which is other than a single bond may be combined with similar acid labile groups. Examples of units wherein $Z^A$ is other than a single bond are substantially the same as illustrated above.

Illustrative, non-limiting examples of the recurring unit having formula (b) are shown below. Herein $R^A$ is as defined above.

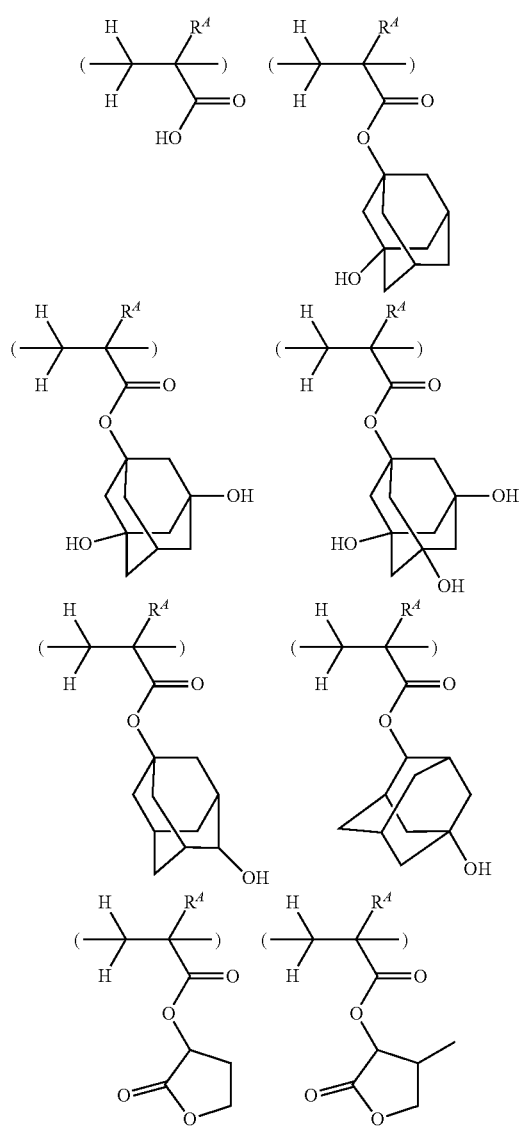
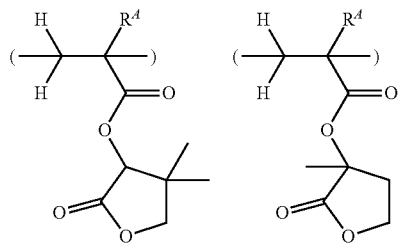
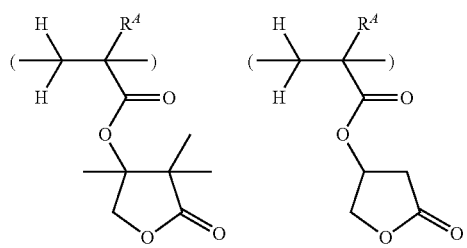
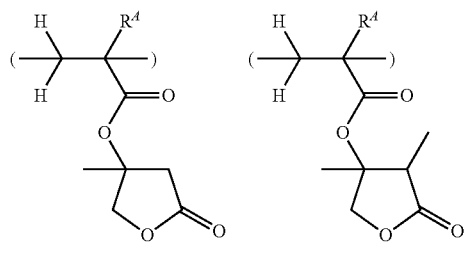
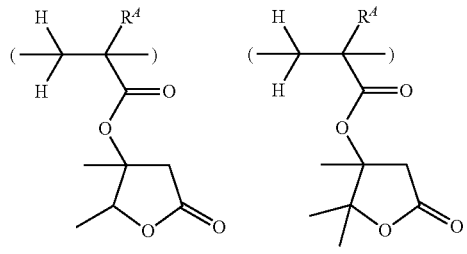
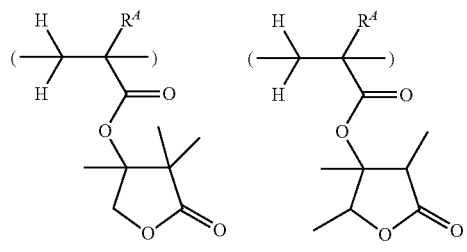
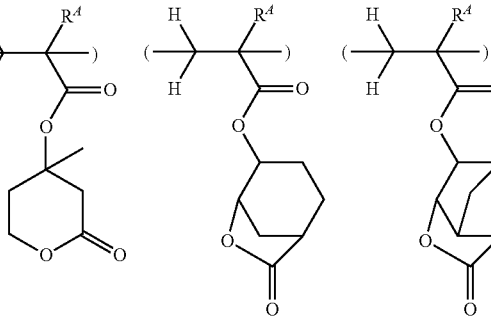

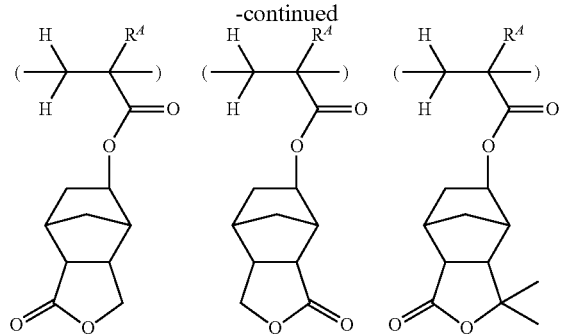
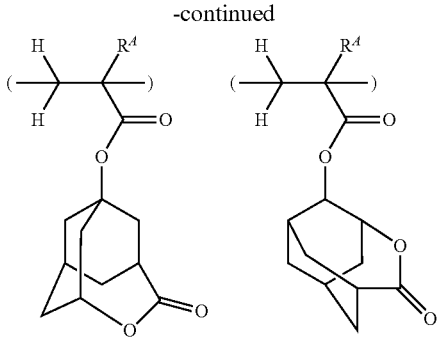
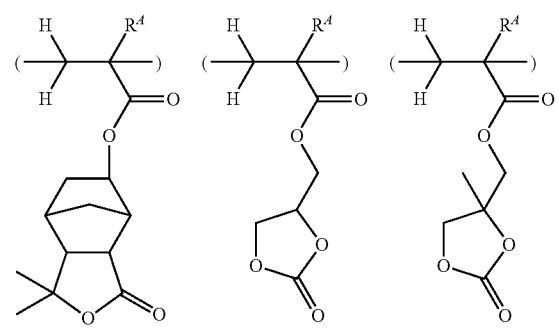
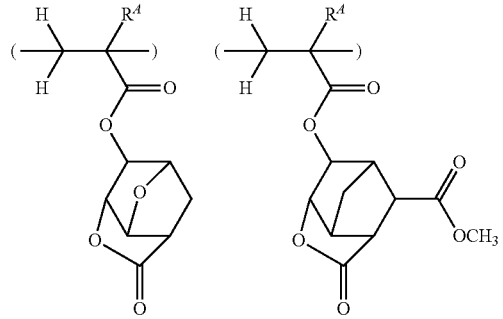
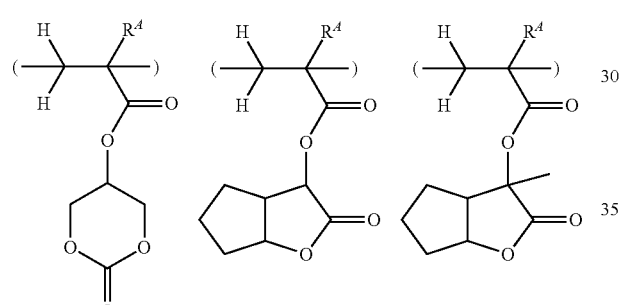
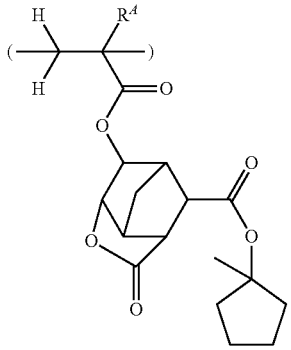
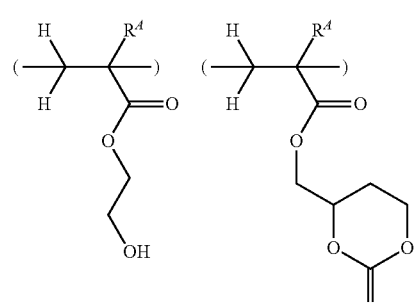
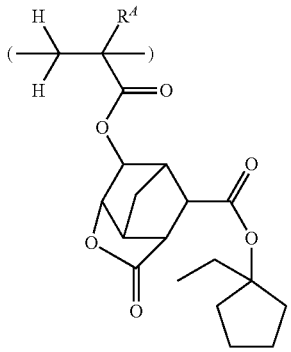
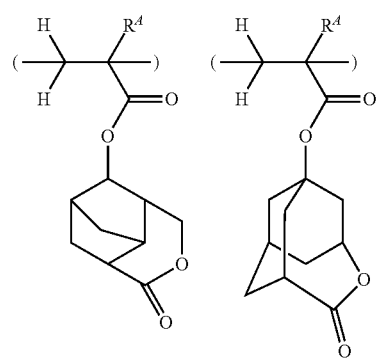
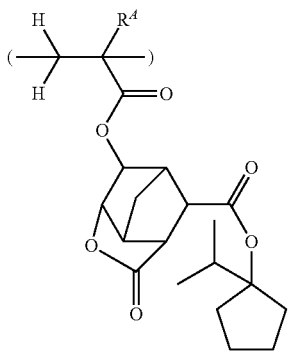

-continued
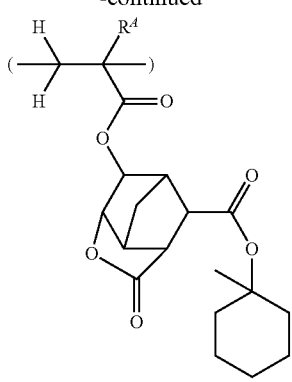
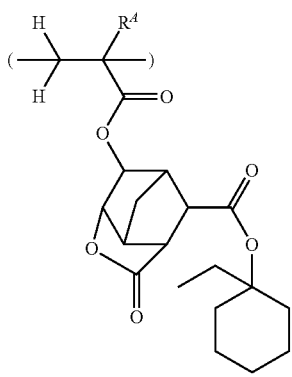
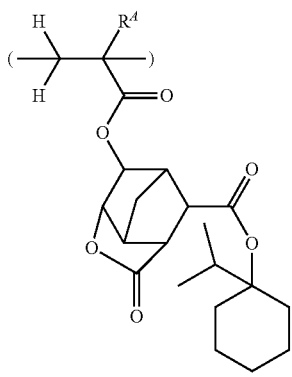
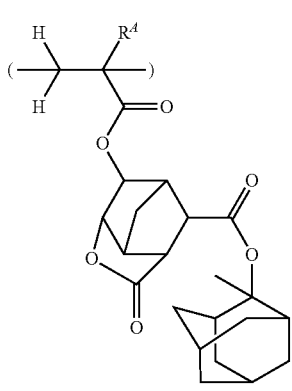
-continued
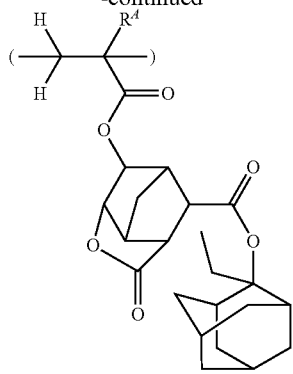
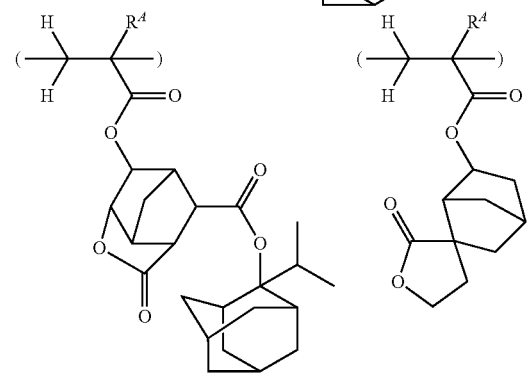
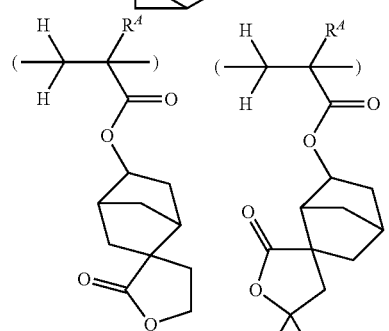
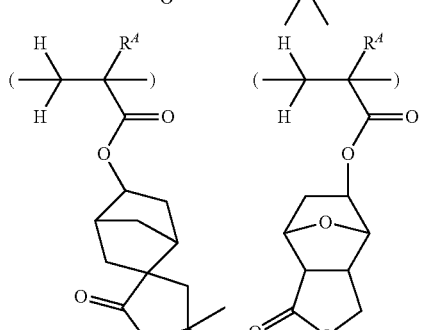
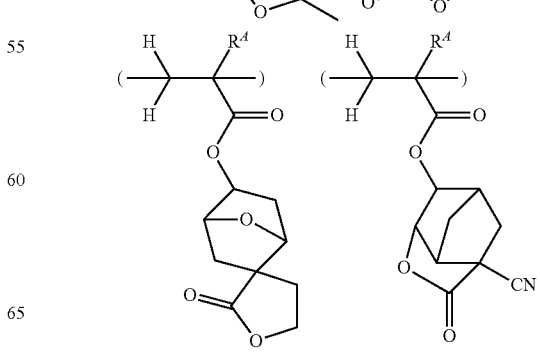

-continued
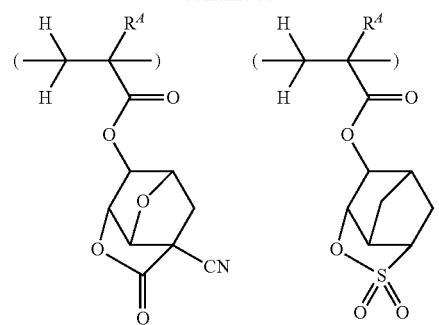
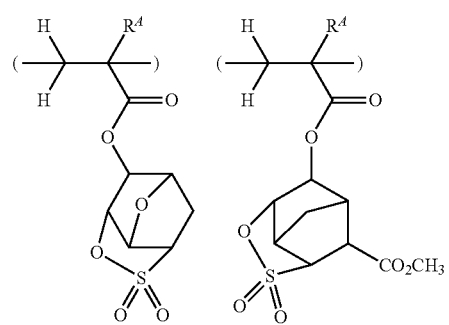
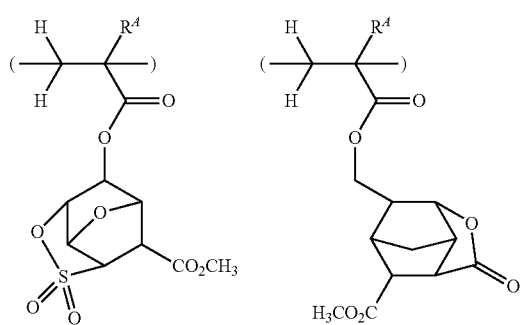
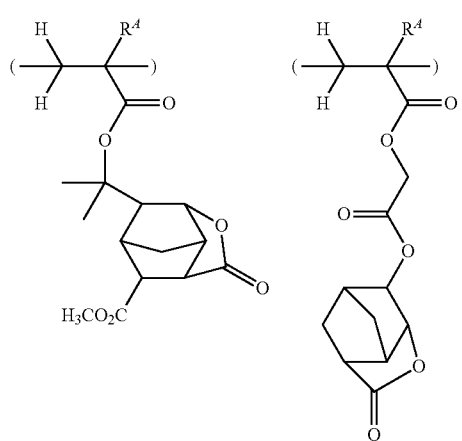
-continued
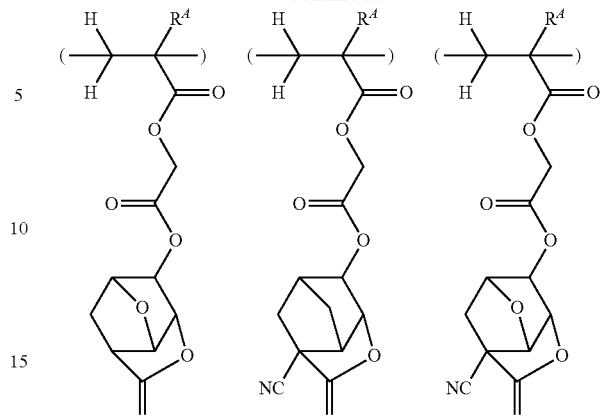
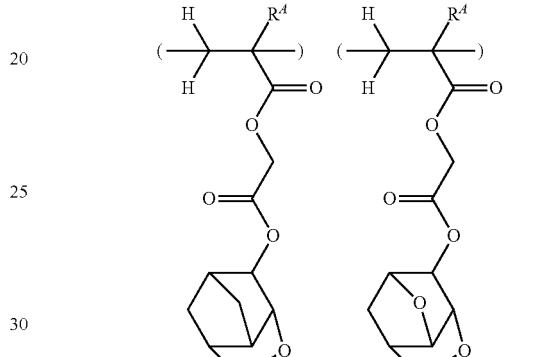
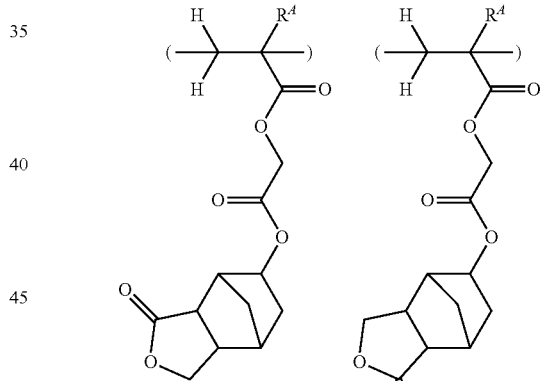
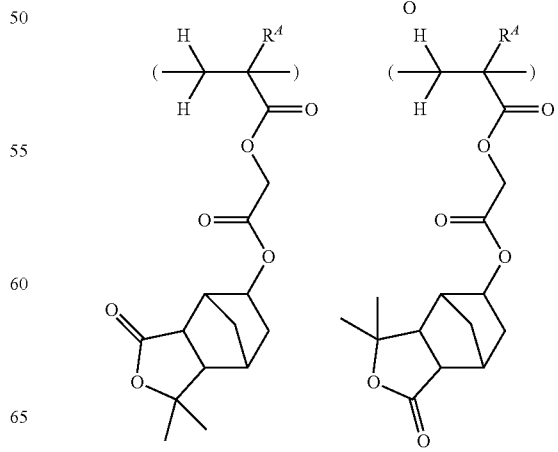

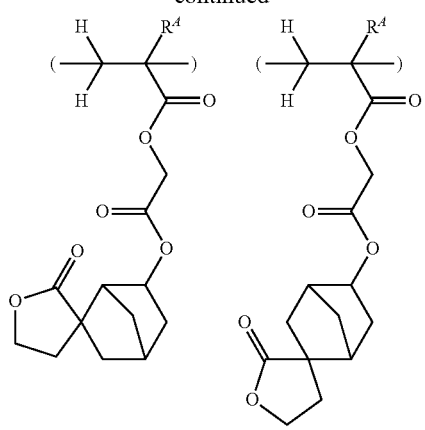
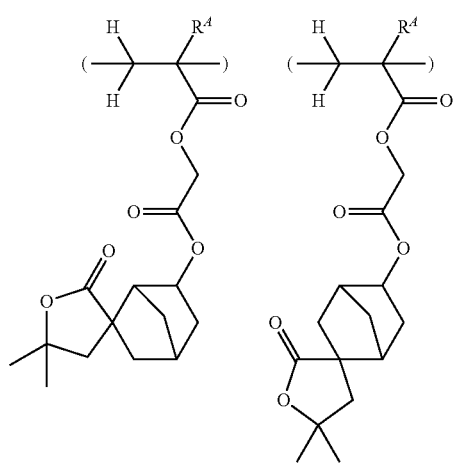
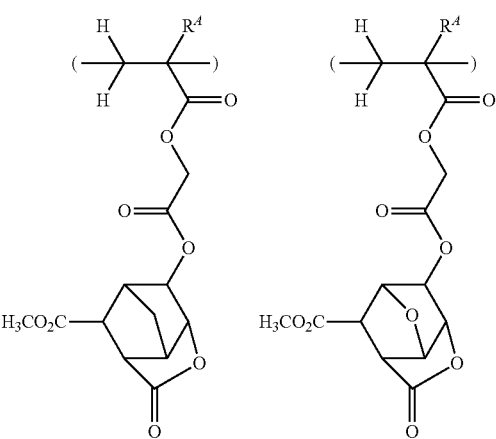
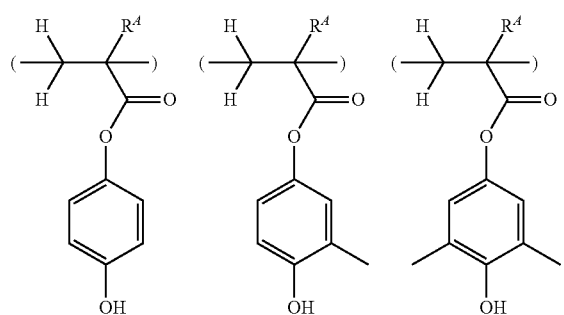
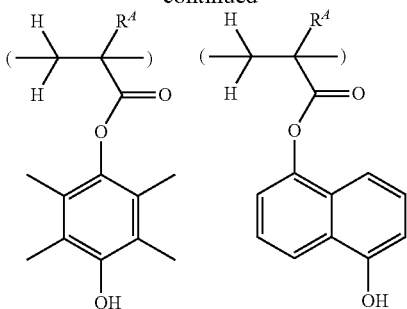
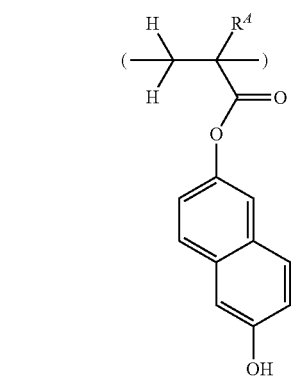
In addition to the recurring units having formulae (a) and (b), the polymer may further comprise recurring units having the formula (c1),(c2),(c3) or (c4).
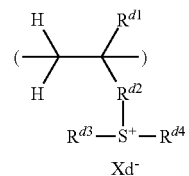
(c1)
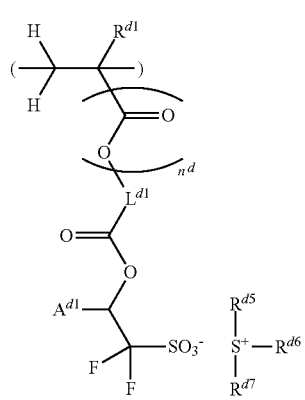
(c2)

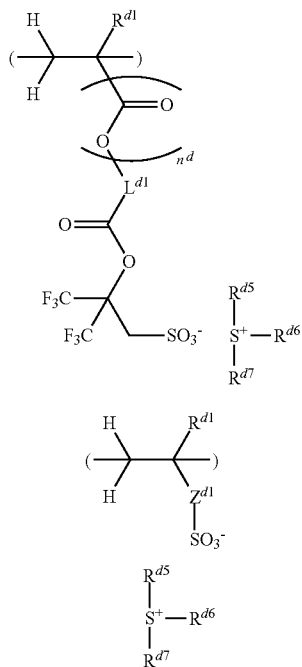

(c3)

(c4)

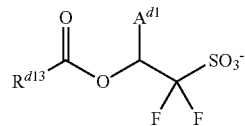

(c5)

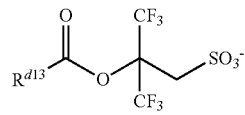

(c6)

In formulae (c1) to (c4), $R^{d1}$ is each independently hydrogen, fluorine, methyl or trifluoromethyl. $R^{d2}$ is a single bond, phenylene group, —O—$R^{d11}$—, or —C(=O)—$Y^{d1}$—$R^{d11}$—, wherein $Y^{d1}$ is —O— or —NH—, and $R^{d11}$ is a $C_1$-$C_{20}$ straight, branched or cyclic alkylene group, $C_2$-$C_{20}$ straight, branched or cyclic alkenylene group, or phenylene group, which may contain a heteroatom. $R^{d3}$, $R^{d4}$, $R^{d5}$, $R^{d6}$ and $R^{d7}$ are each independently a $C_1$-$C_{20}$ straight, branched or cyclic monovalent hydrocarbon group which may contain a heteroatom. Any two of $R^{d2}$, $R^{d3}$ and $R^{d4}$ may bond together to form a ring with the sulfur atom to which they are attached, and any two of $R^{d5}$, $R^{d6}$ and $R^{d7}$ may bond together to form a ring with the sulfur atom to which they are attached. $Xd^-$ is a non-nucleophilic counter ion. $A^{d1}$ is hydrogen or trifluoromethyl. $L^{d1}$ is a single bond or a $C_1$-$C_{20}$ straight, branched or cyclic divalent hydrocarbon group which may contain a heteroatom. The subscript $n^d$ is 0 or 1, and $n^d$ is 0 when $L^{d1}$ is a single bond. $Z^{d1}$ is a single bond, methylene, ethylene, phenylene, fluorinated phenylene, —O—$R^{d11}$, or —C(=O)—$Y^{d1}$—$R^{d12}$— wherein $R^{d12}$ is an optionally substituted phenylene group.

In formulae (c1) to (c4), preferably $R^{d2}$ to $R^{d7}$ are each independently a structure containing a phenyl group which bonds with $S^+$ in the formula.

Examples of the non-nucleophilic counter ion represented by $Xd^-$ in formula (c1) include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imides such as bis(trifluoromethylsulfonyl)imide, bis(perfluoroethylsulfonyl)imide, and bis(perfluorobutylsulfonyl)imide; and methides such as tris(trifluoromethylsulfonyl)methide and tris(perfluoroethylsulfonyl) methide.

Other non-nucleophilic counter ions include anions having the formulae (c5) and (c6).

In formulae (c5) and (c6), $A^{d1}$ is as defined above, and $R^{d13}$ is a $C_1$-$C_{40}$ straight, branched or cyclic monovalent hydrocarbon group which may contain a heteroatom.

The anion moiety of formula (c5) is exemplified by the aforementioned structures of the anion of formula (3), (4) or (5) and those structures illustrated in JP-A 2014-177407, paragraphs [0100]-[0101]. The anion moiety of formula (c6) is exemplified by the aforementioned structures of the anion of formula (3), (4) or (5) and those structures illustrated in JP-A 2010-215608, paragraphs [0080]-[0081].

Illustrative structures of the anion moiety in formula (c2) include those described in JP-A 2014-177407, paragraphs [0021]-[0026]. Illustrative structures of the anion moiety in formula (c2) wherein $A^{d1}$ is hydrogen include those described in JP-A 2010-116550, paragraphs [0021]-[0028]. Illustrative structures of the anion moiety in formula (c2) wherein Ad is trifluoromethyl include those described in JP-A 2010-077404, paragraphs [0021]-[0027]. Illustrative structures of the cation moiety in formula (c2) include those described in JP-A 2008-158339, paragraph [0223].

Illustrative structures of the anion moiety in formula (c3) include the structures illustrated for formula (c2) wherein —CH($A^{d1}$)$CF_2SO_3^-$ is replaced by —C($CF_3$)$_2CH_2SO_3^-$.

Illustrative structures of the sulfonium cation in formulae (c2) to (c4) include those cations described in JP-A 2008-158339, paragraph [0223] and those cations in the onium salt having formula (6) which will be exemplified later.

The polymer as the base resin may have further copolymerized therein recurring units of the structure having a hydroxyl group protected with an acid labile group. The recurring unit of the structure having a hydroxyl group protected with an acid labile group is not particularly limited as long as it has one or more protected hydroxyl-bearing structure such that the protective group may be decomposed to generate a hydroxyl group under the action of acid. Examples of these recurring units include those described in JP-A 2014-225005, paragraphs [0055]-[0065] and JP-A 2015-214634, paragraphs [0110]-[0115].

In addition to the foregoing units, the polymer may further comprise other recurring units, for example, recurring units having an oxirane ring or oxetane ring. The inclusion of recurring units having an oxirane or oxetane ring ensures that the exposed region of resist film is improved in film retention and etch resistance because the exposed region is crosslinked.

Also included in the other recurring units are units derived from substituted acrylates such as methyl methacrylate, methyl crotonate, dimethyl maleate, and dimethyl itaconate; unsaturated carboxylic acids such as maleic acid, fumaric acid, and itaconic acid; cyclic olefins such as norbornene, norbornene derivatives, and tetracyclo[$6.2.1.1^{3,6}.0^{2,7}$]dodecane derivatives; unsaturated acid anhydrides such as itaconic anhydride; vinyl aromatics such as styrene, vinylnaphthalene, hydroxystyrene, hydroxyvinylnaphthalene, and 4-tert-butoxystyrene; and other monomers. Examples of the other recurring units include those described in JP-A 2015-214634, paragraphs [0120]-[0132]. In combination with the polymer described above, a hydrogenated product of ring-opening metathesis polymerization (ROMP) polymer may be used as the base resin. Any of the hydrogenated ROMP polymers described in JP-A 2003-066612 may be used.

The polymer has a weight average molecular weight (Mw) of preferably 1,000 to 500,000, more preferably 3,000 to 100,000, as measured by gel permeation chromatography (GPC) versus polystyrene standards using tetrahydrofuran (THF) solvent. As long as Mw is within the range, etching resistance is satisfactory, and a difference in dissolution rate before and after exposure is ensured, leading to good resolution. The polymer should preferably have a dispersity (Mw/Mn) of 1.20 to 2.50, more preferably 1.30 to 1.80.

The method of synthesizing the polymer as the base resin is, for example, by dissolving one or more monomers corresponding to the desired recurring units in an organic solvent, adding a radical initiator, and effecting heat polymerization. With respect to the polymerization method, reference should be made to U.S. Pat. No. 9,256,127 (JP-A 2015-214634, paragraphs [0134]-[0137]). The acid labile group that has been incorporated in the monomer may be kept as such, or polymerization may be followed by protection or partial protection.

While the polymer comprises recurring units derived from monomers, the molar fractions of respective units preferably fall in the following range (mol %), but are not limited thereto:

(I) 1 to 80 mol %, more preferably 5 to 70 mol %, even more preferably 10 to 60 mol % of recurring units of at least one type having formula (a),
(II) 20 to 99 mol %, more preferably 30 to 95 mol %, even more preferably 40 to 90 mol % of recurring units of at least one type having formula (b), and optionally,
(III) 0 to 30 mol %, more preferably 0 to 20 mol %, and even more preferably 0 to 15 mol % of recurring units of at least one type having formula (c1), (c2), (c3) or (c4), and optionally,
(IV) 0 to 80 mol %, more preferably 0 to 70 mol %, and even more preferably 0 to 60 mol % of recurring units of at least one type derived from another monomer(s).

(C) Organic Solvent

The resist composition may comprise (C) an organic solvent. The organic solvent used herein is not particularly limited as long as the sulfonium salt, the polymer and other components are soluble therein. Examples of the organic solvent are described in U.S. Pat. No. 7,537,880 (JP-A 2008-111103, paragraphs [0144] to [0145]). Specifically, exemplary solvents include ketones such as cyclohexanone and methyl-2-n-pentyl ketone; alcohols such as 3-methoxybutanol, 3-methyl-3-methoxybutanol, 1-methoxy-2-propanol, 1-ethoxy-2-propanol, and diacetone alcohol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether, esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, and mixtures thereof. Where an acid labile group of acetal form is used, a high-boiling alcohol solvent such as diethylene glycol, propylene glycol, glycerol, 1,4-butanediol or 1,3-butanediol may be added for accelerating deprotection reaction of acetal. Of the above organic solvents, it is recommended to use 1-ethoxy-2-propanol, PGMEA, cyclohexanone, γ-butyrolactone, and mixtures thereof because the PAG is most soluble therein.

An appropriate amount of the organic solvent (C) used is 100 to 8,000 parts, more preferably 400 to 5,000 parts by weight per 100 parts by weight of the base resin (B).

(D) Second PAG

The resist composition may further comprise (D) a photoacid generator other than the sulfonium salt of formula (1), which is referred to as second photoacid generator. The second PAG may be any compound capable of generating an acid upon exposure to high-energy radiation. Suitable PAGs include sulfonium salts, iodonium salts, sulfonyldiazomethane, N-sulfonyloxydicarboxyimide, O-arylsulfonyloxime, and O-alkylsulfonyloxime compounds. These PAGs may be used alone or in admixture of two or more. Suitable PAGs are described, for example, in JP-A 2007-145797, paragraphs [0102]-[0113], JP-A 2008-111103, paragraphs [0122]-[0142], JP-A 2014-001259, paragraphs [0081]-[0092], JP-A 2012-041320, JP-A 2012-153644, JP-A 2012-106986, and JP-A 2016-018007. The PAGs capable of generating partially fluorinated sulfonic acid as described in these patent documents are preferably used in the ArF lithography because the generated acid has an adequate strength and diffusion length.

As the second PAG, those having the formula (6) are preferred.

(6)

In formula (6), $R^{101}$, $R^{102}$ and $R^{103}$ are each independently a $C_1$-$C_{20}$ straight, branched or cyclic monovalent hydrocarbon group which may contain a heteroatom. Any two of $R^{101}$, $R^{102}$ and $R^{103}$ may bond together to form a ring with the sulfur atom to which they are attached. Preferably at least one of $R^{101}$, $R^{102}$ and $R^{103}$ is an aromatic ring-containing group. With respect to the sulfonium cation in formula (6), reference should be made to JP-A 2014-001259, paragraphs [0082]-[0085]. Examples of the sulfonium cation include those cations described in JP-A 2007-145797, paragraphs [0027]-[0033], JP-A 2010-113209, paragraphs [0059], JP-A 2012-041320, JP-A 2012-153644, and JP-A 2012-106986.

Examples of the sulfonium cation in formula (6) are shown below, but not limited thereto.

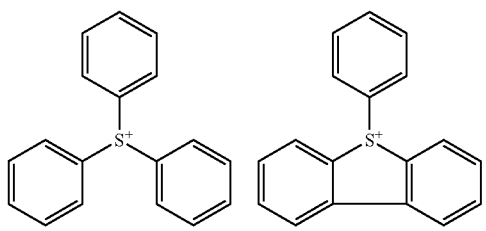

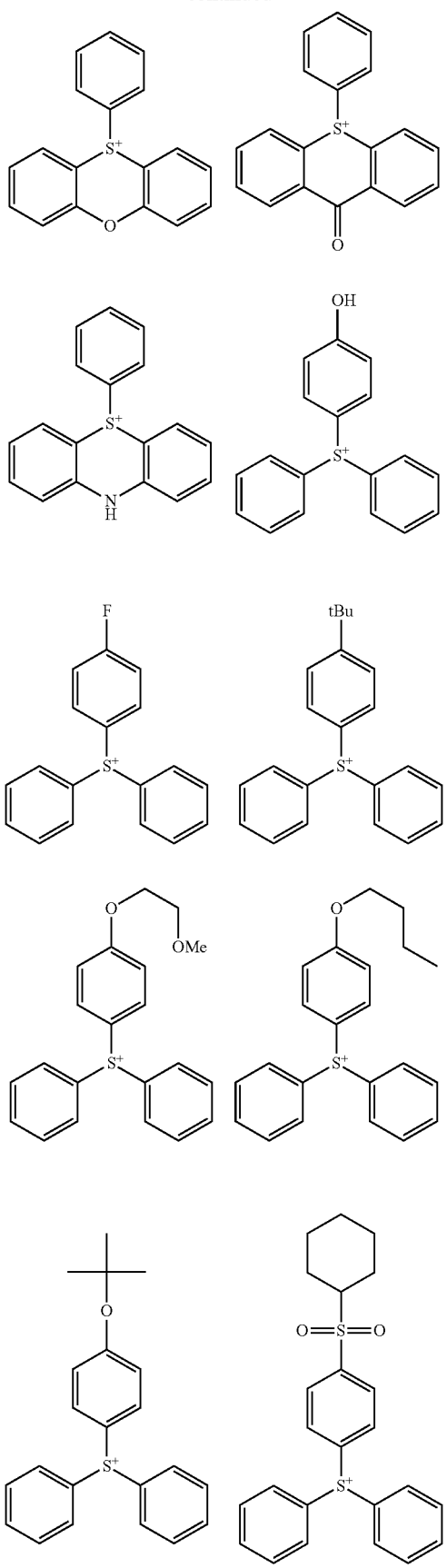
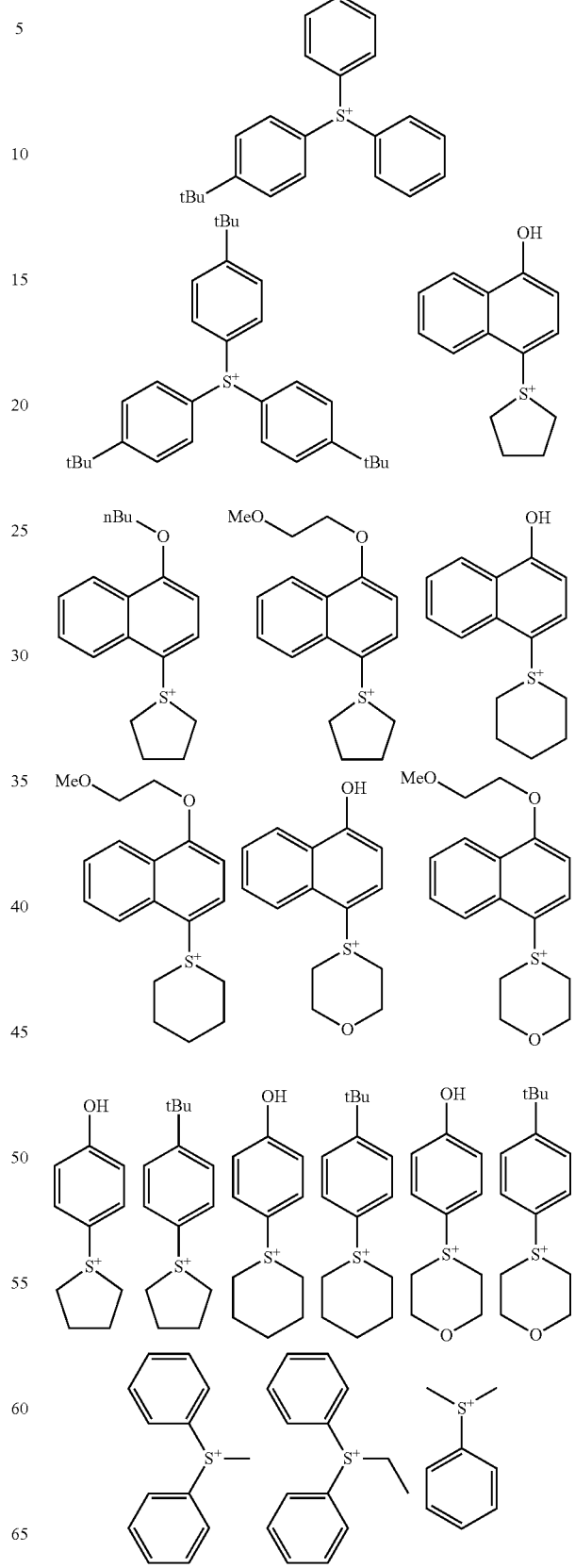

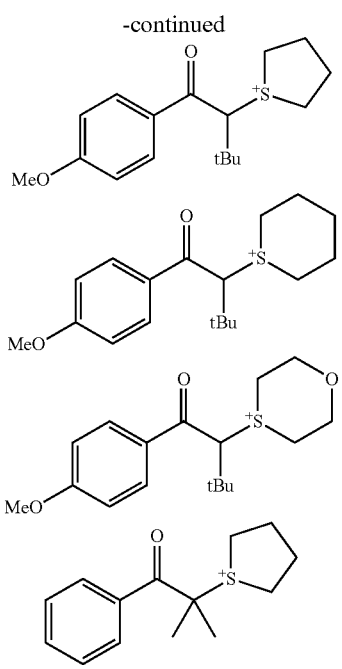

In formula (6), X is an anion selected from the formulae (6A) to (6D).

$$R^{fa}—CF_2—SO_3^-  \quad (6A)$$

$$\begin{array}{l}R^{fb1}—CF_2—SO_2\\R^{fb2}—CF_2—SO_2\end{array}\!\!\!\!\!\!\!N^- \quad (6B)$$

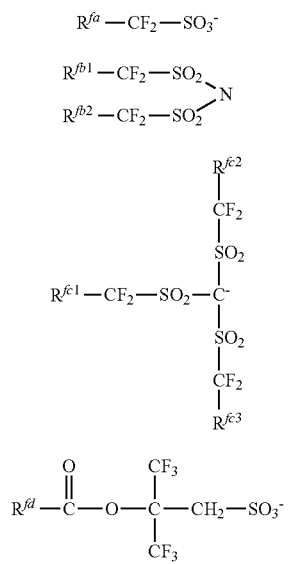

(6D)

$$R^{fd}—\underset{\underset{O}{\|}}{C}—O—\underset{\underset{CF_3}{|}}{\overset{\overset{CF_3}{|}}{C}}—CH_2—SO_3^-$$

In formula (6A), $R^{fa}$ is fluorine or a $C_1$-$C_{40}$ straight, branched or cyclic monovalent hydrocarbon group which may contain a heteroatom.

Of the anions of formula (6A), a structure having formula (6A') is preferred.

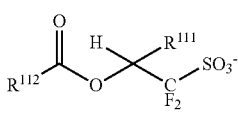

(6A')

In formula (6A'), $R^{111}$ is hydrogen or trifluoromethyl, preferably trifluoromethyl. $R^{112}$ is a $C_1$-$C_{35}$ straight, branched or cyclic monovalent hydrocarbon group which may contain a heteroatom. Of the monovalent hydrocarbon groups, those of 6 to 35 carbon atoms are preferred because a high resolution is available in fine pattern formation. Suitable monovalent hydrocarbon groups include, but are not limited to, methyl, ethyl, propyl, isopropyl, butyl, isobutyl, s-butyl, t-butyl, pentyl, neopentyl, cyclopentyl, hexyl, cyclohexyl, 3-cyclohexenyl, heptyl, 2-ethylhexyl, nonyl, undecyl, tridecyl, pentadecyl, heptadecyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl, icosanyl, allyl, benzyl, diphenylmethyl, tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl as well as those exemplified above for $R^{11}$.

With respect to the anion of formula (6A'), reference is made to JP-A 2007-145797, JP-A 2008-106045, JP-A 2009-007327, JP-A 2009-258695, and JP-A 2012-181306. Examples of the anion of formula (6A') include the anions described in these patent documents and the anions exemplified above for formulae (3), (4) and (5).

In formula (6B), $R^{fb1}$ and $R^{fb2}$ are each independently fluorine or a $C_1$-$C_{40}$ straight, branched or cyclic monovalent hydrocarbon group which may contain a heteroatom. Suitable monovalent hydrocarbon groups are as exemplified above for $R^{112}$. Preferably $R^{fb1}$ and $R^{fb2}$ each are fluorine or a $C_1$-$C_4$ straight fluorinated alkyl group. A pair of $R^{fb1}$ and $R^{fb2}$ may bond together to form a ring with the linkage (—$CF_2$—$SO_2$—$N^-$—$SO_2$—$CF_2$—) to which they are attached, and preferably the pair is a fluorinated ethylene or fluorinated propylene group forming a ring structure.

In formula (6C), $R^{fc1}$, $R^{fc2}$ and $R^{fc3}$ are each independently fluorine or a $C_1$-$C_{40}$ straight, branched or cyclic monovalent hydrocarbon group which may contain a heteroatom. Suitable monovalent hydrocarbon groups are as exemplified above for $R^{112}$. Preferably $R^{fc1}$, $R^{fc2}$ and $R^{fc3}$ each are fluorine or a $C_1$-$C_4$ straight fluorinated alkyl group. A pair of $R^{fc1}$ and $R^{fc2}$ may bond together to form a ring with the linkage (—$CF_2SO_2$—$C^-$—$SO_2$—$CF_2$—) to which they are attached, and preferably the pair is a fluorinated ethylene or fluorinated propylene group forming a ring structure.

In formula (6D), $R^{fd}$ is a $C_1$-$C_{40}$ straight, branched or cyclic monovalent hydrocarbon group which may contain a heteroatom. Suitable monovalent hydrocarbon groups are as exemplified above for $R^{112}$. With respect to the anion of formula (6D), reference is made to JP-A 2010-215608 and JP-A 2014-133723. Examples of the anion of formula (6D) include the anions described in these patent documents and the anions exemplified above for formulae (3), (4) and (5). The compound having the anion of formula (6D) has a sufficient acid strength to cleave acid labile groups on the resist polymer because it is free of fluorine at α-position of sulfo group, but has two trifluoromethyl groups at β-position. Thus the compound is a useful PAG.

Examples of the anion represented by X⁻ are shown below, but not limited thereto. Herein "A" is hydrogen or trifluoromethyl.

-continued
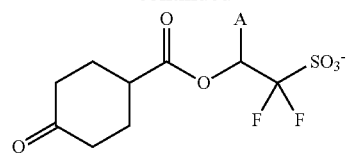
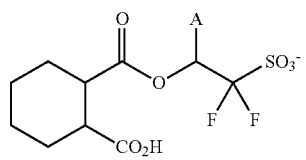
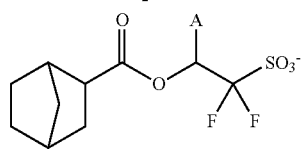
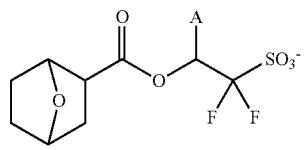
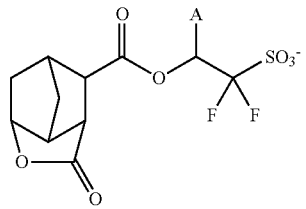
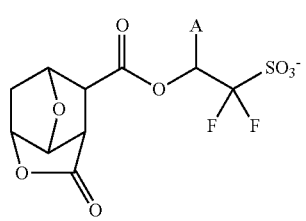
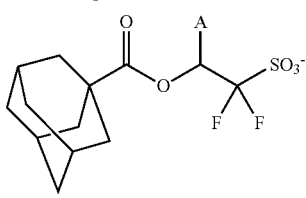
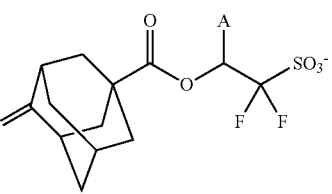
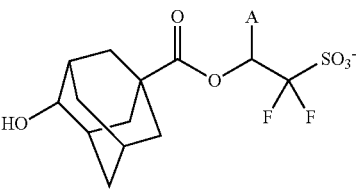
-continued
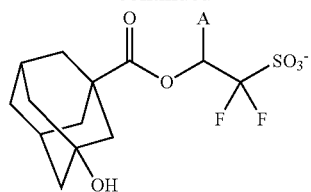
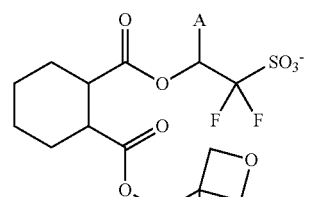
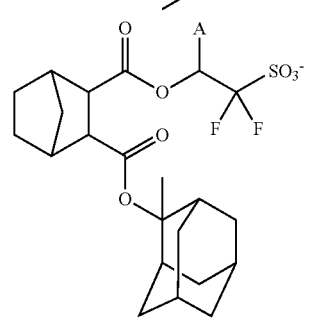
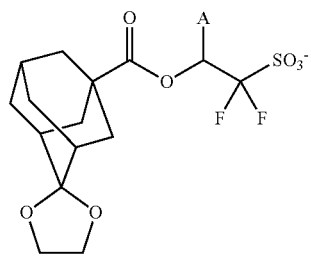
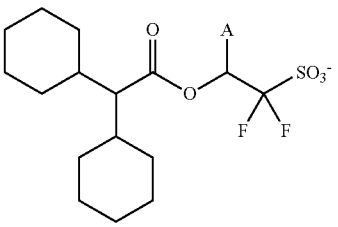
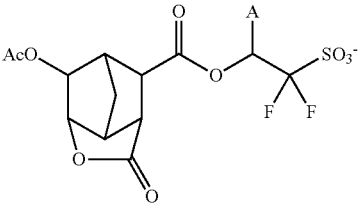
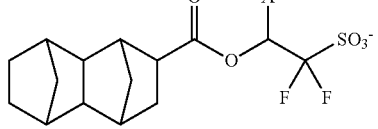

93
-continued
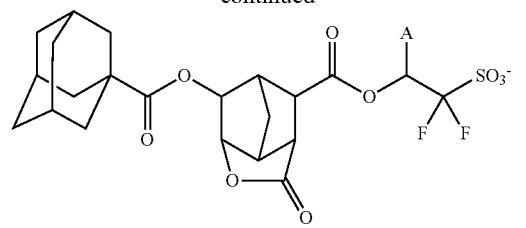
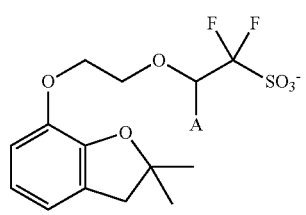
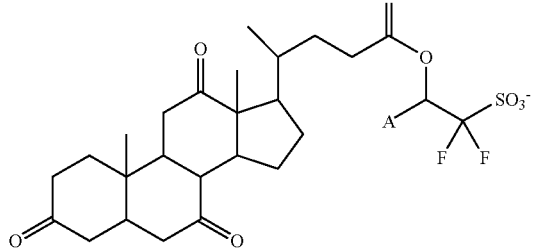
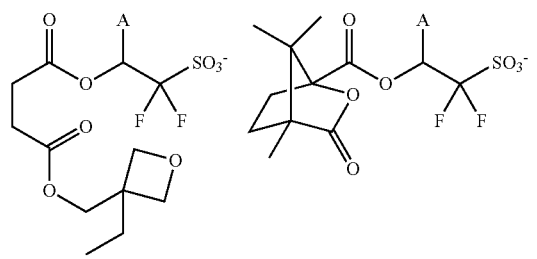
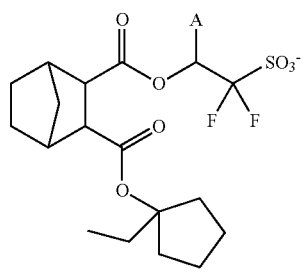
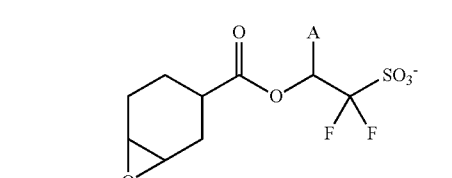
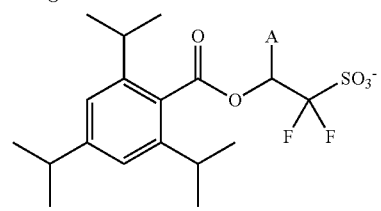
94
-continued
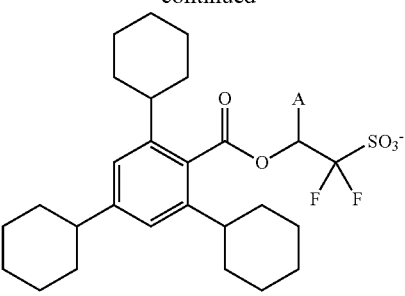
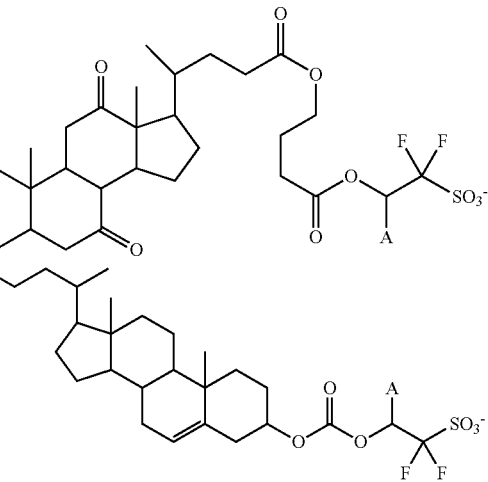
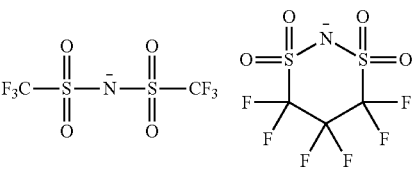
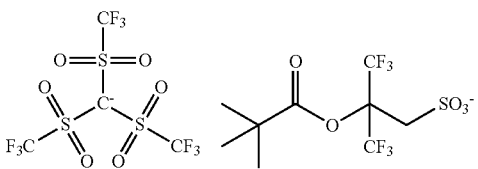
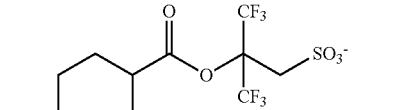
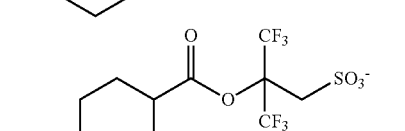
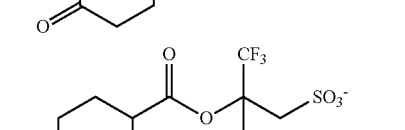
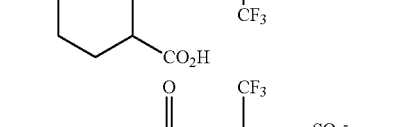
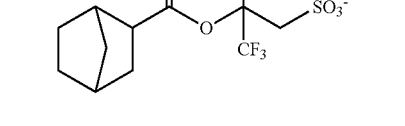

-continued
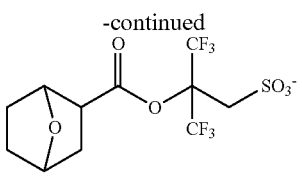
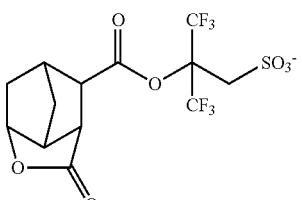
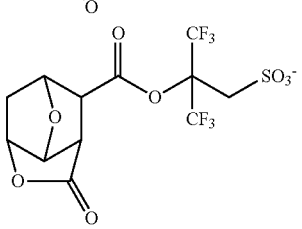
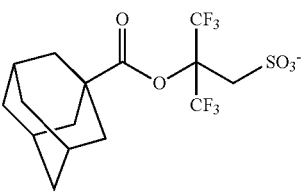
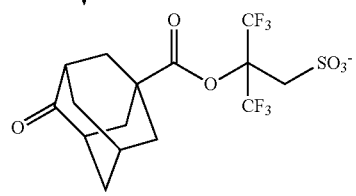
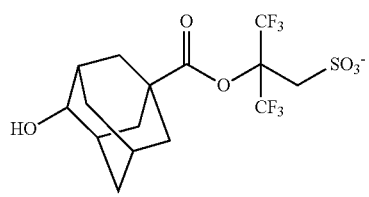
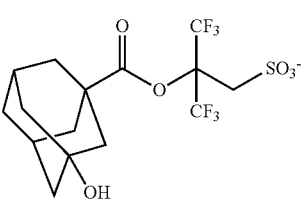
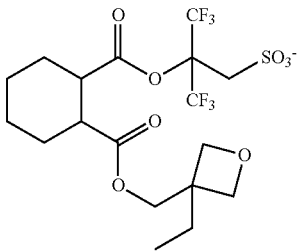
-continued
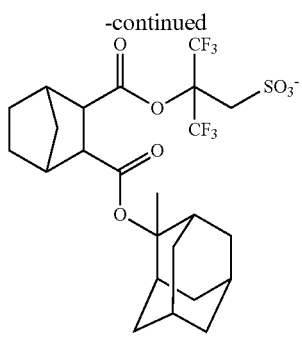
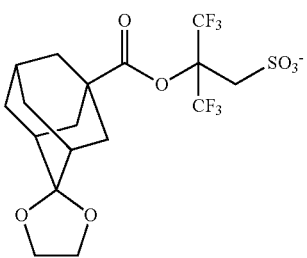
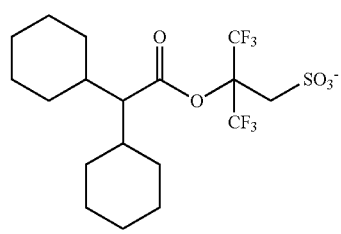
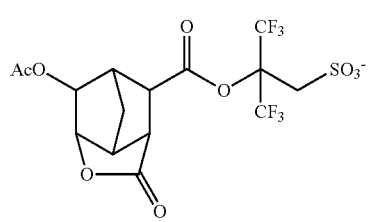
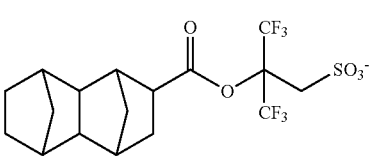
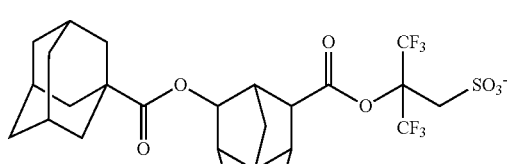
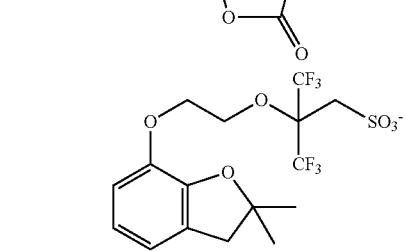

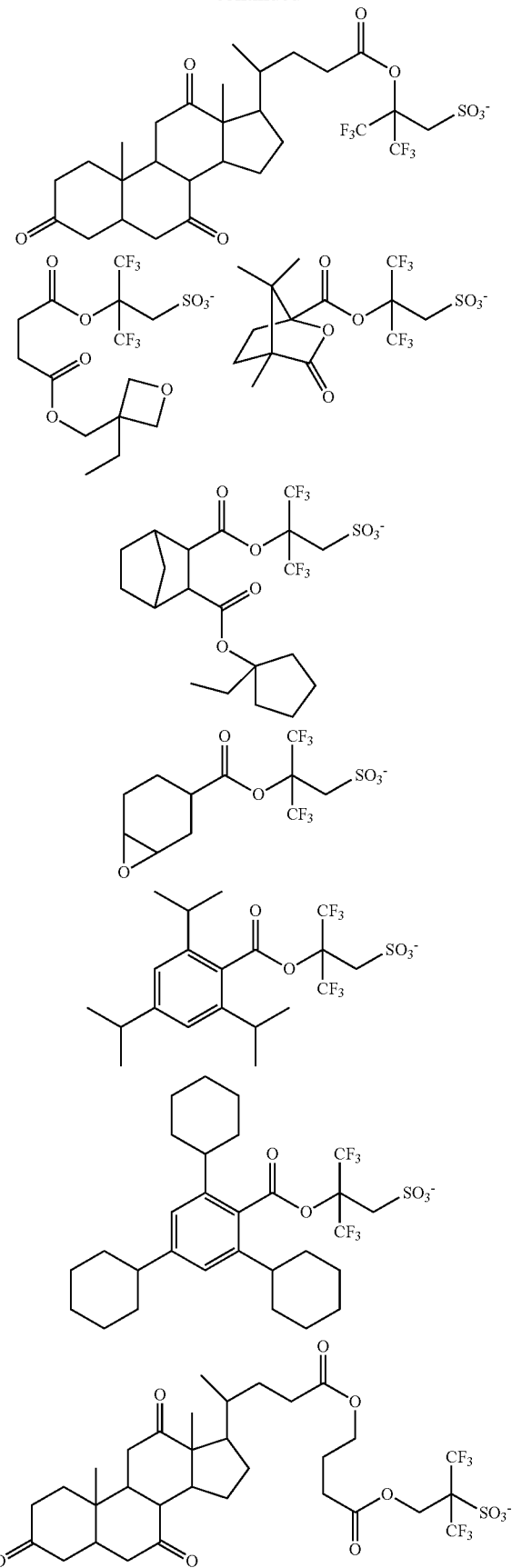

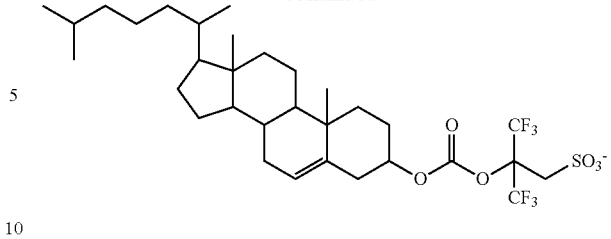

Exemplary structures for the sulfonium salt of formula (6) include arbitrary combinations of anions with cations, both as exemplified above.

As the second PAG (D), those having the formula (7) are also preferred.

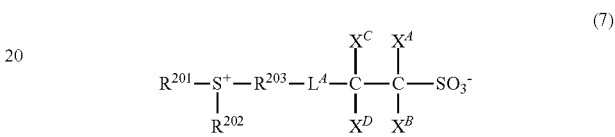
(7)

In formula (7), $R^{201}$ and $R^{202}$ are each independently a $C_1$-$C_{30}$ straight, branched or cyclic monovalent hydrocarbon group which may contain a heteroatom. $R^{203}$ is a $C_1$-$C_{30}$ straight, branched or cyclic divalent hydrocarbon group which may contain a heteroatom. Any two of $R^{201}$, $R^{202}$ and $R^{203}$ may bond together to form a ring with the sulfur atom in the formula. $L^A$ is a single bond, ether group, or a $C_1$-$C_{20}$ straight, branched or cyclic divalent hydrocarbon group which may contain a heteroatom. $X^A$, $X^B$, $X^C$ and $X^D$ are each independently hydrogen, fluorine or trifluoromethyl, at least one of $X^A$, $X^B$, $X^C$ and $X^D$ being fluorine or trifluoromethyl.

Of the compounds having formula (7), those having formula (7') are preferred.

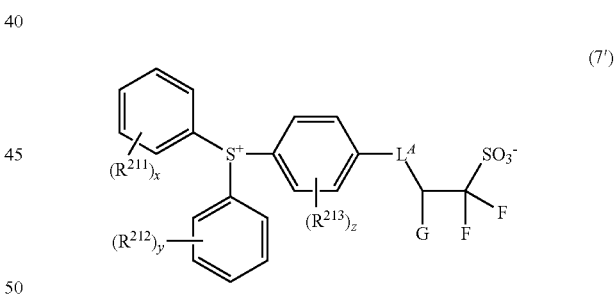
(7')

In formula (7'), $L^A$ is as defined above. G is hydrogen or trifluoromethyl, preferably trifluoromethyl. $R^{211}$, $R^{212}$ and $R^{213}$ are each independently hydrogen or a $C_1$-$C_{20}$ straight, branched or cyclic monovalent hydrocarbon group which may contain a heteroatom, x and y are each independently an integer of 0 to 5, and z is an integer of 0 to 4.

In formulae (7) and (7'), $L^A$ is preferably an ether group or $Q_X$-O-$L^{A'}$-$Q_Y$ wherein $Q_X$ depicts a bond to the benzene ring, $Q_Y$ depicts a bond to —CH(G)-$CF_2$—$SO_3^-$, and $L^{A'}$ is a $C_1$-$C_{10}$ straight, branched or cyclic divalent hydrocarbon group which may contain a heteroatom.

With respect to the PAGs of formula (7) or (7'), reference is made to JP-A 2011-016746. Examples of these PAGs include the sulfonium compounds described in JP-A 2015-214634, paragraphs [0149]-[0150] as well as JP-A 2011-016746.

Examples of the PAG having formula (7) are given below, but not limited thereto. Herein G is as defined above.
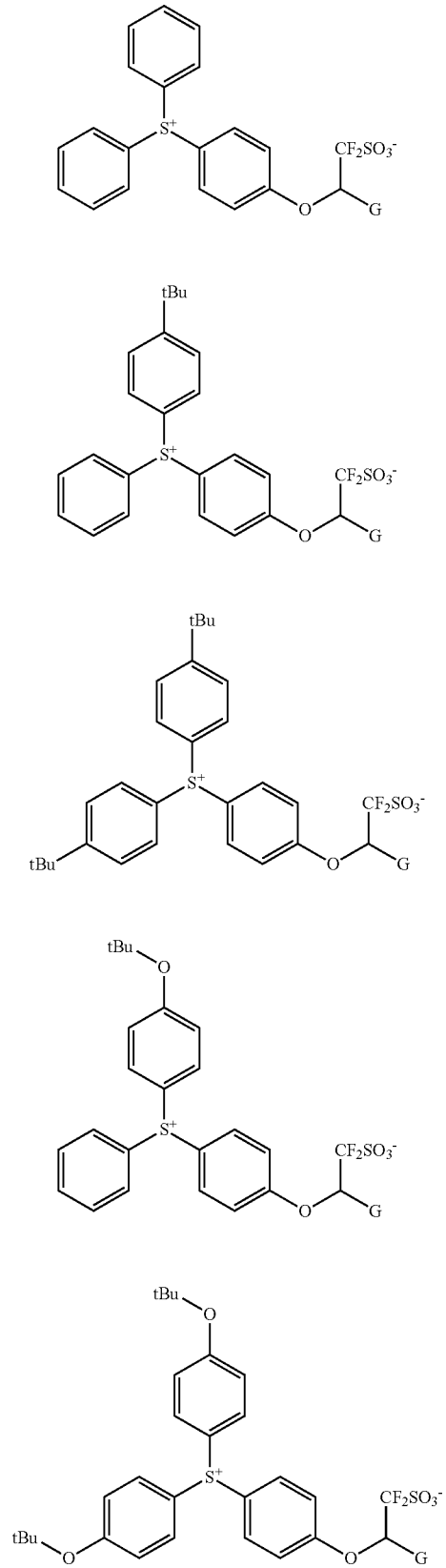
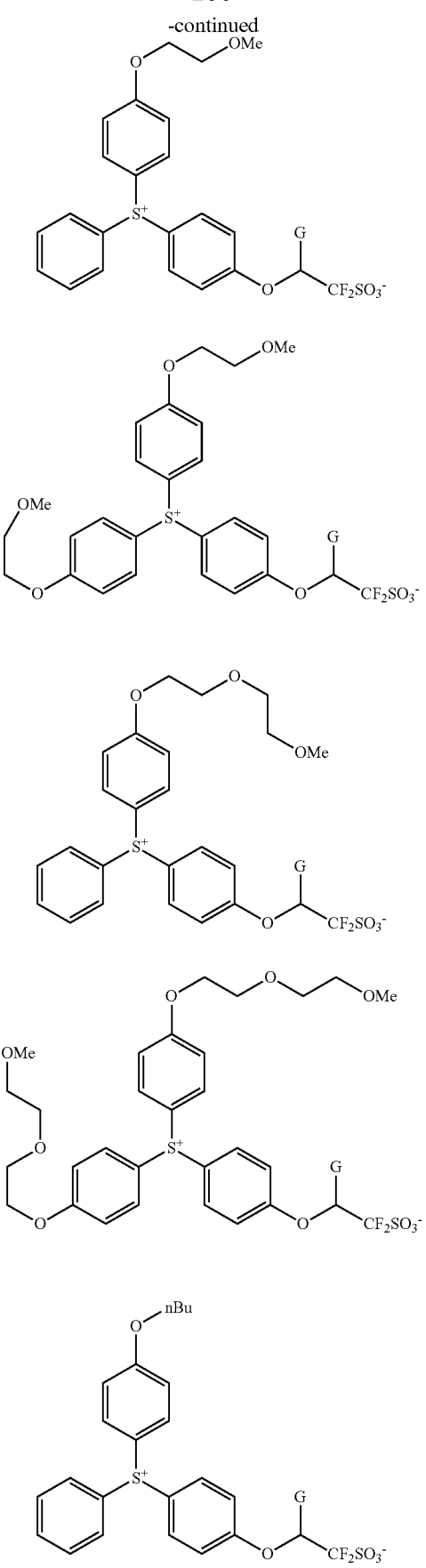

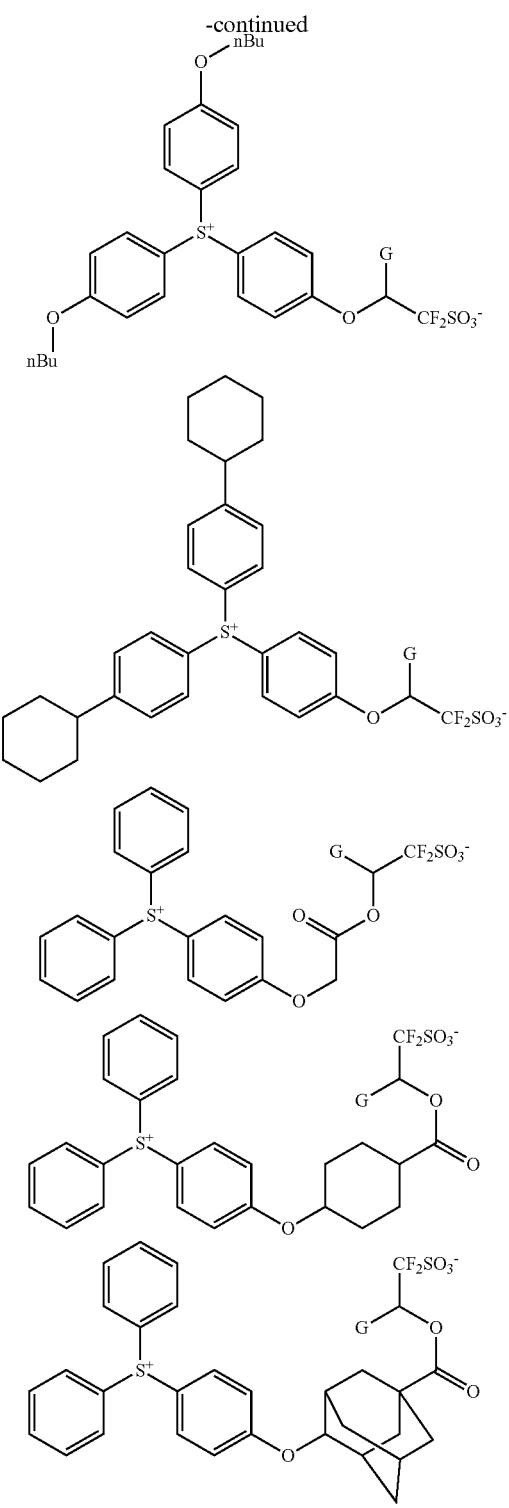

weight. An amount in the range ensures good resolution and leaves no foreign particles after resist development or during separation.

(E) Quencher

The resist composition may further comprise (E) a quencher if necessary. As used herein, the "quencher" refers to a compound capable of suppressing the rate of diffusion when the acid generated by the PAG diffuses within the resist film.

Typical of the quencher are amine compounds. Suitable quenchers include primary, secondary and tertiary amine compounds, specifically amine compounds having a hydroxyl, ether, ester, lactone ring, cyano or sulfonate group, as described in JP-A 2008-111103, paragraphs [0146]-[0164] (U.S. Pat. No. 7,537,880), and compounds having primary or secondary amine protected as a carbamate group, as described in JP 3790649. The protected amine compounds are effective where the resist composition contains a base labile component.

Also an onium salt of sulfonic acid which is not fluorinated at α-position or carboxylic acid as represented by the formula (8) or (9) is useful as the quencher.

Herein $R^{q1}$ is hydrogen or a $C_1$-$C_{40}$ straight, branched or cyclic monovalent hydrocarbon group which may contain a heteroatom, exclusive of the hydrocarbon group in which hydrogen bonded to the carbon atom at α-position relative to the sulfo group is replaced by fluorine or fluoroalkyl. $R^{q2}$ is hydrogen or a $C_1$-$C_{40}$ straight, branched or cyclic monovalent hydrocarbon group which may contain a heteroatom. $Mq^+$ is an onium cation.

In formula (8), examples of the group $R^{q1}$ include the same structures as illustrated for $R^{11}$ in formula (3). In formula (9), examples of the group $R^{q2}$ include the same structures as illustrated for $R^{11}$ in formula (3). Also included are fluorinated alkyl groups such as trifluoromethyl, trifluoroethyl, 2,2,2-trifluoro-1-methyl-1-hydroxyethyl, 2,2,2-trifluoro-1-(trifluoromethyl)-1-hydroxyethyl; aryl groups such as phenyl, tolyl, xylyl, 4-tert-butylphenyl and naphthyl; and fluorinated aryl groups such as pentafluorophenyl and 4-trifluoromethylphenyl.

The onium salts having formulae (8) and (9) are described in JP-A 2008-158339, JP-A 2010-155824, and JP 3991462. Exemplary structures of these onium salts include the structures described in these patent documents.

Suitable structures of the anion moiety in the onium salt having formula (8) or (9) are shown below, but not limited thereto.

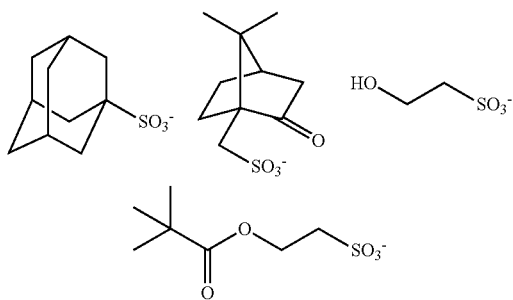

Of the foregoing PAGs, those having an anion of formula (6A') or (6D) are more preferred because of reduced acid diffusion and high solvent solubility. Also those having a structure of formula (7') are more preferred because of minimal acid diffusion.

An appropriate amount of the PAG (D) added is 0 to 40 parts by weight per 100 parts by weight of the base resin (B). When added, the amount of the PAG (D) is more preferably 0.1 to 30 parts, and even more preferably 0.5 to 20 parts by 103
-continued
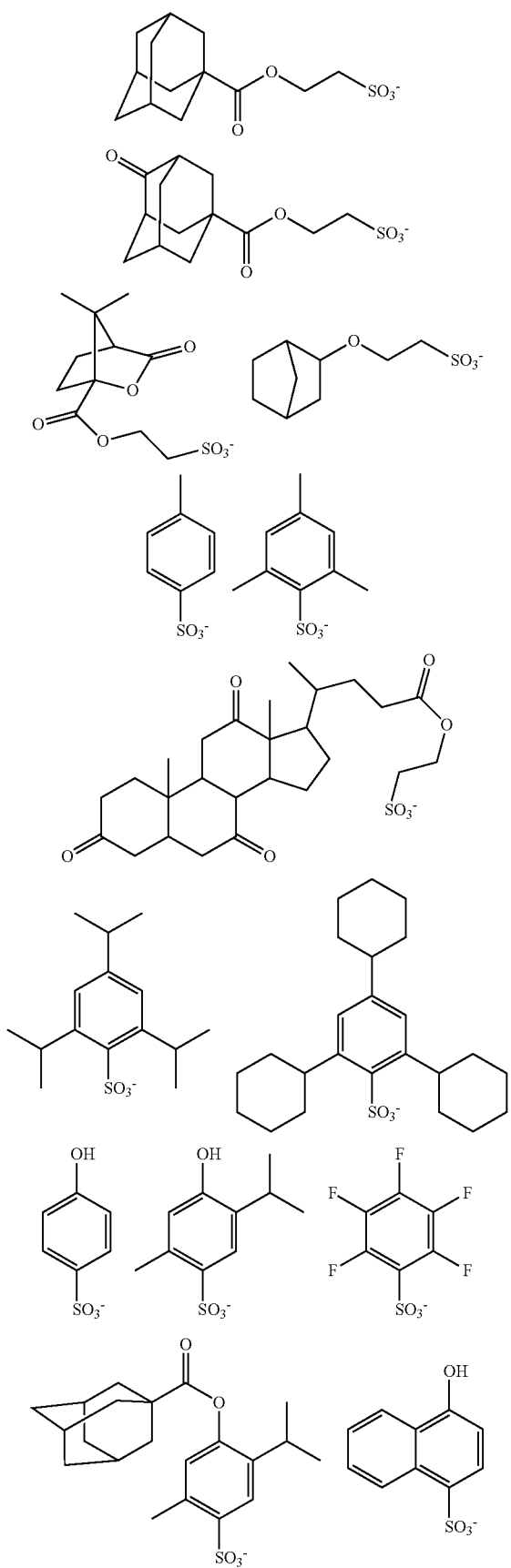
104
-continued
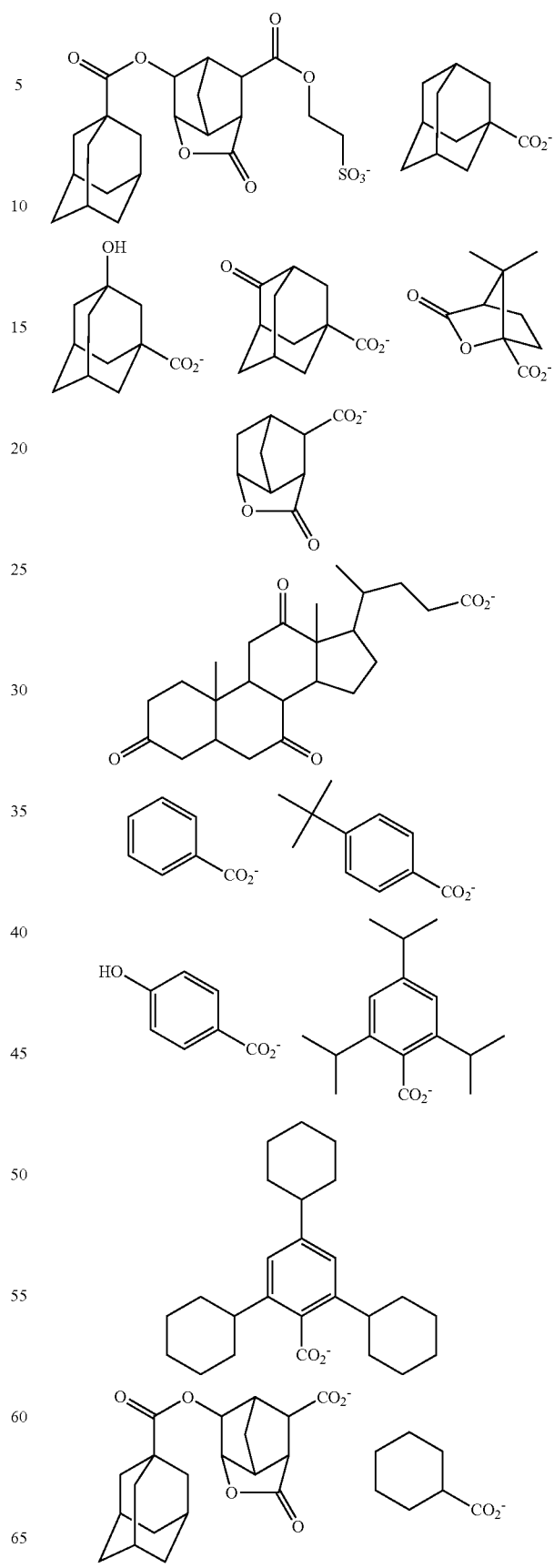

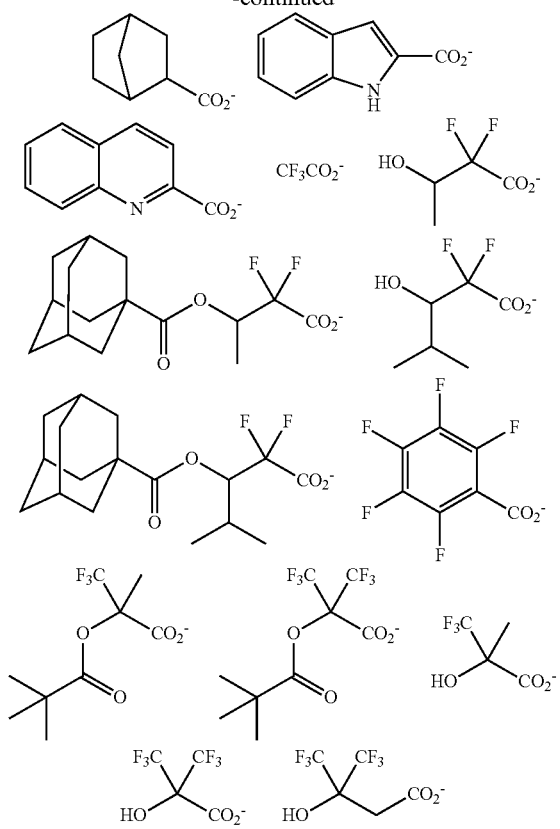
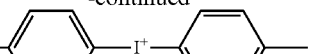
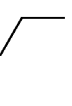
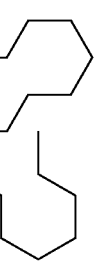
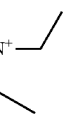

As the onium cation in formulae (8) and (9), those having the following formulae (10), (11) and (12) are preferred.

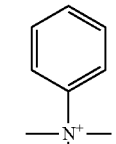 (10)

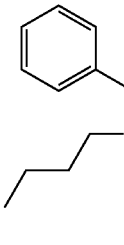 (11) (12)

Herein $R^{151}$ to $R^{158}$ are each independently a $C_1$-$C_{20}$ straight, branched or cyclic monovalent hydrocarbon group which may contain a heteroatom. $R^{151}$ and $R^{152}$ may bond together to form a ring with the sulfur atom to which they are attached. $R^{156}$ and $R^{157}$ may bond together to form a ring with the nitrogen atom to which they are attached.

Examples of the onium cation include those exemplified above as the sulfonium cation in the PAG having formula (6) and those shown below, but are not limited thereto.

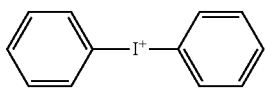

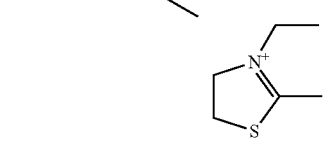
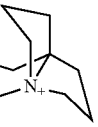
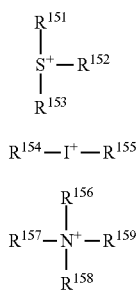

Exemplary structures for the onium salt having formula (8) or (9) include arbitrary combinations of cations with anions, both as exemplified above. It is noted that these onium salts may be readily prepared by ion exchange reaction using the well-known organic chemistry technique. With respect to the ion exchange reaction, reference is made to JP-A 2007-145797.

The onium salt having formula (8) or (9) functions as a quencher since the anion therein is a conjugated base of weak acid. As used herein, the weak acid indicates an acidity insufficient to deprotect an acid labile group from an acid labile group-containing unit in the base resin. The onium salt having formula (8) or (9) functions as a quencher when used in combination with an onium salt type PAG having a conjugated base of a strong acid, typically a sulfonic acid which is fluorinated at α-position as the counter anion. In a system using a mixture of an onium salt capable of generating a strong acid (e.g., α-position fluorinated sulfonic acid) and an onium salt capable of generating a weak acid (e.g., α-position non-fluorinated sulfonic acid or carboxylic acid), if the strong acid generated from the PAG upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion. That is, the onium salt functions as a quencher.

In particular, since those onium salts having formula (8) or (9) wherein Mq$^+$ is a sulfonium cation (10) or iodonium cation (11) are photo-decomposable, those portions receiving a high light intensity are reduced in quenching capability and increased in the concentration of a strong acid generated by the PAG. This enables to form a pattern having an improved contrast in exposed area, further improved DOF and satisfactory dimensional control.

If a photoacid generator capable of generating a strong acid is an onium salt, an exchange from the strong acid generated upon exposure to high-energy radiation to a weak acid as above can take place, but it rarely happens that the weak acid generated upon exposure to high-energy radiation collides with the unreacted onium salt capable of generating a strong acid to induce a salt exchange. This is because of a likelihood of an onium cation forming an ion pair with a stronger acid anion.

In case the acid labile group is an acetal group which is very sensitive to acid, the acid for eliminating the protective group need not necessarily be an α-fluorinated sulfonic acid, imide acid or methide acid. Sometimes, deprotection reaction may take place even with α-position non-fluorinated sulfonic acid. In this case, an onium salt of carboxylic acid having formula (9) is preferably used as the quencher.

Besides the quenchers of onium salt type mentioned above, a quencher of betaine type may also be used, for example, diphenyliodonium 2-carboxylate which is one of well-known betaine compounds.

Also a photo-decomposable onium salt having a nitrogen-containing substituent group may be used in combination with the onium salt having formula (8) or (9) as the quencher (E). This compound functions as a quencher in the unexposed region, but as a so-called photo-degradable base in the exposed region because it loses the quencher function in the exposed region due to neutralization thereof with the acid generated by itself. Using a photo-degradable base, the contrast between exposed and unexposed regions can be further enhanced. With respect to the photo-degradable base, reference may be made to JP-A 2009-109595, 2012-046501, and JP-A 2013-209360, for example.

The quencher (B) may be used alone or in admixture of two or more. An appropriate amount of the quencher is 0 to 40 parts by weight per 100 parts by weight of the base resin (B). When used, the amount is preferably 0.1 to 40 parts, more preferably 05 to 20 parts by weight. The inclusion of quencher within the range facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile. The inclusion of quencher is also effective for improving adhesion to the substrate.

(F) Surfactant

The resist composition may further comprise (F) a surfactant which is insoluble or substantially insoluble in water and soluble in alkaline developer, and/or a surfactant which is insoluble or substantially insoluble in water and alkaline developer. The surfactant may be used in an ordinary amount a long as the benefits of the invention are not impaired. For the surfactant, reference should be made to those compounds described in JP-A 2010-215608 and JP-A 2011-016746.

While many examples of the surfactant which is insoluble or substantially insoluble in water and alkaline developer are described in the patent documents cited herein, preferred examples are FC-4430, Surflon® S-381, Surfynol® E1004, KH-20 and KH-30, which may be used alone or in admixture. Partially fluorinated oxetane ring-opened polymers having the formula (surf-1) are also useful.

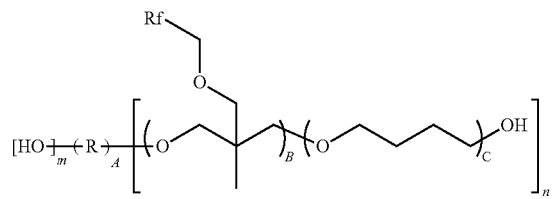

(surf-1)

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

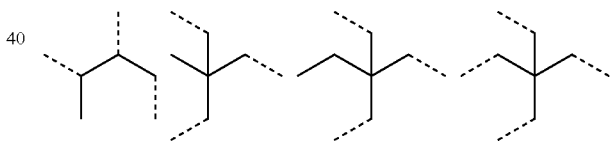

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of m and n, which represents the valence of R, is an integer of 2 to 4. A is equal to 1, B is an integer of 2 to 25, and C is an integer of 0 to 10. Preferably, B is an integer of 4 to 20, and C is 0 or 1. Note that the formula (surf-1) does not prescribe the arrangement of respective constituent units while they may be arranged either blockwise or randomly. For the preparation of surfactants in the form of partially fluorinated oxetane ring-opened polymers, reference should be made to U.S. Pat. No. 5,650,483, for example.

The surfactant which is insoluble or substantially insoluble in water and soluble in alkaline developer is useful when ArF immersion lithography is applied to the resist composition in the absence of a resist protective film. In this embodiment, the surfactant has a propensity to segregate on the resist surface after spin coating for achieving a function of minimizing water penetration or leaching. The surfactant is also effective for preventing water-soluble components from being leached out of the resist film for minimizing any damage to the exposure tool. The surfactant becomes solubilized during alkaline development following exposure and PEB, and thus forms few or no foreign particles which become defects. The preferred surfactant is a polymeric surfactant which is insoluble or substantially insoluble in water, but soluble in alkaline developer, also referred to as "hydrophobic resin" in this sense, and especially which is water repellent and enhances water slippage.

Suitable polymeric surfactants are shown below.

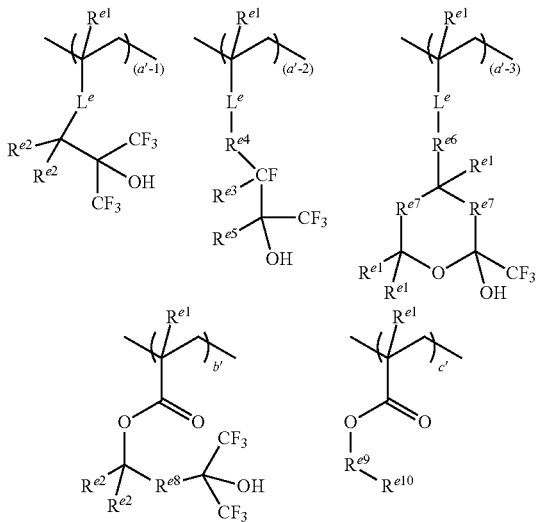

Herein $R^{e1}$ is each independently hydrogen, fluorine, methyl or trifluoromethyl. $R^{e2}$ is each independently hydrogen or a straight, branched or cyclic $C_1$-$C_{20}$ alkyl or fluoroalkyl group, or two $R^{e2}$ in a common unit may bond together to form a ring with the carbon atom to which they are attached, and in this event, they together represent a straight, branched or cyclic $C_2$-$C_{20}$ alkylene or fluoroalkylene group.

$R^{e3}$ is fluorine or hydrogen, or $R^{e3}$ may bond with $R^{e4}$ to form a non-aromatic ring of 3 to 10 carbon atoms in total with the carbon atom to which they are attached. $R^{e4}$ is a straight, branched or cyclic $C_1$-$C_6$ alkylene group in which at least one hydrogen atom may be substituted by a fluorine atom. $R^{e5}$ is a straight or branched $C_1$-$C_{10}$ alkyl group in which at least one hydrogen atom is substituted by a fluorine atom. Alternatively, $R^{e4}$ and $R^{e5}$ may bond together to form a non-aromatic ring with the carbon atoms to which they are attached. In this event, $R^{e4}$, $R^{e5}$ and the carbon atoms to which they are attached together represent a trivalent organic group of 3 to 12 carbon atoms in total. $R^{e6}$ is a single bond or a $C_1$-$C_4$ alkylene.

$R^{e7}$ is each independently a single bond, —O—, or —$CR^{e1}R^{e1}$—. $R^{e8}$ is a $C_1$-$C_4$ straight or branched alkylene group, or may bond with $R^{e2}$ within a common unit to form a $C_3$-$C_6$ non-aromatic ring with the carbon atom to which they are attached. $R^{e9}$ is 1,2-ethylene, 1,3-propylene or 1,4-butylene.

$R^{e10}$ is a $C_3$-$C_6$ linear perfluoroalkyl group, typically 3H-perfluoropropyl, 4H-perfluorobutyl, 5H-perfluoropentyl or 6H-perfluorohexyl. $L^e$ is each independently —C(=O)—O—, —O—, or —C(=O)—$R^{e11}$—C(=O)—O—. $R^{e11}$ is a straight, branched or cyclic $C_1$-$C_{10}$ alkylene group. The subscripts are in the range: 0≤(a'-1)≤1, 0≤(a'-2)≤1, 0≤(a'-3)≤1, 0≤b'≤1, 0≤c'≤1, and 0<(a'-1)+(a'-2)+(a'-3)+b'+c'≤1.

For the surfactant which is insoluble or substantially insoluble in water and soluble in alkaline developer, reference may be made to JP-A 2007-297590, JP-A 2008-088343, JP-A 2008-111103, JP-A 2008-122932, JP-A 2009-098638, JP-A 2009-191151, JP-A 2009-192784, JP-A 2009-276363, JP-A 2010.107695, JP-A 2010-134012, JP-A 2010-250105, and JP-A 2011-042789.

An appropriate amount of the polymeric surfactant is 0.001 to 20 parts, more preferably 0.01 to 10 parts by weight per 100 parts by weight of the base resin (B). For the detail of the polymeric surfactant, reference is made to JP-A 2007-297590.

Other Component (G)

Another component (G) may be added to the resist composition. Such additives include a compound which is decomposed with an acid to generate another acid (acid amplifier compound), an organic acid derivative, a fluorinated alcohol, a crosslinker, a compound having a Mw of up to 3,000 which changes its solubility in alkaline developer under the action of an acid (dissolution inhibitor), and an acetylene alcohol. For the acid amplifier compound, reference should be made to JP-A 2009-269953 and JP-A 2010-215608. In the resist composition, an appropriate amount of the acid amplifier compound is 0 to 5 parts, and especially 0 to 3 parts by weight per 100 parts by weight of the base resin (B). Excessive amounts of the acid amplifier compound may make diffusion control difficult, leading to degradation of resolution and pattern profile. With respect to the other additives, reference may be made to JP-A 2008-122932, paragraphs [0155]-[0182], JP-A 2009-269953 and JP-A 2010-215608.

Process

A further embodiment of the invention is a pattern forming process using the resist composition defined above. A pattern may be formed from the resist composition using any well-known lithography process. The preferred process includes at least the steps of forming a resist film on a substrate, exposing it to high-energy radiation, and developing it in a developer.

Specifically, the resist composition is applied onto a substrate for integrated circuitry fabrication (e.g., Si, $SiO_2$, SiN, SiON, TiN, WSi, BPSG, SOG, organic antireflective film, etc.) or a substrate for mask circuitry fabrication (e.g., Cr, CrO, CrON, $MoSi_2$, $SiO_2$, etc.) by a suitable coating technique such as spin coating. The coating is prebaked on a hotplate at a temperature of 60 to 150° C. for 1 to 10 minutes, preferably 80 to 140° C. for 1 to 5 minutes. The resulting resist film is generally 0.05 to 2 μm thick.

Through a photomask having a desired pattern disposed over the substrate, the resist film is then exposed to high-energy radiation such as KrF excimer laser, ArF excimer laser or EUV in an exposure dose preferably in the range of 1 to 200 mJ/cm², more preferably 10 to 100 mJ/cm². Alternatively, pattern formation may be performed by writing with EB directly in a dose of preferably 1 to 300 μC/cm², more preferably 10 to 200 μC/cm². Light exposure may be done by a conventional lithography process or in some cases, by an immersion lithography process of providing a liquid having a refractive index of at least 1.0 between the projection lens and the resist film. The preferred liquid is water. In the case of immersion lithography using water, a protective film which is insoluble in water may be formed on the resist film.

The resist film is then baked (PEB) on a hotplate at 60 to 150° C. for 1 to 5 minutes, and preferably at 80 to 140° C. for 1 to 3 minutes. Finally, development is carried out using an aqueous alkaline solution, such as a 0.1 to 5 wt %, preferably 2 to 3 wt %, aqueous solution of tetramethylammonium hydroxide (TMAH), or an organic solvent as the developer, this being done by a conventional method such as dip, puddle, or spray development for a period of 0.1 to 3 minutes, and preferably 0.5 to 2 minutes. In this way the desired pattern is formed on the substrate. The invention is not limited to the process described above, and any steps may be added if necessary.

With respect to the formation of a positive pattern via development in an alkaline aqueous solution, reference is made to U.S. Pat. No. 8,647,808 (JP-A 2011-231312, paragraphs [0138]-[0146]). With respect to the formation of a negative pattern via organic solvent development, reference is made to U.S. Pat. No. 9,256,127 (JP-A 2015-214634, paragraphs [0173]-[0183])

While the water-insoluble protective film which is used in the immersion lithography serves to prevent any components from being leached out of the resist film and to improve water slippage at the film surface, it is generally divided into two types. The first type is an organic solvent-strippable protective film which must be stripped, prior to alkaline development, with an organic solvent in which the resist film is not dissolvable. The second type is an alkali-soluble protective film which is soluble in an alkaline developer so that it can be removed simultaneously with the removal of solubilized regions of the resist film. The protective film of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

Any desired step may be added to the pattern forming process. For example, after a photoresist film is formed, a step of rinsing with pure water (post-soaking) may be introduced to extract the acid generator or the like from the film surface or wash away particles. After exposure, a step of rinsing (post-soaking) may be introduced to remove any water remaining on the film after exposure.

A pattern may also be formed by a double patterning process. The double patterning process includes a trench process of processing an underlay to a 1.3 trench pattern by a first step of exposure and etching, shifting the position, and forming a 1:3 trench pattern by a second step of exposure for forming a 1:1 pattern; and a line process of processing a first underlay to a 1:3 isolated left pattern by a first step of exposure and etching, shifting the position, processing a second underlay formed below the first underlay by a second step of exposure through the 1:3 isolated left pattern, for forming a half-pitch 1:1 pattern.

Where a hole pattern is formed by negative tone development using organic solvent developer, exposure by double dipole illuminations of X- and Y-direction line patterns provides the highest contrast light. The contrast may be further increased by combining two dipole illuminations of X- and Y-direction line patterns with s-polarized illumination. These pattern forming processes are described in JP-A 2011-221513.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is at a temperature of 70 to 180° C., preferably 80 to 170° C., for a time of 10 to 300 seconds. The extra shrink agent is stripped and the hole pattern is shrunk.

With respect to the developer used in the pattern forming process, suitable alkaline aqueous solutions include TMAH aqueous solutions as mentioned above and alkaline aqueous solutions described in JP-A 2015-180748, paragraphs [0148]-[0149], preferably 2 to 3 wt % TMAH aqueous solutions. Suitable organic solvent developers include 2-octanone, 2-nonanone, 2-heptanone, 3-heptanone, 4-heptanone, 2-hexanone, 3-hexanone, diisobutyl ketone, methylcyclohexanone, acctophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, which may be used alone or in admixture.

EXAMPLE

Synthesis Examples, Examples and Comparative Examples are given below by way of illustration and not by way of limitation. The abbreviation "pbw" is parts by weight. For all polymers, Mw and Mn are determined by GPC versus polystyrene standards using THF solvent. THF stands for tetrahydrofuran, MEK for methyl ethyl ketone, and MIBK for methyl isobutyl ketone. Analytic instruments are as shown below.

IR: NICOLET 6700 by Thermo Fisher Scientific Inc.
$^1$H-NMR: ECA-500 by JEOL Ltd.
$^{19}$F-NMR: ECA-500 by JEOL Ltd.
MALDI-TOF-MS: S3000 by JBOL Ltd.

1) Synthesis of Sulfonium Salts

Sulfonium salts serving as PAG were synthesized according to the following formulation.

Example 1-1

Synthesis of PAG-1

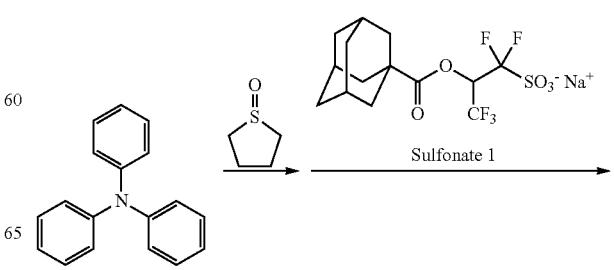

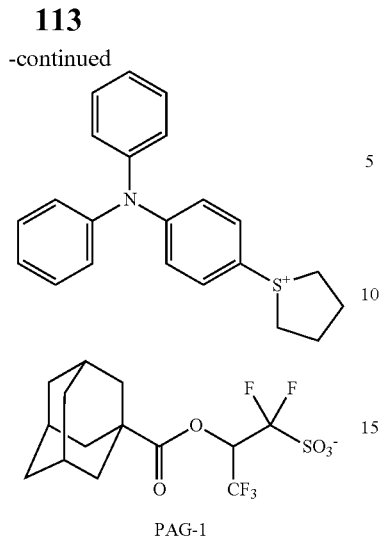

PAG-1

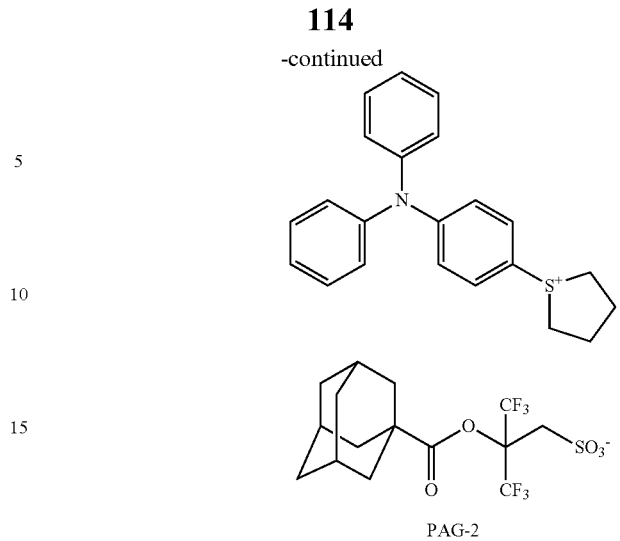

PAG-2

Under ice cooling, 1.04 g of tetramethylene sulfoxide was added dropwise to a mixture of 4.91 g of triphenylamine, 9.81 g of Eaton reagent (Tokyo Chemical Industry Co., Ltd., the same hereinafter) and 10 g of dichloromethane. The contents were stirred under ice cooling for 1 hour and at room temperature for a further 4 hours for aging. The reaction mixture was quenched by adding 40 g of water, combined with 4.14 g of Sulfonate 1 and 30 g of dichloromethane, and stirred, after which the organic layer was taken out. The organic layer was washed 5 times with 30 g of water, from which dichloromethane was removed by vacuum concentration. The procedure including adding 30 g of diisopropyl ether to the concentrate, stirring for 5 minutes, and removing the supernatant was repeated 5 times. This was followed by vacuum concentration. The thus precipitated solid was dried under reduced pressure, obtaining 4.93 g of the desired compound PAG-1 in solid form (yield 67%). Spectral data of PAG-1 are shown below.

IR (D-ATR): ν=3483, 3068, 2908, 2853, 1754, 1580, 1492, 1453, 1423, 1371, 1335, 1264, 1245, 1216, 1182, 1164, 1103, 1087, 1032, 992, 916, 867, 824, 757, 732, 697, 676, 640, 612, 598, 582 cm$^{-1}$ $^1$H-NMR (500 MHz, DMSO-$d_6$): δ=1.58-1.73 (6H, m), 1.74-1.91 (6H, m), 1.96 (3H, s), 2.23 (2H, m), 2.35 (2H, m), 3.59 (2H, m), 3.87 (2H, m), 5.93 (1H, m), 6.91 (2H, m), 7.18 (4H, m), 7.24 (2H, m), 7.42 (4H, m), 7.69 (2H, m) ppm $^{19}$F-NMR (500 MHz, DMSO-$d_6$): δ=−119.5 (1F, m), −113.5 (1F, m), −72.4 (3F, m) ppm TOF-MS (MALDI): POSITIVE M$^+$ 332 (corresponding to $C_{22}H_{22}NS^+$)
NEGATIVE M$^-$ 391 (corresponding to $C_{14}H_{16}F_5O_5S^-$)

Example 1-2

Synthesis of PAG-2

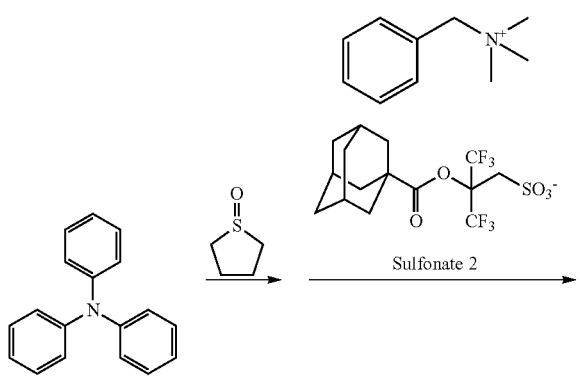

Under ice cooling, 1.04 g of tetramethylene sulfoxide was added dropwise to a mixture of 6.13 g of triphenylamine, 12.27 g of Eaton reagent and 12.5 g of dichloromethane. The contents were stirred under ice cooling for 1 hour and at room temperature for a further 4 hours for aging. The reaction mixture was quenched by adding 60 g of water, combined with 6.88 g of Sulfonate 2 and 40 g of dichloromethane, and stirred, after which the organic layer was taken out. The organic layer was washed 5 times with 40 g of water, from which dichloromethane was removed by vacuum concentration. The concentrate was purified by silica gel chromatography, obtaining 3.50 g of the desired compound PAG-2 in solid form (yield 46%). Spectral data of PAG-2 are shown below.

IR (D-ATR): ν=3456, 3032, 2908, 2852, 1760, 1580, 1492, 1453, 1408, 1330, 1299, 1237, 1219, 1196, 1127, 1060, 1041, 1018, 970, 824, 758, 729, 697, 650, 616, 594 cm$^{-1}$ $^1$H-NMR (500 MHz, DMSO-$d_6$): δ=1.58-1.70 (6H, m), 1.83 (6H, d), 1.95 (3H, s), 2.23 (2H, m), 2.34 (2H, m), 3.55 (2H, s), 3.59 (2H, m), 3.88 (2H, m), 6.91 (2H, m), 7.17 (4H, m), 7.24 (2H, m), 7.42 (4H, m), 7.70 (2H, m) ppm $^{19}$F-NMR (500 MHz, DMSO-$d_6$): δ=−72.3 (6F, s) ppm TOF-MS (MALDI): POSITIVE M$^+$ 332 (corresponding to $C_{22}H_{22}NS^+$)
NEGATIVE M$^-$ 423 (corresponding to $C_{15}H_{17}F_6O_5S^-$)

Example 1-3

Synthesis of PAG-3

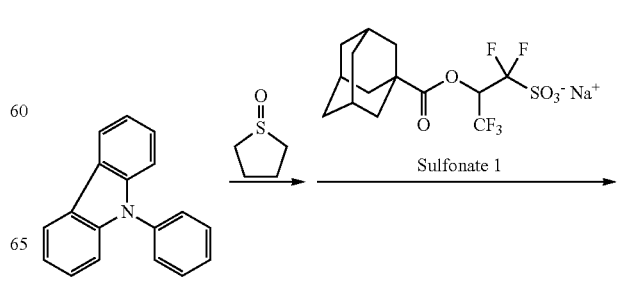

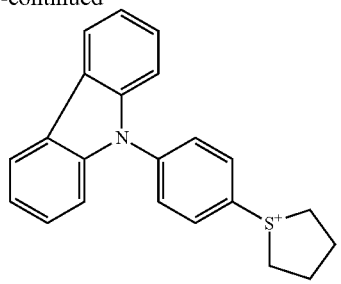

PAG-3

Under ice cooling, 1.04 g of tetramethylene sulfoxide was added dropwise to a mixture of 6.08 g of 9-phenylcarbazole, 12.17 g of Eaton reagent and 12.17 g of dichloromethane. The contents were stirred under ice cooling for 1 hour and at room temperature for a further 16 hours for aging. The reaction mixture was quenched by adding 50 g of water, combined with 30 g of diisopropyl ether, and stirred, after which the water layer was taken out. The water layer was washed 2 times with 30 g of diisopropyl ether, combined with 6.30 g of Sulfonate 1 and 50 g of MIBK, and stirred, after which the organic layer was taken out. The organic layer was washed 5 times with 40 g of water, from which dichloromethane was removed by vacuum concentration. To the concentrate, 50 g of diisopropyl ether was added for crystallization. The resulting solid was dried under reduced pressure, obtaining 6.46 g of the desired compound PAG-3 In solid form (yield 88%). Spectral data of PAG-3 are shown below.

IR (D-ATR): ν=3058, 2966, 2937, 2906, 2848, 1762, 1594, 1504, 1485, 1472, 1452, 1426, 1380, 1366, 1331, 1320, 1259, 1238, 1215, 1187, 1157, 1140, 1104, 1087, 1076, 1030, 993, 919, 864, 837, 803, 773, 755, 731, 699, 643, 616, 591 cm$^{-1}$ $^1$H-NMR (500 MHz, DMSO-d): δ=1.59-1.70 (6H, m), 1.83 (6H, d), 1.95 (3H, s), 2.32 (2H, m), 2.50 (2H, m), 3.79 (2H, s), 4.03 (2H, m), 5.94 (1H, m), 739-7.44 (2H, m), 7.54-7.57 (2H, m), 7.60-7.64 (3H, m), 7.70-7.79 (2H, m), 7.92 (1H, dd), 8.46 (1H, d), 8.91 (1H, d) ppm $^{19}$F-NMR (500 MHz, DMSO-d$_6$): δ=−119.5 (1F, m), −113.5 (1F, m), −72.5 (3F, m) ppm TOF-MS (MALDI): POSITIVE M$^+$ 330 (corresponding to $C_{22}H_{20}NS^+$)

NEGATIVE M$^-$ 391 (corresponding to $C_{14}H_{16}F_5O_5S^-$)

Example 1-4

Synthesis of PAG-4

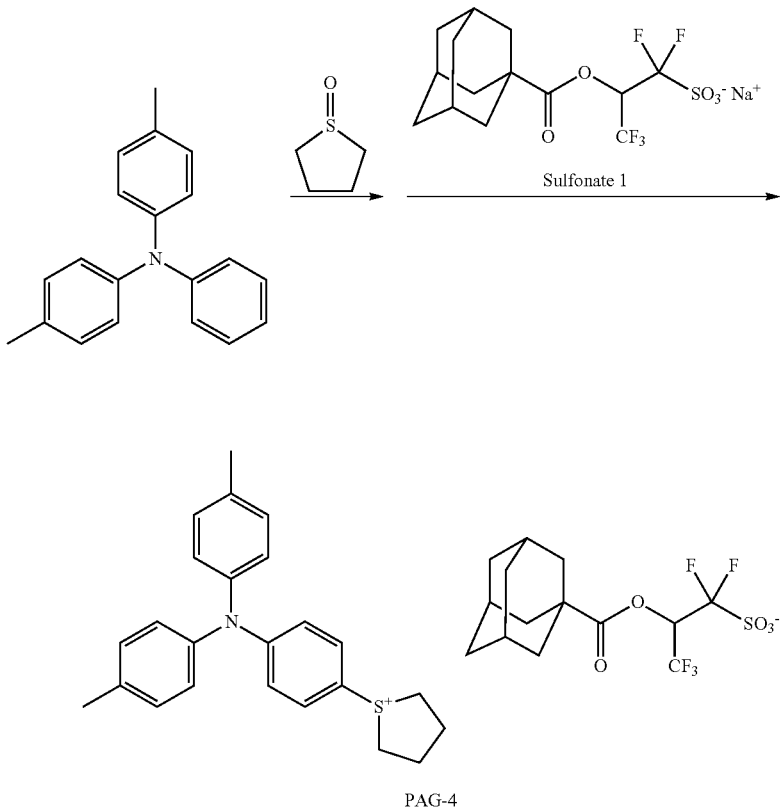

PAG-4

Under ice cooling, 1.04 g of tetramethylene sulfoxide was added dropwise to a mixture of 4.10 g of 4,4'-dimethyltriphenylamine, 8.20 g of Eaton reagent and 8.20 g of dichloromethane. The contents were stirred under ice cooling for 1 hour and at room temperature for a further 16 hours for aging. The reaction mixture was quenched by adding 50 g of water, combined with 30 g of diisopropyl ether, and stirred, after which the water layer was taken out. The water layer was washed 2 times with 30 g of diisopropyl ether, combined with 6.30 g of Sulfonate 1 and 50 g of MIBK, and stirred, after which the organic layer was taken out. The organic layer was washed 7 times with 40 g of water, from which dichloromethane was removed by vacuum concentration. To the concentrate, 50 g of diisopropyl ether was added for crystallization. The resulting solid was dried under reduced pressure, obtaining 5.00 g of the desired compound PAG-4 in solid form (yield 65%). Spectral data of PAG-4 are shown below.

IR (D-ATR): ν=3029, 2909, 2854, 1749, 1581, 1508, 1494, 1453, 1376, 1331, 1303, 1279, 1254, 1217, 1195, 1182, 1163, 1082, 1051, 990, 918, 865, 820, 800, 730, 712, 676, 641, 615, 602, 575, 565 cm$^{-1}$ $^1$H-NMR (500 MHz, DMSO-d$_6$): δ=1.60-1.70 (6H, m), 1.83 (6H, d), 1.96 (3H, s), 2.22 (2H, m), 2.30 (6H, s), 2.34 (2H, m), 3.56 (2H, m), 3.87 (2H, m), 5.93 (1H, m), 6.83 (2H, m), 7.07 (4H, m), 7.22 (4H, d), 7.64 (2H, m) ppm $^{19}$F-NMR (500 MHz, DMSO-d$_6$): δ=−119.5 (1F, m), −113.6 (1F, m), −72.5 (3F, m) ppm TOF-MS (MALDI): POSITIVE M$^+$ 360 (corresponding to C$_{24}$H$_{26}$NS$^+$)

NEGATIVE M$^-$ 391 (corresponding to C$_{14}$H$_{16}$F$_5$O$_5$S$^-$)

Example 1-5

Synthesis of PAG-5

Grignard reagent 1 was prepared in a concentration of 1387 g/mol by adding 1.97 g of magnesium and 5.0 g of THF to a flask, adding dropwise a mixture of 25.0 g of 4-bromotriphenylamine and 75.0 g of THF thereto, and stirring at 80° C. for 20 hours for aging. Subsequently, under ice cooling, 51.48 g of Grignard reagent 1 was added dropwise to a mixture of 2.50 g of diphenyl sulfoxide and 15 g of THF. Stirring was continued for 10 minutes under ice cooling, after which 4.03 g of trimethylsilyl chloride was added dropwise to the mixture, which was stirred at the temperature for 3 hours and at room temperature for a further 12 hours for aging. The reaction mixture was quenched with 9.03 g of 5 wt % hydrochloric acid. Then 8.00 g of Sulfonate 1, 80 g of methylene chloride and 30 g of water were added to the reaction mixture, from which the organic layer was taken out. The organic layer was washed 5 times with 30 g of water, from which the solvent was removed by vacuum concentration. The concentrate was purified by silica gel chromatography, obtaining 4.45 g of the desired compound PAG-5 in solid form (yield 42%). Spectral data of PAG-5 are shown below.

IR (D-ATR): ν=3062, 2907, 2853, 1754, 1576, 1491, 1447, 1339, 1302, 1250, 1216, 1182, 1163, 1103, 1085, 1073, 1032, 993, 916, 866, 825, 756, 735, 701, 685, 659, 640, 615, 589, 571 cm$^{-1}$ $^1$H-NMR (500 MHz, DMSO-d$_6$): δ=1.60-1.68 (6H, m), 1.83 (6H, d), 1.95 (3H, s), 5.93 (1H, m), 6.93 (2H, m), 7.25-7.29 (6H, m), 7.44 (4H, m), 7.66 (2H, m), 7.74-7.78 (8H, m), 7.82 (2H, m) ppm $^{19}$F-NMR (500 MHz, DMSO-d$_6$): δ=−119.5 (1F, m), −113.6 (1F, m), −72.4 (3F, m) ppm TOF-MS (MALDI): POSITIVE M$^+$ 430 (corresponding to C$_{30}$H$_{24}$NS$^+$)

NEGATIVE M$^-$ 391 (corresponding to C$_{14}$H$_{16}$F$_5$O$_5$S$^-$)

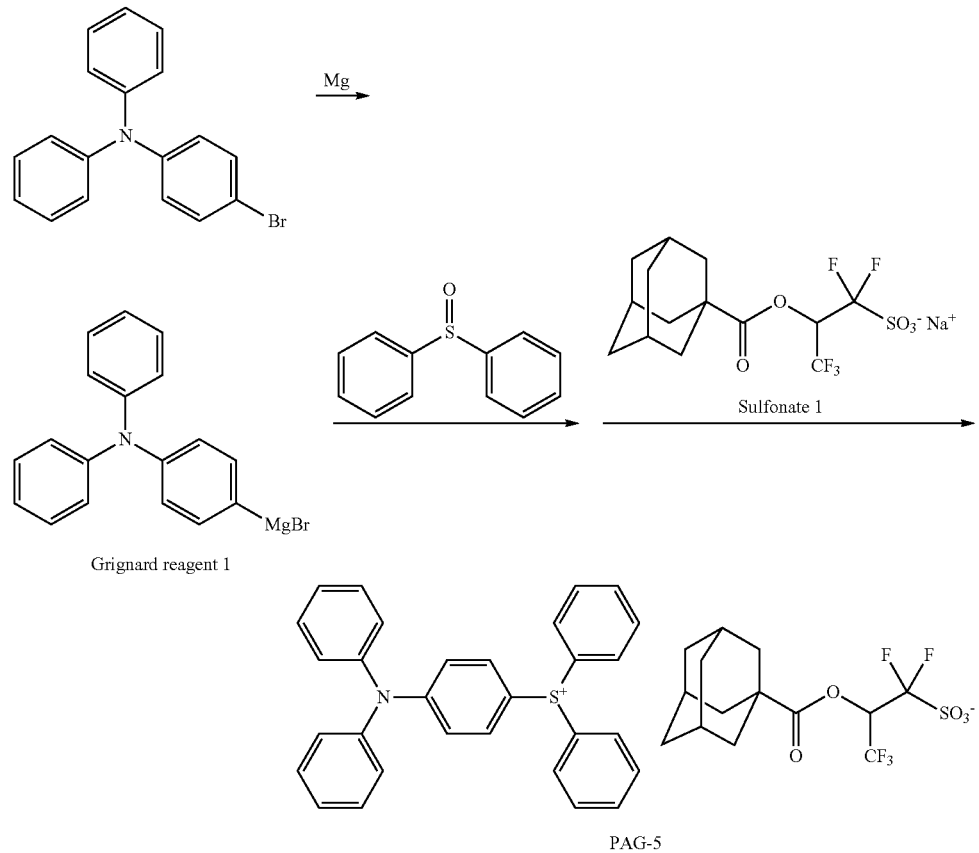

PAG-5

Example 1-6

Synthesis of PAG-6

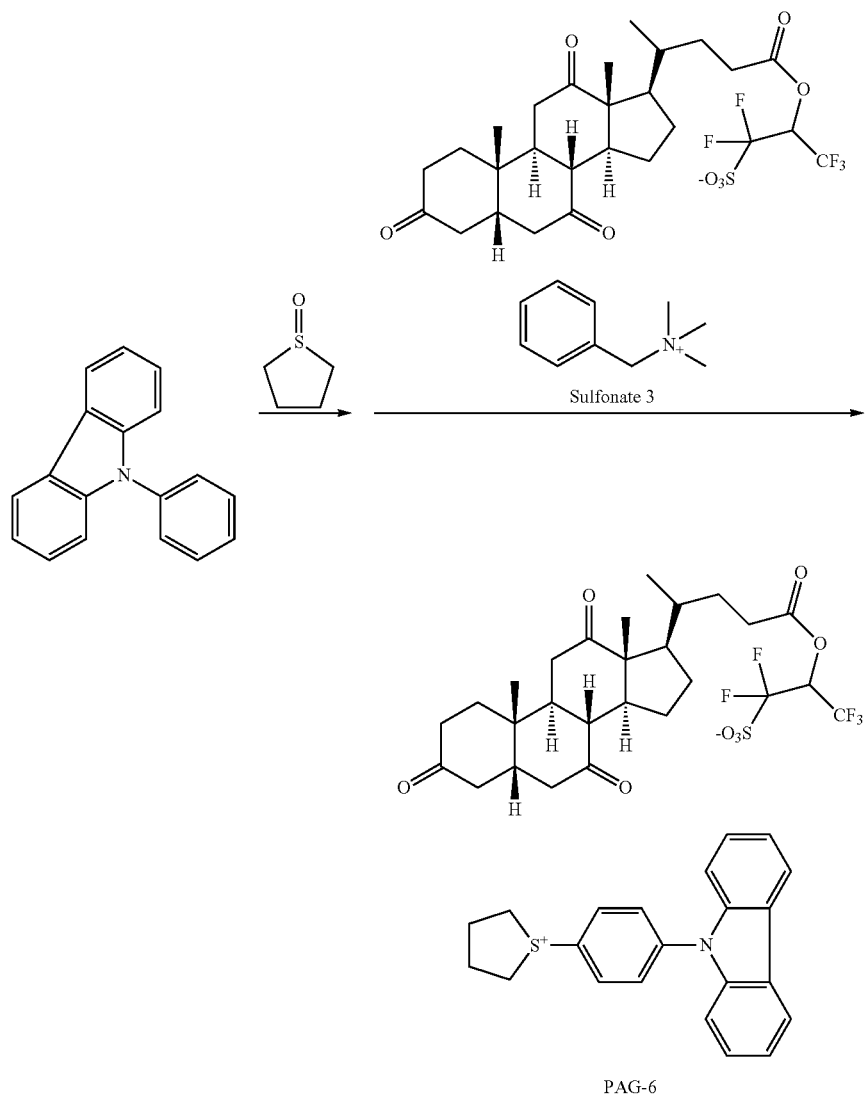

PAG-6

Under ice cooling, 3.25 g of tetramethylene sulfoxide was added dropwise to a mixture of 19.0 g of 9-phenylcarbazole, 38 g of Eaton reagent and 38 g of dichloromethane. The contents were stirred under ice cooling for 1 hour and at room temperature for a further 16 hours for aging. The reaction mixture was quenched by adding 160 g of water, combined with 120 g of diisopropyl ether, and stirred, after which the water layer was taken out. The water layer was washed 2 times with 120 g of diisopropyl ether, combined with 24.79 g of Sulfonate 3 and 100 g of MIBK, and stirred for 15 minutes, after which the organic layer was taken out. The organic layer was washed 3 times with 50 g of water, from which the solvent was removed by vacuum concentration. The concentrate was purified by silica gel chromatography, obtaining 23.10 g of the desired compound PAG-6 in solid form (yield 74%). Spectral data of PAG-6 are shown below.

$^1$H-NMR (500 MHz, DMSO-d$_6$): δ=0.75 (3H, m), 0.98 (3H, s), 1.19-1.30 (4H, m), 1.31 (3H, s), 1.47 (1H, m), 1.64-1.99 (9H, m), 2.06-2.54 (11H, m), 2.82 (1H, t), 2.97 (1H, dd), 3.04 (1H, m), 3.79 (2H, m), 4.02 (2H, m), 5.94 (1H, m), 7.39-7.45 (2H, m), 7.53-7.65 (5H, m), 7.73 (2H, m), 7.92 (1H, dd), 8.46 (1H, d), 8.91 (1H, d) ppm $^{19}$F-NMR (500 MHz, DMSO-d$_6$): δ=−119.8 (1F, m), −113.8 (1F, n), −72.3 (3F, m) ppm TOF-MS (MALDI): POSITIVE M$^+$ 330 (corresponding to C$_{22}$H$_{20}$NS$^+$)

NEGATIVE M$^-$ 613 (corresponding to C$_{27}$H$_{34}$F$_5$O$_8$S$^-$)

Example 1-7

Synthesis of PAG-7

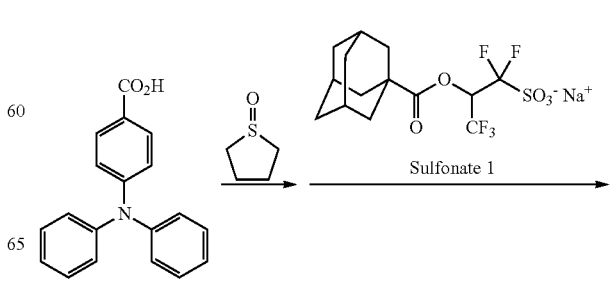

-continued

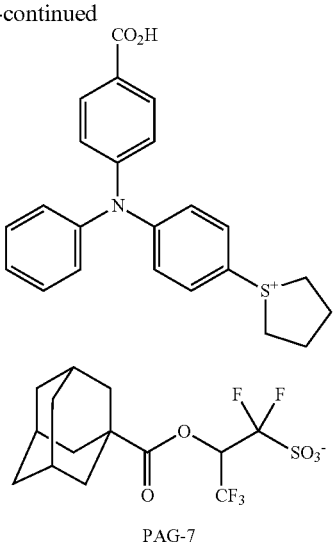
PAG-7

Under ice cooling, 2.08 g of tetramethylene sulfoxide was added dropwise to a mixture of 8.68 g of 4-(diphenylamino) benzoic acid, 1736 g of Eaton reagent and 17.36 g of dichloromethane. The contents were stirred under ice cooling for 1 hour and at room temperature for a further 16 hours for aging. The reaction mixture was quenched by adding 80 g of water, combined with 80 g of diisopropyl ether, and stirred, after which the water layer was taken out. The water layer was washed 2 times with 80 g of diisopropyl ether, combined with 10.0 g of Sulfonate 1 and 100 g of methylene chloride, and stirred, after which the organic layer was taken out. The organic layer was washed 7 times with 40 g of water, from which the solvent was removed by vacuum concentration. To the concentrate, 70 g of diisopropyl ether was added for crystallization. The resulting solid was dried under reduced pressure, obtaining 13.78 g of the desired compound PAG-7 in solid form (yield 87%). Spectral data of PAG-7 are shown below.

IR (D-ATR): ν=3057, 2907, 2853, 1754, 1710, 1608, 1581, 1492, 1453, 1424, 1374, 1326, 1270, 1246, 1215, 1182, 1166, 1103, 1087, 1051, 1032, 991, 916, 837, 787, 763, 729, 699, 641, 612 cm$^{-1}$ $^{1}$H-NMR (500 MHz, DMSO-d$_6$): δ=1.60-1.70 (6H, m), 1.83 (6H, d), 1.96 (3H, s), 2.25 (2H, m), 2.34 (2H, m), 3.65 (2H, m), 3.89 (2H, m), 5.93 (1H, m), 7.08-7.14 (4H, m), 7.17 (2H, m), 7.29 (1H, m), 7.45 (2H, m), 7.79 (2H, m), 7.90 (2H, m), 12.82 (1H, br) ppm $^{19}$F-NMR (500 MHz, DMSO-d$_6$): δ=−119.6 (1F, m), −113.6 (1F, m), −72.5 (3F, m) ppm TOF-MS (MALDI): POSITIVE M$^+$ 376 (corresponding to $C_{23}H_{22}NO_2S^+$)

NEGATIVE M$^-$ 391 (corresponding to $C_{14}H_{16}F_5O_5S^-$)

Example 1-8

Synthesis of PAG-8

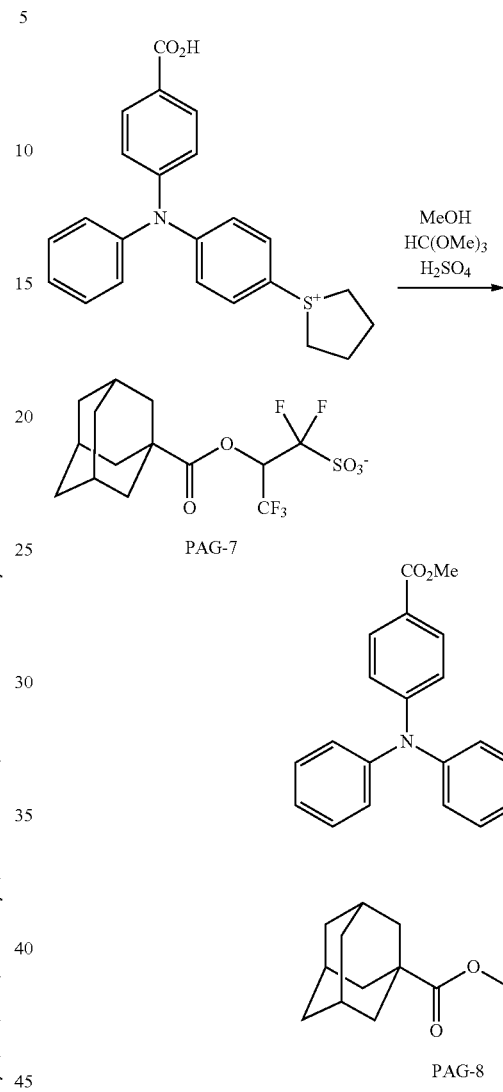

A catalytic amount (0.05 g) of sulfuric acid was added dropwise to a mixture of 4.0 g of PAG-7, 0.83 g of trimethyl o-formate, and 20 g of methanol. The mixture was stirred at room temperature for 15 hours and at 40° C. for a further 7 hours. The reaction mixture was quenched by adding 5 g of saturated sodium hydrogencarbonate aqueous solution, combined with 40 g of MIBK and 40 g of water, and stirred, after which the organic layer was taken out. The organic layer was washed 3 times with 20 g of water, once with 20 g of 1 wt % hydrochloric acid, and 3 times with 20 g of water. The solvent was removed from the resulting organic layer by vacuum concentration. The concentrate was purified by silica gel chromatography, obtaining 1.10 g of the desired compound PAG-8 (yield 25%). Spectral data of PAG-8 are shown below.

$^{1}$H-NMR (500 MHz, DMSO-d$_6$): δ=1.60-1.70 (6H, m), 1.83 (6H, d), 1.96 (3H, s), 2.24 (2H, m), 2.34 (2H, m), 3.65 (2H, m), 3.82 (3H, s), 3.89 (2H, m), 5.93 (1H, m), 7.08-7.19 (6H, m), 7.30 (1H, m), 7.46 (2H, m), 7.80 (2H, m), 7.91 (2H, m) ppm $^{19}$F-NMR (500 MHz, DMSO-d$_6$): δ=−119.6 (1F, m), −113.6 (1F, m), −72.5 (3F, m) ppm Examples 1-9 to 1-14: Synthesis of PAG-9 to PAG-14

PAG-9 to PAG-14, shown below, were synthesized as in Example 1-1 using the corresponding reactants.

PAG-9
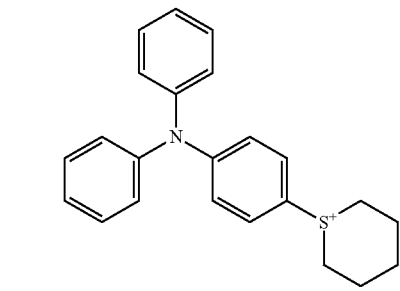

PAG-10
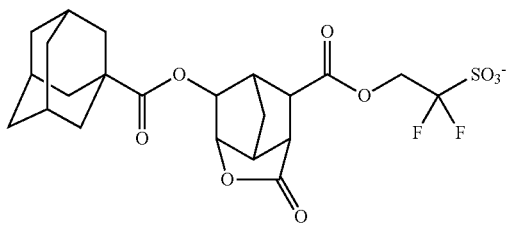

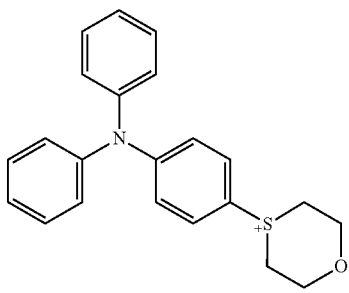

PAG-11
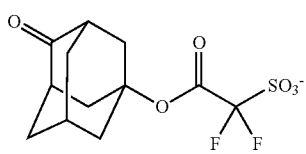

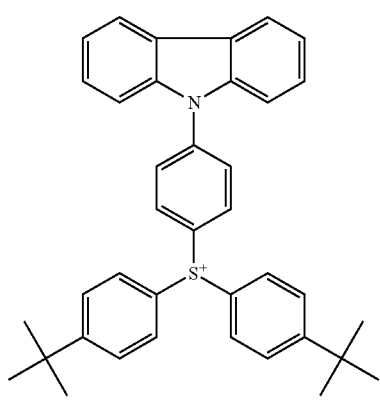

-continued

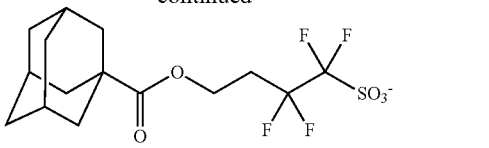
PAG-12

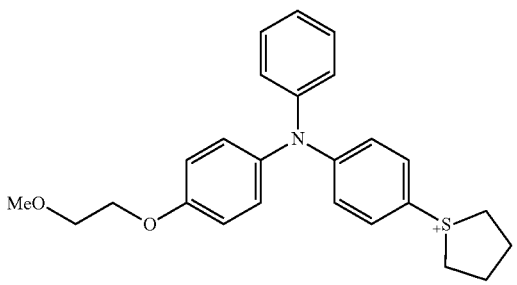
PAG-13

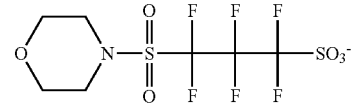

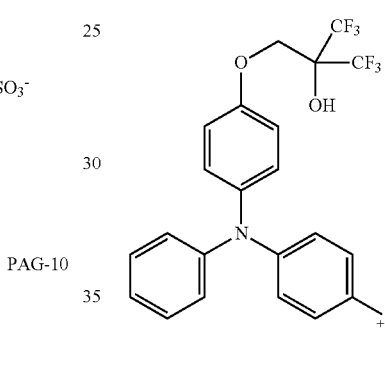

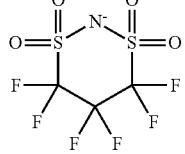
PAG-14

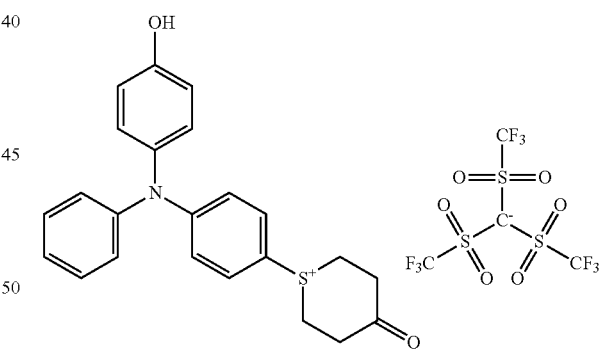

2) Synthesis of Polymers

Polymers for use in resist compositions were synthesized according to the following formulation.

Synthesis Example 1-1

Synthesis of Polymer P-1

In a flask under nitrogen atmosphere, 22 g of 1-t-butyl-cyclopentyl methacrylate, 17 g of 2-oxotetrahydrofuran-3-yl methacrylate, 0.48 g of dimethyl 2,2'-azobis(2-methyl-propionate) (V-601 by Wako Pure Chemical Industries, Ltd.), 0.41 g of 2-mercaptoethanol, and 50 g of MEK were combined to form a monomer/initiator solution. Another flask in nitrogen atmosphere was charged with 23 g of MEK, which was heated at 80° C. with stirring. With stirring, the monomer/initiator solution was added dropwise to the flask over 4 hours. After the completion of dropwise addition, the polymerization solution was continuously stirred for 2 hours while maintaining the temperature of 80° C. The polymerization solution was cooled to room temperature, whereupon it was added dropwise to 640 g of methanol with vigorous stirring. The precipitate was collected by filtration, washed twice with 240 g of methanol, and vacuum dried at 50° C. for 20 hours, obtaining 36 g of a copolymer (Polymer P-1) in white powder form (yield 90%). On GPC analysis, Polymer P-1 had a Mw of 8,100 and a dispersity Mw/Mn of 1.64.

Polymer P-1

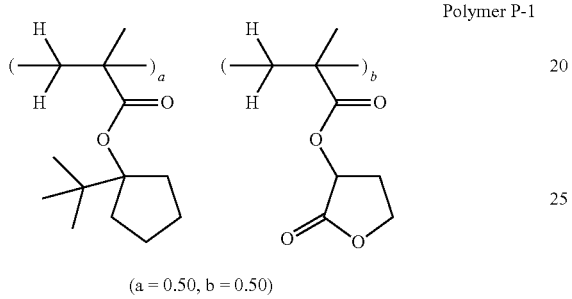

(a = 0.50, b = 0.50)

Synthesis Examples 1-2 to 1-6

Synthesis of Polymers P-2 to P-6

Polymers P-2 to P-6 were synthesized by the same procedure as in Synthesis Example 1-1 aside from changing the type and amount of monomers. Table 1 shows the proportion (in molar ratio) of units incorporated in these polymers. The structure of recurring units is shown in Tables 2 and 3.

TABLE 1

| Resin | Unit 1 (molar ratio) | Unit 2 (molar ratio) | Unit 3 (molar ratio) | Unit 4 (molar ratio) | Mw | Mw/Mn |
|---|---|---|---|---|---|---|
| P-1 | A-1 (0.50) | B-1 (0.50) | — | — | 8,100 | 1.64 |
| P-2 | A-1 (0.40) | B-2 (0.50) | B-4 (0.10) | — | 7,800 | 1.70 |
| P-3 | A-1 (0.40) | B-1 (0.35) | B-3 (0.15) | B-4 (0.10) | 8,500 | 1.75 |
| P-4 | A-2 (0.15) | A-3 (0.35) | B-1 (0.40) | B-4 (0.10) | 8,300 | 1.69 |
| P-5 | A-2 (0.15) | A-3 (0.35) | B-2 (0.40) | B-4 (0.10) | 9,100 | 1.80 |
| P-6 | A-1 (0.20) | A-4 (0.15) | B-1 (0.55) | B-4 (0.10) | 10,200 | 1.88 |

TABLE 2

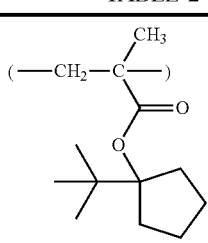 A-1

TABLE 2-continued

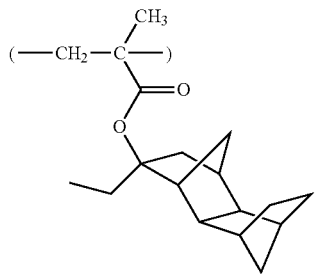 A-2

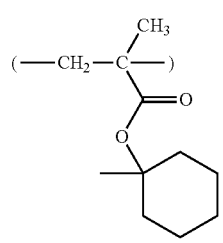 A-3

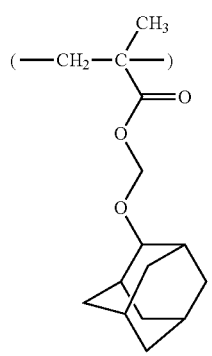 A-4

TABLE 3

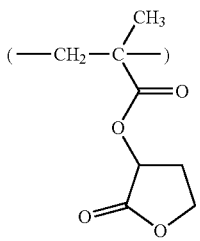 B-1

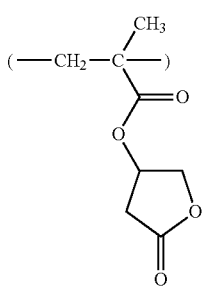 B-2

TABLE 3-continued

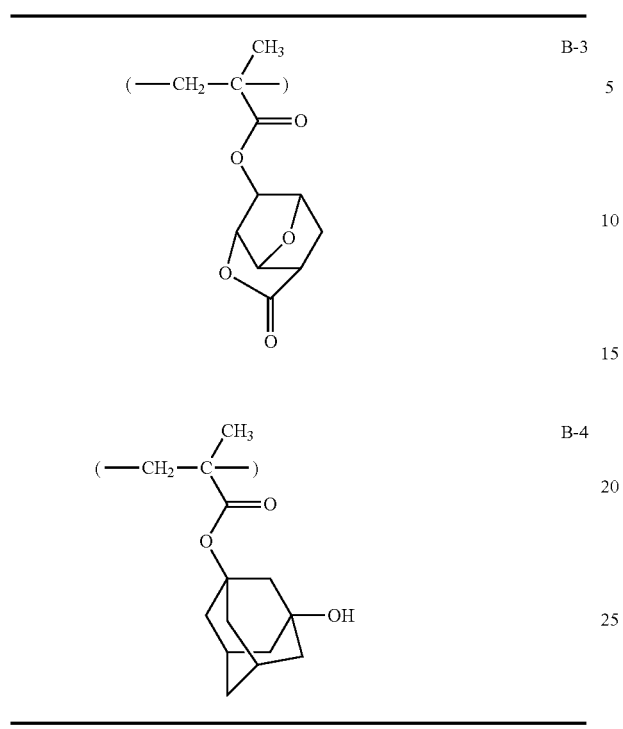

3) Preparation of Resist Composition

Examples 2-1 to 2-14 and Comparative Examples 1-1 to 1-9

Resist compositions in solution form were prepared by dissolving a photoacid generator (PAG-1 to PAG-14), polymer (Polymer P-1 to P-6), alkali-soluble surfactant (SF-1), optionally quencher (Q-1) and second photoacid generator (PAG-A to PAG-J) in an organic solvent containing 0.01 wt % of surfactant A in accordance with the formulation shown in Tables 4 and 5, and filtering through a Teflon® filter with a pore size of 0.2 μm.

The quencher, solvent, second PAG, alkali-soluble surfactant (SF-1) and surfactant A used herein are identified below.

Quencher (Q-1): 1-(tert-butoxycarbonyl)-4-hydroxypiperidine

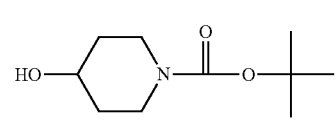

Solvent: PGMEA=propylene glycol monomethyl ether acetate

GBL=γ-butyrolactone

Second PAG:

PAG-A: triphenylsulfonium 2-(adamantane-1-carbonyloxy)-1,1,3,3,3-pentafluoropropane-1-sulfonate (described in JP-A 2007-145797

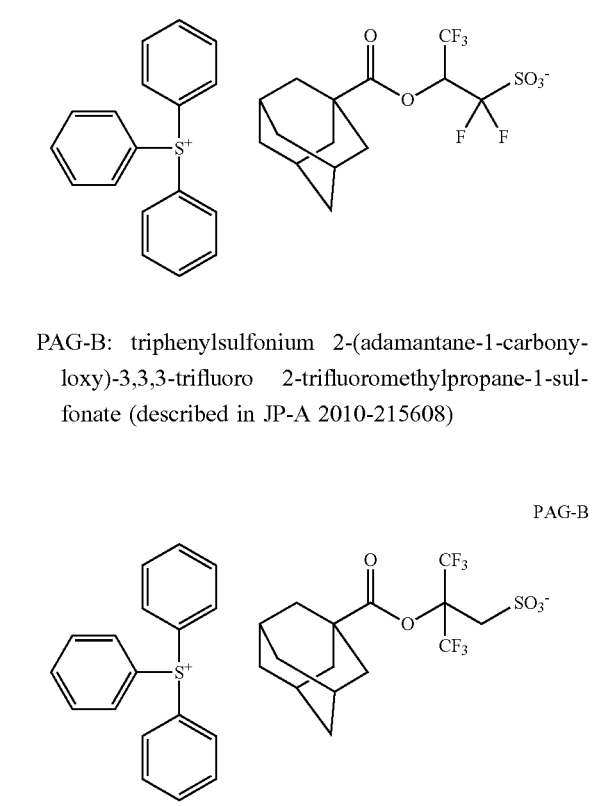

PAG-B: triphenylsulfonium 2-(adamantane-1-carbonyloxy)-3,3,3-trifluoro 2-trifluoromethylpropane-1-sulfonate (described in JP-A 2010-215608)

PAG-C: 1-(9-ethyl-9H-carbazol-3-yl)tetrahydrothiophenium 2-(adamantane-1-carbonyloxy)-1,1,3,3,3-pentafluoropropanesulfonate (see the cation described in JP-A 2013-020089)

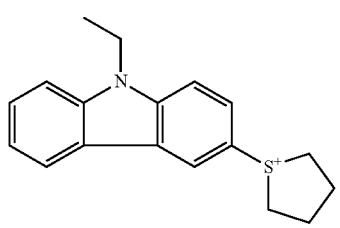

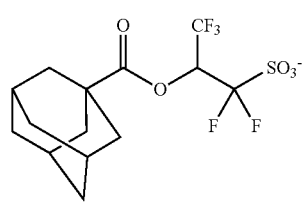

PAC-D: 4-(2-methoxyethoxy)naphthalene-1-tetrahydrothiophenium 2-(adamantane-1-carbonyloxy)-1,1,3,3-pentafluoropropanesulfonate (described in JP-A 2012-041320)

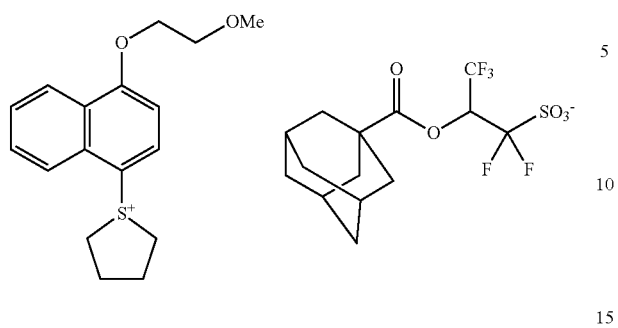
PAG-D

PAG-E: 4-(4-tert-butylphenyl)-1,4-oxathian-4-ium difluoro-(4-oxoadamantan-1-yloxycarbonyl)-methanesulfonate (described in JP-A 2012-224611)

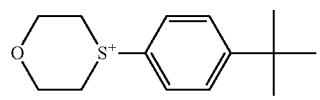
PAG-E

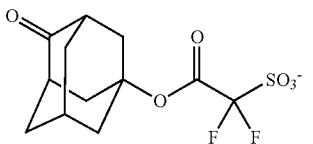

PAG-F: 4-[2-(4-cyclohexylphenyl)-1,1-dimethyl-2-oxoethyl]-1,4-oxathian-4-ium 2-(adamantane-1-carbonyloxy)-1,1,3,3,3-pentafluoropropanesulfonate (see JP-A 2014-006491)

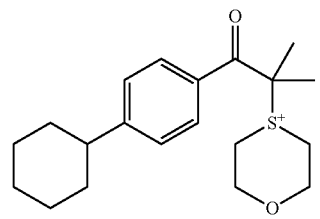
PAG-F

PAG-G: bis(tert-butylphenyl)phenylsulfonium 2-(adamantane-1-carbonyloxy)-1,1,3,3,3-pentafluoropropane-1-sulfonate

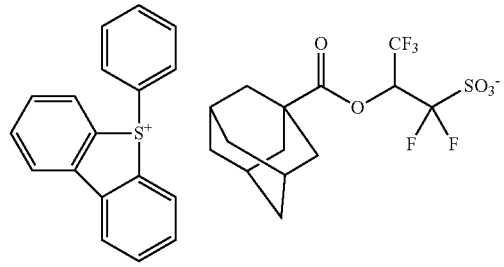
PAG-G

PAG-H: 5-phenyl-dibenzothiophenium 2 (adamantane-1-carbonyloxy)-1,1,3,3,3-pentafluoropropane-1-sulfonate

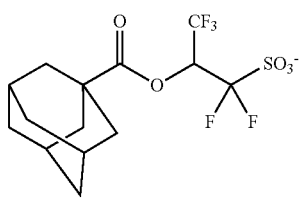
PAG-H

PAG-I: see WO 2015/046502

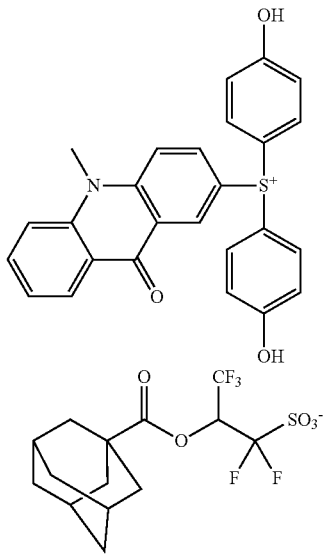
PAG-I

PAG-J:

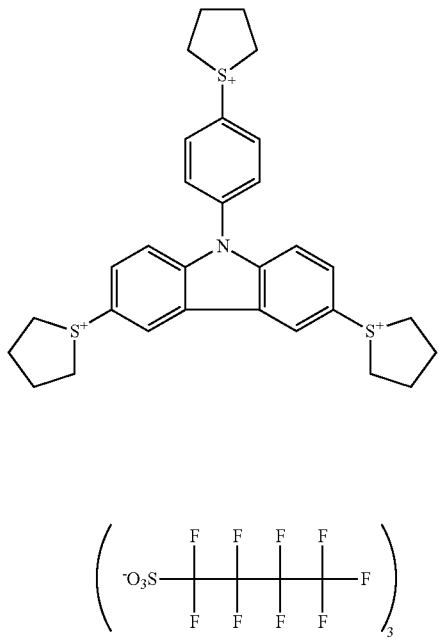

Alkali-soluble surfactant (SF-1): poly(2,2,3,3,4,4,4-hepta-fluoro-1-isobutyl-1-butyl methacrylate/9-(2,2,2-trifluoro-1-trifluoroethyloxycarbonyl)-4-oxatricyclo[4.2.1.0$^{3,7}$]nonan-5-on-2-yl methacrylate
Mw=7,700
Mw/Mn=1.82

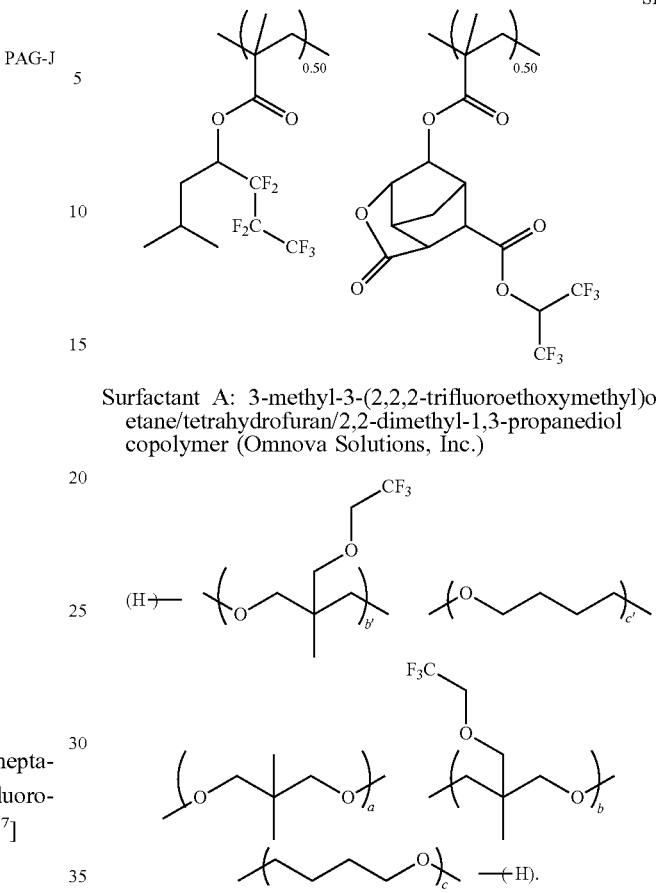

Surfactant A: 3-methyl-3-(2,2,2-trifluoroethoxymethyl)oxetane/tetrahydrofuran/2,2-dimethyl-1,3-propanediol copolymer (Omnova Solutions, Inc.)

a:(b+b'):(c+c')=1:4-7:0.01-1 (molar ratio)
Mw=1,500

TABLE 4

|  |  | Resist composition | Polymer (pbw) | PAG (pbw) | Quencher (pbw) | Surfactant (pbw) | Solvent 1 (pbw) | Solvent 2 (pbw) |
|---|---|---|---|---|---|---|---|---|
| Example | 2-1 | R-1 | P-1 (80) | PAG-1 (8.0) PAG-B (3.0) | Q-1 (1.0) | SF-1 (3.0) | PGMEA (1,536) | GBL (384) |
|  | 2-2 | R-2 | P-1 (80) | PAG-A (8.0) PAG-2 (3.0) | Q-1 (1.0) | SF-1 (3.0) | PGMEA (1,536) | GBL (384) |
|  | 2-3 | R-3 | P-2 (80) | PAG-3 (9.0) PAG-B (3.0) | — | SF-1 (3.0) | PGMEA (1,536) | GBL (384) |
|  | 2-4 | R-4 | P-1 (80) | PAG-4 (9.0) PAG-B (3.0) | Q-1 (1.0) | SF-1 (3.0) | PGMEA (1,536) | GBL (384) |
|  | 2-5 | R-5 | P-3 (80) | PAG-5 (5.0) PAG-D (4.0) | — | SF-1 (3.0) | PGMEA (1,536) | GBL (384) |
|  | 2-6 | R-6 | P-4 (80) | PAG-6 (9.0) PAG-B (3.0) | — | SF-1 (3.0) | PGMEA (1,536) | GBL (384) |
|  | 2-7 | R-7 | P-4 (80) | PAG-7 (8.0) PAG-B (2.0) | — | SF-1 (3.0) | PGMEA (1,536) | GBL (384) |
|  | 2-8 | R-8 | P-5 (80) | PAG-8 (8.0) PAG-2 (4.0) | — | SF-1 (3.0) | PGMEA (1,536) | GBL (384) |
|  | 2-9 | R-9 | P-1 (80) | PAG-9 (9.0) PAG-B (3.5) | — | SF-1 (3.0) | PGMEA (1,536) | GBL (384) |
|  | 2-10 | R-10 | P-1 (80) | PAG-10 (8.5) PAG-B (3.0) | — | SF-1 (3.0) | PGMEA (1,536) | GBL (384) |
|  | 2-11 | R-11 | P-3 (80) | PAG-11 (5.0) PAG-D (4.0) | — | SF-1 (3.0) | PGMEA (1,536) | GBL (384) |
|  | 2-12 | R-12 | P-4 (80) | PAG-12 (7.0) PAG-A (3.0) | Q-1 (1.0) | SF-1 (3.0) | PGMEA (1,536) | GBL (384) |
|  | 2-13 | R-13 | P-1 (80) | PAG-13 (7.0) PAG-B (2.0) | Q-1 (1.5) | SF-1 (3.0) | PGMEA (1,536) | GBL (384) |
|  | 2-14 | R-14 | P-6 (80) | PAG-14 (8.0) | Q-1 (1.5) | SF-1 (3.0) | PGMEA (1,536) | GBL (384) |

TABLE 5

| | | Resist composition | Polymer (pbw) | PAG (pbw) | Quencher (pbw) | Surfactant (pbw) | Solvent 1 (pbw) | Solvent 2 (pbw) |
|---|---|---|---|---|---|---|---|---|
| Comparative Example | 1-1 | R-15 | P-1 (80) | PAG-A (8.0) PAG-B (3.0) | Q-1 (1.0) | SF-1 (3.0) | PGMEA (1,536) | GBL (384) |
| | 1-2 | R-16 | P-1 (80) | PAG-C (8.0) PAG-B (3.0) | Q-1 (1.0) | SF-1 (3.0) | PGMEA (1,536) | GBL (384) |
| | 1-3 | R-17 | P-1 (80) | PAG-D (8.0) PAB-B (3.0) | Q-1 (1.0) | SF-1 (3.0) | PGMEA (1,536) | GBL (384) |
| | 1-4 | R-18 | P-1 (80) | PAG-E (8.5) PAG-B (3.0) | — | SF-1 (3.0) | PGMEA (1,536) | GBL (384) |
| | 1-5 | R-19 | P-1 (80) | PAG-F (8.0) PAB-B (3.0) | Q-1 (1.0) | SF-1 (3.0) | PGMEA (1,536) | GBL (384) |
| | 1-6 | R-20 | P-1 (80) | PAG-G (9.0) PAG-B (3.0) | Q-1 (1.0) | SF-1 (3.0) | PGMEA (1,536) | GBL (384) |
| | 1-7 | R-21 | P-2 (80) | PAG-H (9.0) PAG-B (3.0) | — | SF-1 (3.0) | PGMEA (1,536) | GBL (384) |
| | 1-8 | R-22 | P-3 (80) | PAG-I (5.0) PAG-D (4.0) | — | SF-1 (3.0) | PGMEA (1,536) | GBL (384) |
| | 1-9 | R-23 | P-1 (80) | PAG-J (4.0) PAG-B (3.0) | Q-1 (1.0) | SF-1 (3.0) | PGMEA (1,536) | GBL (384) |

4) ArF Lithography Test #1: Evaluation of Hole Pattern

Examples 3-1 to 3-14 and Comparative Examples 2-1 to 2-9

On a substrate, a spin-on carbon film ODL-50 (Shin-Etsu Chemical Co., Ltd.) having a carbon content of 80 wt % was deposited to a thickness of 200 nm and a silicon-containing spin-on hard mask SHB-A940 (Shin-Etsu Chemical Co., Ltd.) having a silicon content of 43 wt % was deposited thereon to a thickness of 35 nm. On this substrate for trilayer process, each of the resist compositions (R-1 to R-14) and comparative resist compositions (R-15 to R-23) was spin coated, then baked on a hotplate at 100° C. for 60 seconds to form a resist film of 100 nm thick.

Using an ArF excimer laser immersion lithography stepper (NSR-610C by Nikon Corp., NA 1.30, a 0.98/0.78, dipole opening 20 deg., azimuthally polarized illumination, dipole illumination, 6% halftone phase shift mask), the resist film was exposed through a first mask having X-axis direction lines with a pitch of 80 nm and a width of 40 nm (on-wafer size) and then through a second mask having Y-axis direction lines with a pitch of 80 nm and a width of 40 nm (on-wafer size). Water was used as the immersion liquid. After exposure, the resist film was baked (PEB) at the temperature shown in Tables 6 and 7 for 60 seconds and developed. Specifically, butyl acetate was injected from a development nozzle for 3 seconds while the wafer was spun at 30 rpm, which was followed by stationary puddle development for 27 seconds.

Evaluation of Sensitivity

The hole pattern thus formed was observed under an electron microscope. The optimum dose (Eop) is a dose (mJ/cm$^2$) which provides a hole pattern having a diameter of 40 nm at a pitch of 80 nm.

Evaluation of Mask Error Factor (MEF)

A pattern was formed by exposure in the optimum dose (determined in the sensitivity evaluation) through a mask with the pitch fixed and the line width varied. MEF was calculated from variations of the mask line width and the pattern space width according to the following equation:

MEF=(pattern space width)/(mask line width)−b wherein b is a constant. A value closer to unity (1) indicates better performance.

Evaluation of Critical Dimension Uniformity (CDU)

The hole pattern printed as above was observed under TD-SEM (CG-4000 by Hitachi Hitechnologies, Ltd.), and 125 holes were measured for diameter. A three-fold value (3σ) of a standard variation (σ) was computed therefrom as a variation of hole size and reported as CDU. A smaller value (3σ) indicates a smaller variation of hole size.

The results are shown in Tables 6 and 7.

TABLE 6

| | | Resist composition | PEB temp. (° C.) | Eop (mJ/cm$^2$) | MEF | CDU (nm) |
|---|---|---|---|---|---|---|
| Example | 3-1 | R-1 | 90 | 35 | 3.3 | 3.5 |
| | 3-2 | R-2 | 85 | 31 | 3.5 | 3.6 |
| | 3-3 | R-3 | 95 | 36 | 3.4 | 3.4 |
| | 3-4 | R-4 | 95 | 35 | 3.7 | 3.7 |
| | 3-5 | R-5 | 95 | 37 | 3.2 | 3.6 |
| | 3-6 | R-6 | 95 | 39 | 3.3 | 3.8 |
| | 3-7 | R-7 | 90 | 37 | 3.5 | 3.5 |
| | 3-8 | R-8 | 95 | 34 | 3.4 | 3.3 |
| | 3-9 | R-9 | 100 | 33 | 3.4 | 3.7 |
| | 3-10 | R-10 | 95 | 34 | 3.7 | 3.8 |
| | 3-11 | R-11 | 105 | 38 | 3.5 | 3.6 |
| | 3-12 | R-12 | 90 | 39 | 3.3 | 3.5 |
| | 3-13 | R-13 | 90 | 30 | 3.6 | 3.5 |
| | 3-14 | R-14 | 100 | 36 | 3.5 | 3.8 |

TABLE 7

| | | Resist composition | PEB temp. (° C.) | Eop (mJ/cm$^2$) | MEF | CDU (nm) |
|---|---|---|---|---|---|---|
| Comparative Example | 2-1 | R-15 | 85 | 38 | 4.2 | 4.5 |
| | 2-2 | R-16 | 90 | 45 | 4.6 | 4.3 |
| | 2-3 | R-17 | 95 | 39 | 4.5 | 4.8 |
| | 2-4 | R-18 | 90 | 38 | 4.3 | 4.6 |
| | 2-5 | R-19 | 95 | 40 | 4.4 | 4.7 |
| | 2-6 | R-20 | 95 | 42 | 4.4 | 4.3 |
| | 2-7 | R-21 | 100 | 40 | 4.2 | 4.5 |
| | 2-8 | R-22 | 105 | 46 | 4.6 | 4.9 |
| | 2-9 | R-23 | 95 | 41 | 4.9 | 5.0 |

It is evident from Tables 6 and 7 that when a hole pattern is formed from the inventive resist composition via organic solvent development, MEF and CDU are improved while maintaining the sensitivity.

5) ArF Lithography Patterning Test #2: Evaluation of L/S Pattern

Examples 4-1 to 4-14 and Comparative Examples 3-1 to 3-9

On a substrate, a spin-on carbon film ODL-50 (Shin-Etsu Chemical Co., Ltd.) having a carbon content of 80 wt % was deposited to a thickness of 200 nm and a silicon-containing spin-on hard mask SHB-A940 (Shin-Etsu Chemical Co., Ltd.) having a silicon content of 43 wt % was deposited thereon to a thickness of 35 nm. On this substrate for trilayer process, each of the resist compositions (Inventive R-1 to R-14 or Comparative R-15 to R-23) was spin coated and baked on a hotplate at 100° C. for 60 seconds to form a resist film of 100 nm thick.

Using an ArF excimer laser immersion lithography scanner NSR-610C (Nikon Corp., NA 1.30, σ0.98/0.78, 4/5 annular illumination), pattern exposure was performed through a 6% halftone phase shift mask bearing a line pattern with a pitch of 100 nm and a line width of 50 nm (on-wafer size). Water was used as the immersion liquid. After exposure, the wafer was baked (PEB) at the temperature shown in Tables 8 and 9 for 60 seconds and developed. Specifically, butyl acetate was injected from a development nozzle for 3 seconds while the wafer was spun at 30 rpm, which was followed by stationary puddle development for 27 seconds. As a result, the unexposed regions of the resist film that were shielded by the mask were dissolved in the developer, that is, image reversal took place, to form a line-and-space (L/S) pattern with a space width of 50 nm and a pitch of 100 nm.

Evaluation of Sensitivity

The L/S pattern was observed under an electron microscope. As an index of sensitivity, the optimum dose (Eop, mJ/cm$^2$) which provided a L/S pattern with a space width of 50 nm and a pitch of 100 nm was determined.

Evaluation of Exposure Latitude (EL)

The exposure dose which provided an L/S pattern with a space width of 50 nm±10% (i.e., 45 nm to 55 nm) was determined. EL (%) is calculated from the exposure doses according to the following equation:

EL (%)=(|E1−E2|/Eop)×100 wherein E1 is an exposure dose which provides an L/S pattern with a space width of 45 nm and a pitch of 100 nm, E2 is an exposure dose which provides an L/S pattern with a space width of 55 nm and a pitch of 100 nm, and Eop is the optimum exposure dose which provides an L/S pattern with a space width of 50 nm and a pitch of 100 nm.

Evaluation of MEF

An L/S pattern was formed by exposure in the optimum dose (determined in the sensitivity evaluation) through the mask with the pitch fixed and the line width varied. MEF was calculated from variations of the mask line width and the pattern space width according to the following equation:

MEF=(pattern space width)/(mask line width)−b wherein b is a constant. A value closer to unity (1) indicates better performance.

Evaluation of Line Width Roughness (LWR)

The L/S pattern formed by exposure in the optimum dose (determined in the sensitivity evaluation) was observed under TDSEM S-9380 (Hitachi Hitechnologies, Ltd.). The space width was measured at longitudinally spaced apart 10 points, from which a 3-fold value (3σ) of standard deviation (σ) was determined and reported as LWR. A smaller value of 3σ indicates a pattern having a lower roughness and more uniform space width.

The results are shown in Tables 8 and 9.

TABLE 8

| | | Resist compo- sition | PEB temp. (° C.) | Eop (mJ/cm$^2$) | EL (%) | MEF | LWR (nm) |
|---|---|---|---|---|---|---|---|
| Example | 4-1 | R-1 | 90 | 35 | 15 | 3.4 | 3.8 |
| | 4-2 | R-2 | 85 | 31 | 17 | 3.7 | 3.6 |
| | 4-3 | R-3 | 95 | 36 | 14 | 3.3 | 3.7 |
| | 4-4 | R-4 | 95 | 35 | 16 | 3.8 | 3.5 |
| | 4-5 | R-5 | 95 | 37 | 14 | 3.5 | 3.6 |
| | 4-6 | R-6 | 95 | 39 | 15 | 3.8 | 3.5 |
| | 4-7 | R-7 | 90 | 37 | 17 | 3.4 | 3.7 |
| | 4-8 | R-8 | 95 | 34 | 16 | 3.4 | 3.7 |
| | 4-9 | R-9 | 100 | 33 | 14 | 3.6 | 3.5 |
| | 4-10 | R-10 | 95 | 34 | 15 | 3.8 | 3.8 |
| | 4-11 | R-11 | 105 | 38 | 14 | 3.8 | 3.4 |
| | 4-12 | R-12 | 90 | 39 | 16 | 3.4 | 3.7 |
| | 4-13 | R-13 | 90 | 30 | 15 | 3.6 | 3.6 |
| | 4-14 | R-14 | 100 | 36 | 14 | 3.7 | 3.5 |

TABLE 9

| | | Resist compo- sition | PEB temp. (° C.) | Eop (mJ/cm$^2$) | EL (%) | MEF | LWR (nm) |
|---|---|---|---|---|---|---|---|
| Comparative Example | 3-1 | R-15 | 85 | 38 | 11 | 4.4 | 4.2 |
| | 3-2 | R-16 | 90 | 45 | 10 | 4.4 | 4.3 |
| | 3-3 | R-17 | 95 | 39 | 9 | 4.7 | 4.6 |
| | 3-4 | R-18 | 90 | 38 | 10 | 4.6 | 4.6 |
| | 3-5 | R-19 | 95 | 40 | 9 | 4.5 | 4.4 |
| | 3-6 | R-20 | 95 | 42 | 10 | 4.4 | 4.7 |
| | 3-7 | R-21 | 100 | 40 | 9 | 4.7 | 4.4 |
| | 3-8 | R-22 | 105 | 46 | 8 | 4.8 | 4.6 |
| | 3-9 | R-23 | 95 | 41 | 10 | 4.7 | 4.8 |

It is evident from Tables 8 and 9 that the inventive resist composition is improved in sensitivity, EL, MEF and LWR upon negative pattern formation via organic solvent development. This suggests that the inventive resist composition is suited for the organic solvent development process.

6) ArF Lithography Patterning Test #3: Evaluation of L/S Pattern

Examples 5-1 to 5-14 and Comparative Examples 4-1 to 4-9

On a substrate, a spin-on carbon film ODL-50 (Shin-Etsu Chemical Co., Ltd.) having a carbon content of 80 wt % was deposited to a thickness of 200 nm and a silicon-containing spin-on hard mask SHB-A940 (Shin-Etsu Chemical Co., Ltd.) having a silicon content of 43 wt % was deposited thereon to a thickness of 35 nm. On this substrate for trilayer process, each of the resist compositions (Inventive R-1 to R-14 or Comparative R-15 to R-23) was spin coated and baked on a hotplate at 100° C. for 60 seconds to form a resist film of 100 nm thick.

Using an ArF excimer laser immersion lithography scanner NSR-610C (Nikon Corp., NA 1.30, a 0.98/0.78, 4/5 annular illumination), pattern exposure was performed through a 6% halftone phase shift mask bearing a line pattern with a pitch of 100 nm and a space width of 50 nm (on-wafer size). Water was used was the immersion liquid. After exposure, the wafer was baked (PEB) at the temperature shown in Tables 10 and 11 for 60 seconds and developed. Specifically, 2.38 wt % TMAH aqueous solution was injected from a development nozzle for 3 seconds while the wafer was spun at 30 rpm, which was followed by stationary puddle development for 27 seconds. As a result, the unexposed regions of the resist film that were shielded by the mask were dissolved in the developer, that is, image reversal took place, to form a line-and-space (L/S) pattern with a space width of 50 nm and a pitch of 100 nm.

Evaluation of Sensitivity

The L/S pattern was observed under an electron microscope. As an index of sensitivity, the optimum dose (Eop, mJ/cm$^2$) which provided a L/S pattern with a space width of 50 nm and a pitch of 100 nm was determined.

Evaluation of EL

The exposure dose which provided an L/S pattern with a space width of 50 nm±10% (i.e., 45 nm to 55 nm) was determined. EL (%) is calculated from the exposure doses according to the following equation:

$$EL\ (\%) = (|E1-E2|/Eop) \times 100$$

wherein E1 is an exposure dose which provides an L/S pattern with a space width of 45 nm and a pitch of 100 nm, E2 is an exposure dose which provides an L/S pattern with a space width of 55 nm and a pitch of 100 nm, and Eop is the optimum exposure dose which provides an L/S pattern with a space width of 50 nm and a pitch of 100 nm.

Evaluation of MEF

An L/S pattern was formed by exposure in the optimum dose (determined in the sensitivity evaluation) through the mask with the pitch fixed and the line width varied. MEF was calculated from variations of the mask line width and the pattern space width according to the following equation:

$$MEF = (\text{pattern space width})/(\text{mask line width}) - b$$

wherein b is a constant. A value closer to unity (1) indicates better performance.

Evaluation of LWR

The L/S pattern formed by exposure in the optimum dose (determined in the sensitivity evaluation) was observed under TDSEM S-9380 (Hitachi Hitechnologies, Ltd.). The space width was measured at longitudinally spaced apart 10 points, from which a 3-fold value (3σ) of standard deviation (σ) was determined and reported as LWR. A smaller value of 3σ indicates a pattern having a lower roughness and more uniform space width.

The results are shown in Tables 10 and 11.

TABLE 10

| | | Resist composition | PEB temp. (° C.) | Eop (mJ/cm$^2$) | EL (%) | MEF | LWR (nm) |
|---|---|---|---|---|---|---|---|
| Example | 5-1 | R-1 | 90 | 34 | 14 | 3.5 | 3.8 |
| | 5-2 | R-2 | 85 | 31 | 15 | 3.6 | 3.6 |
| | 5-3 | R-3 | 95 | 35 | 13 | 3.3 | 3.8 |
| | 5-4 | R-4 | 95 | 34 | 15 | 3.6 | 3.5 |
| | 5-5 | R-5 | 95 | 38 | 12 | 3.4 | 3.7 |
| | 5-6 | R-6 | 95 | 36 | 14 | 3.7 | 3.5 |
| | 5-7 | R-7 | 90 | 32 | 14 | 3.4 | 3.4 |
| | 5-8 | R-8 | 95 | 33 | 15 | 3.5 | 3.7 |
| | 5-9 | R-9 | 100 | 35 | 13 | 3.5 | 3.6 |
| | 5-10 | R-10 | 95 | 34 | 12 | 3.8 | 3.7 |
| | 5-11 | R-11 | 105 | 38 | 14 | 3.7 | 3.5 |
| | 5-12 | R-12 | 90 | 36 | 13 | 3.5 | 3.6 |
| | 5-13 | R-13 | 90 | 34 | 14 | 3.6 | 3.6 |
| | 5-14 | R-14 | 100 | 37 | 14 | 3.8 | 3.4 |

TABLE 11

| | | Resist composition | PEB temp. (° C.) | Eop (mJ/cm$^2$) | EL (%) | MEF | LWR (nm) |
|---|---|---|---|---|---|---|---|
| Comparative Example | 4-1 | R-15 | 85 | 38 | 9 | 4.4 | 4.3 |
| | 4-2 | R-16 | 90 | 42 | 9 | 4.3 | 4.4 |
| | 4-3 | R-17 | 95 | 39 | 9 | 4.5 | 4.6 |
| | 4-4 | R-18 | 90 | 37 | 8 | 4.2 | 4.7 |
| | 4-5 | R-19 | 95 | 40 | 8 | 4.6 | 4.4 |
| | 4-6 | R-20 | 95 | 41 | 9 | 4.5 | 4.5 |
| | 4-7 | R-21 | 100 | 37 | 9 | 4.4 | 4.5 |
| | 4-8 | R-22 | 105 | 43 | 7 | 4.6 | 4.7 |
| | 4-9 | R-23 | 95 | 40 | 9 | 4.7 | 4.6 |

It is evident from Tables 10 and 11 that the inventive resist composition is improved in sensitivity, EL, MEF and LWR upon positive pattern formation via alkaline aqueous solution development. This suggests that the inventive resist composition is suited for the alkaline aqueous solution development process.

Japanese Patent Application No. 2016-188374 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A sulfonium salt having the formula (2):

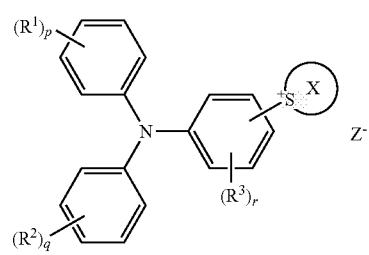

(2)

wherein $R^1$ to $R^3$ are each independently a $C_1$-$C_{20}$ straight, branched or cyclic monovalent hydrocarbon group which may contain a heteroatom, a pair of $R^1$ and $R^2$, $R^1$ and $R^3$, or $R^2$ and $R^3$ may bond together to form a ring with the benzene rings to which they are attached and the nitrogen atom therebetween, or a plurality of grows $R^1$ to $R^3$ may be the same or different and bond together to form a ring with the carbon atoms on the benzene ring to which they are attached, when p, q and/or r is an integer of at least 2, p and q are each independently an integer of 0 to 5, r is an integer of 0 to 4, and $Z^-$ is a monovalent anion, and the ring X is a $C_2$-$C_{30}$ cyclic hydrocarbon group which contains the sulfur atom as a part of the ring and may contain a heteroatom.

2. The sulfonium salt of claim 1 wherein Z is an anion having the formula (3):

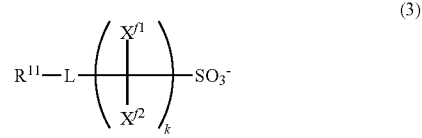

(3)

wherein $R^{11}$ is a $C_1$-$C_{40}$ straight, branched or cyclic monovalent hydrocarbon group which may contain a heteroatom, L is a single bond or a divalent linking group, $X^{f1}$ and $X^{f2}$ are each independently hydrogen, fluorine or a fluorinated alkyl group, and k is an integer of 0 to 4.

3. A sulfonium salt having the formula (1):

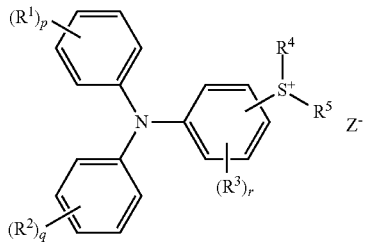 (1)

wherein $R^1$ to $R^3$ are each independently a $C_1$-$C_{20}$ straight, branched or cyclic monovalent hydrocarbon group which may contain a heteroatom, a pair of $R^1$ and $R^2$, $R^1$ and $R^3$, or $R^2$ and $R^3$ may bond together to form a ring with the benzene rings to which they are attached and the nitrogen atom therebetween, or a plurality of groups $R^1$ to $R^3$ may be the same or different and bond together to form a ring with the carbon atoms on the benzene ring to which they are attached, when p, q and/or r is an integer of at least 2, $R^4$ and $R^5$ are each independently a $C_1$-$C_{30}$ straight, branched or cyclic monovalent hydrocarbon group which may contain a heteroatom, or a pair of $R^4$ and $R^5$ may bond together to form a ring with the sulfur atom to which they are attached, p and q are each independently an integer of 0 to 5, r is an integer of 0 to 4, and $Z^{31}$ is a monovalent anion, Z is an anion having the formula (4) or (5):

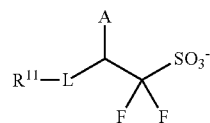 (4)

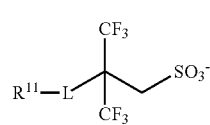 (5)

wherein $R^{11}$ is a $C_1$-$C_{40}$ straight, branched or cyclic monovalent hydrocarbon group which may contain a heteroatom, L is a single bond or a divalent linking group, and A hydrogen or trifluoromethyl.

4. A photoacid generator comprising the sulfonium salt of claim 1.

5. A resist composition comprising the photoacid generator of claim 4, a base resin and a solvent.

6. The resist composition of claim 5, wherein the base resin contains a polymer comprising recurring units having the formula (a) and recurring units having the formula (b):

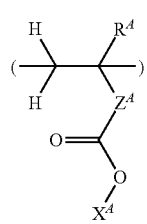 (a)

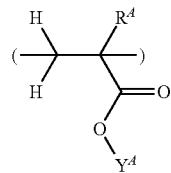 (b)

wherein $R^A$ is hydrogen, fluorine, methyl or trifluoromethyl, $Z^A$ is a single bond, phenylene group, naphthylene group or (backbone)-C(=O)—O—Z'—, Z' is a $C_1$-$C_{10}$ straight, branched or cyclic alkylene group which may contain a hydroxyl radical, ether bond, ester bond or lactone ring, or phenylene group or naphthylene group, $X^A$ is an acid labile group, and $Y^A$ is hydrogen or a polar group having at least one structure selected from the group consisting of hydroxyl, cyano, carbonyl, carboxyl, ether, ester, sulfonic acid ester, carbonate moiety, lactone ring, sultone ring and carboxylic anhydride.

7. The resist composition of claim 5, wherein the solvent is an organic solvent.

8. The resist composition of claim 5, further comprising other photoacid generator.

9. The resist composition of claim 8 wherein the other photoacid generator has the formula (6) or (7):

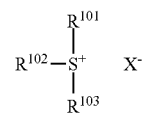 (6)

wherein $R^{101}$, $R^{102}$ and $R^{103}$ are each independently a $C_1$-$C_{20}$ straight, branched or cyclic monovalent hydrocarbon group which may contain a heteroatom, any two of $R^{101}$, $R^{102}$ and $R^{103}$ may bond together to form a ring with the sulfur atom to which they are attached, $X^-$ is an anion selected from the formulae (6A) to (6D):

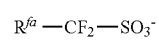 (6A)

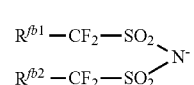 (6B)

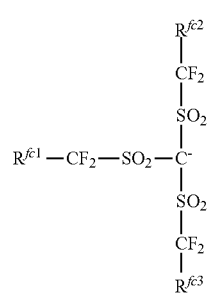 (6C)

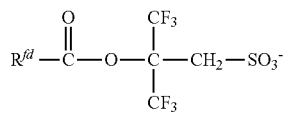 (6D)

wherein $R^{fa}$, $R^{fb1}$, $R^{fb2}$, $R^{fc1}$, $R^{fc2}$ and $R^{fc3}$ are each independently fluorine or a $C_1$-$C_{40}$ straight, branched or cyclic monovalent hydrocarbon group which may contain a heteroatom, or a pair of $R^{fb1}$ and $R^{fb2}$, or $R^{fc1}$ and $R^{fc2}$ may bond together to form a ring with the carbon atoms to which they are attached and any intervening atoms, $R^{fd}$ is a $C_1$-$C_{40}$ straight, branched or cyclic monovalent hydrocarbon group which may contain a heteroatom,

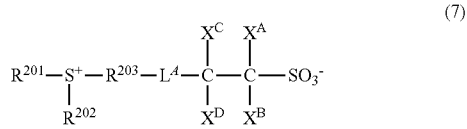

(7)

wherein $R^{201}$ and $R^{202}$ are each independently a $C_1$-$C_{30}$ straight, branched or cyclic monovalent hydrocarbon group which may contain a heteroatom, $R^{203}$ is a $C_1$-$C_{30}$ straight, branched or cyclic divalent hydrocarbon group which may contain a heteroatom, any two of $R^{201}$, $R^{202}$ and $R^{203}$ may bond together to form a ring with the sulfur atom to which they are attached, $L^A$ is a single bond, ether bond, or a $C_1$-$C_{20}$ straight, branched or cyclic divalent hydrocarbon group which may contain a heteroatom, $X^A$, $X^B$, $X^C$ and $X^D$ are each independently hydrogen, fluorine or trifluoromethyl, at least one of $X^A$, $X^B$, $X^C$ and $X^D$ being a substituent group other than hydrogen.

10. The resist composition of claim 5, further comprising a compound having the formula (8) or (9):

(8)

(9)

wherein $R^{q1}$ is hydrogen or a $C_1$-$C_{40}$ straight, branched or cyclic, monovalent hydrocarbon group which may contain a heteroatom, excluding the hydrocarbon group in which the hydrogen atom bonded to the carbon at α-position relative to the sulfo group is substituted by fluorine or fluoroalkyl, $R^{q2}$ is hydrogen or a $C_1$-$C_{40}$ straight, branched or cyclic monovalent hydrocarbon, group which may contain a heteroatom, and $Mq^+$ is an onium cation.

11. A resist composition comprising:
a photoacid generator comprising a sulfonium salt having the formula (1):

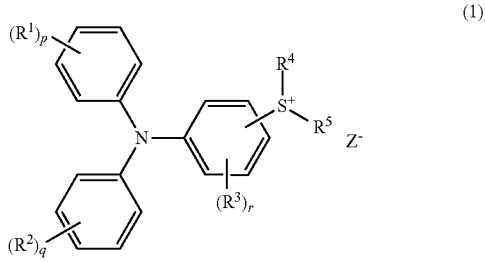

(1)

wherein $R^1$ to $R^3$ are each independently a $C_1$-$C_{20}$ straight, branched or cyclic monovalent hydrocarbon group which may contain a heteroatom, a pair of $R^1$ and $R^2$, $R^1$ and $R^3$, or $R^2$ and $R^3$ may bond together to form a ring with the benzene rings to which they are attached and the nitrogen atom therebetween, or a plurality of groups $R^1$ to $R^3$ may be the same or different and bond together to form a ring with the carbon atoms on, the benzene ring to which they are attached, when p, q and/or r is an integer of at least 2, $R^4$ and $R^5$ are each independently a $C_1$-$C_{30}$ straight, branched or cyclic monovalent hydrocarbon group which may contain a heteroatom, or a pair of $R^4$ and $R^5$ may bond together to form a ring with the sulfur atom to which the are attached, p and q are each independently an integer of 0 to 5, r is an integer of 0 to 4, and $Z^{31}$ is a monovalent anion, a base resin, a solvent, and an amine compound.

12. A resist composition comprising:
a photoacid generator comprising a sulfonium salt having the formula (1):

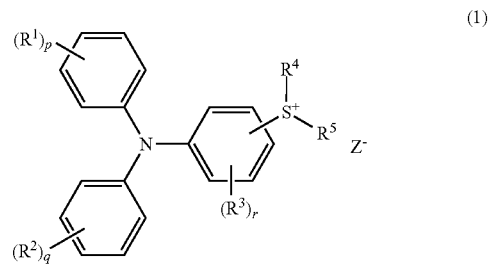

(1)

wherein $R^1$ to $R^3$ are each independently a $C_1$-$C_{20}$ straight, branched or cyclic monovalent hydrocarbon group which may contain a heteroatom, a pair of $R^1$ and $R^2$, $R^1$ and $R^3$, or $R^2$ and $R^3$ may bond together to form a ring with the benzene rings to which they are attached and the nitrogen atom therebetween, or a plurality of groups $R^1$ to $R^3$ may be the same or different and bond together to form a ring with the carbon atoms on, the benzene ring to which they are attached, when p, q and/or r is an integer of at least 2, $R^4$ and $R^5$ are each independently a $C_1$-$C_{30}$ straight, branched or cyclic monovalent hydrocarbon group which may contain a heteroatom, or a pair of $R^4$ and $R^5$ may bond together to form a ring with the sulfur atom to which the are attached, p and q are each independently an integer of 0 to 5, r is an integer of 0 to 4, and $Z^{31}$ is a monovalent anion, a base resin, a solvent, and a surfactant which is insoluble or substantially insoluble in water and soluble in alkaline developer, and/or a surfactant which is insoluble or substantially insoluble in water and alkaline developer.

13. A pattern forming process comprising the steps of applying a resist composition onto a substrate, prebaking to form a resist film, exposing a selected region of the resist film to KrF excimer laser, ArF excimer laser, EB or EUV through a photomask, baking, and developing the exposed resist film in a developer, wherein the resist composition comprises a photoacid generator comprising a sulfonium salt having the formula (1), a base resin and a solvent:

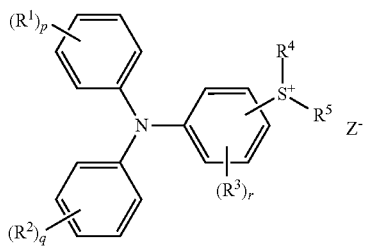

(1)

wherein $R^1$ to $R^3$ are each independently a $C_1$-$C_{20}$ straight, branched or cyclic monovalent hydrocarbon group which may contain a heteroatom, a pair of $R^1$ and $R^2$, $R^1$ and $R^3$, or $R^2$ and $R^3$ may bond together to form a ring with the benzene rings to which they are attached and the nitrogen atom therebetween, or a plurality of groups $R^1$ to $R^3$ may be the same or different and bond together to form a ring with the carbon atoms on the benzene ring to which they are attached, when p, q and/or r is an integer of at least 2, $R^4$ and $R^5$ are each independently a $C_1$-$C_{30}$ straight, branched or cyclic monovalent hydrocarbon group which may contain a heteroatom, or a pair of $R^4$ and $R^5$ may bond together to form a ring with the sulfur atom to which they are attached, p and q are each independently an integer of 0 to 5, r is an integer of 0 to 4, and $Z^{31}$ is a monovalent anion.

14. The pattern forming process of claim 13 wherein the developing step uses an alkaline aqueous solution as the developer, thereby forming a positive pattern in which an exposed region of the resist film is dissolved away and an unexposed region of the resist film is not dissolved.

15. The pattern forming process of claim 13 wherein the developing step uses an organic solvent as the developer, thereby forming a negative pattern in which an unexposed region of the resist film is dissolved away and an exposed region of the resist film is not dissolved.

16. The pattern forming process of claim 15 wherein the organic solvent is at least one solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

17. The process of claim 13 wherein the exposure step is carried out by immersion lithography while a liquid having a refractive index of at least 1.0 is held between the resist film and a projection lens.

18. The process of claim 17, further comprising the step of coating a protective film on the resist film, prior to the exposure step, wherein immersion lithography is carried out while the liquid is held between the protective film and the projection lens.

19. The process of claim 13 wherein the base resin contains a polymer comprising recurring units having the formula (a) and recurring units having the formula (b):

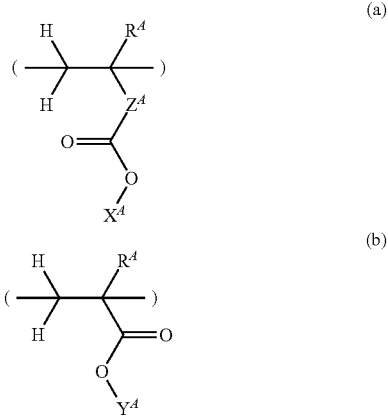

wherein $R^A$ is hydrogen, fluorine, methyl or trifluoromethyl, $Z^A$ is a single bond, phenylene group, naphthylene group or (backbone)-C(=O)-O-Z'-, Z' is a $C_1$-$C_{10}$ straight branched or cyclic alkylene group which may contain a hydroxyl radical, ether bond, ester bond or lactone ring, or phenylene group or naphthylene group, $X^A$ is an acid labile group, and $Y^A$ is hydrogen or a polar group having at least one structure selected from the group consisting of hydroxyl, cyano, carbonyl, carboxyl, ether, ester, sulfonic acid ester, carbonate moiety, lactone ring, sultone ring and carboxylic anhydride.

* * * * *